US008962260B2

(12) United States Patent
Sambursky et al.

(10) Patent No.: US 8,962,260 B2
(45) Date of Patent: Feb. 24, 2015

(54) METHOD AND DEVICE FOR COMBINED DETECTION OF VIRAL AND BACTERIAL INFECTIONS

(71) Applicant: Rapid Pathogen Screening, Inc., Sarasota, FL (US)

(72) Inventors: Robert P. Sambursky, Bradenton, FL (US); Robert W. VanDine, Montoursville, PA (US); Uma Mahesh Babu, Bradenton, FL (US); Peter Condon, Longboat Key, FL (US)

(73) Assignee: Rapid Pathogen Screening, Inc., Sarasota, FL (US)

( * ) Notice: Subject to any disclaimer, the term of this patent is extended or adjusted under 35 U.S.C. 154(b) by 0 days.

(21) Appl. No.: 13/790,160

(22) Filed: Mar. 8, 2013

(65) Prior Publication Data
US 2013/0196311 A1  Aug. 1, 2013

Related U.S. Application Data

(63) Continuation-in-part of application No. 12/782,162, filed on May 18, 2010, and a continuation-in-part of application No. 12/469,207, filed on May 20, 2009, now abandoned, and a continuation-in-part of
(Continued)

(51) Int. Cl.
*G01N 33/569* (2006.01)
*G01N 33/558* (2006.01)
(Continued)

(52) U.S. Cl.
CPC ........... *G01N 33/569* (2013.01); *G01N 33/558* (2013.01); *G01N 33/54366* (2013.01);
(Continued)

(58) Field of Classification Search
CPC .......... G01N 33/558; G01N 33/54366; G01N 30/90; G01N 33/56983; G01N 33/523; G01N 21/8483; G01N 33/526
USPC ........ 435/5, 7.1, 7.2, 7.9–7.95; 436/810, 514, 436/518, 524–532, 536–541
See application file for complete search history.

(56) References Cited

U.S. PATENT DOCUMENTS

| 4,299,916 A | 11/1981 | Litman et al. |
| 4,405,711 A | 9/1983 | Masuda et al. |

(Continued)

FOREIGN PATENT DOCUMENTS

| DE | 4439429 C2 | 2/1996 |
| DE | 19622503 C2 | 7/1998 |

(Continued)

OTHER PUBLICATIONS

Aouifi, et al. Usefulness of Procalcitonin for Diagnosis of Infection in Cardia Surgical Patents, Crit Care Med. 2000, vol. 28, No. 9, pp. 3171-3176.
(Continued)

*Primary Examiner* — Melanie Y Brown
*Assistant Examiner* — Erik B Crawford
(74) *Attorney, Agent, or Firm* — Brown & Michaels, PC

(57) ABSTRACT

A lateral flow assay is capable of detecting and differentiating viral and bacterial infections. A combined point of care diagnostic device tests markers for viral infection and markers for bacterial infection, to effectively assist in the rapid differentiation of viral and bacterial infections. In some preferred embodiments, bimodal methods and devices determine if an infection is bacterial and/or viral. A dual use two strip sample analysis device includes a first lateral flow chromatographic test strip to detect MxA and a low level of C-reactive protein and a second lateral flow chromatographic test strip to detect high levels of C-reactive protein. In some preferred embodiments, the sample is a fingerstick blood sample.

41 Claims, 19 Drawing Sheets

Related U.S. Application Data application No. PCT/US2009/057775, filed on Sep. 22, 2009, and a continuation-in-part of application No. 12/481,631, filed on Jun. 10, 2009, now Pat. No. 8,470,608, and a continuation-in-part of application No. 12/958,454, filed on Dec. 2, 2010, now Pat. No. 8,609,433, and a continuation-in-part of application No. 12/502,626, filed on Jul. 14, 2009, now Pat. No. 8,669,052, and a continuation-in-part of application No. 12/502,662, filed on Jul. 14, 2009, now Pat. No. 8,614,101, and a continuation-in-part of application No. 13/788,616, filed on Mar. 7, 2013, now Pat. No. 8,815,609.

(60) Provisional application No. 61/179,059, filed on May 18, 2009, provisional application No. 61/071,833, filed on May 20, 2008, provisional application No. 61/060,258, filed on Jun. 10, 2008, provisional application No. 61/266,641, filed on Dec. 4, 2009, provisional application No. 61/331,966, filed on May 6, 2010, provisional application No. 61/352,093, filed on Jun. 7, 2010, provisional application No. 61/392,981, filed on Oct. 14, 2010, provisional application No. 61/080,879, filed on Jul. 15, 2008, provisional application No. 61/098,935, filed on Sep. 22, 2008.

(51) Int. Cl.
*G01N 33/543* (2006.01)
*G01N 30/90* (2006.01)
*G01N 33/52* (2006.01)
*G01N 21/84* (2006.01)
*B82Y 30/00* (2011.01)

(52) U.S. Cl.
CPC .............. *G01N30/90* (2013.01); *G01N 33/523* (2013.01); *G01N 21/8483* (2013.01); *G01N 33/526* (2013.01); *G01N 33/54346* (2013.01); *G01N 33/56911* (2013.01); *G01N 33/56983* (2013.01); *B82Y 30/00* (2013.01); *B01J 2219/00576* (2013.01); *B01J 2219/00648* (2013.01); *B01J 2219/00725* (2013.01); *B01J 2219/0074* (2013.01); *B01J 2219/00743* (2013.01); *Y10S 436/81* (2013.01)
USPC .................. 435/7.1; 435/5; 435/7.2; 435/7.9; 436/810; 436/514; 436/518; 436/524; 436/536

(56) References Cited

U.S. PATENT DOCUMENTS

| | | |
|---|---|---|
| 4,429,050 A | 1/1984 | Yasuda et al. |
| 4,473,652 A | 9/1984 | Okazaki et al. |
| 4,508,820 A | 4/1985 | Merril et al. |
| 4,554,254 A | 11/1985 | Krystal |
| 4,703,016 A | 10/1987 | Merril |
| 4,861,711 A | 8/1989 | Friesen et al. |
| 4,920,046 A | 4/1990 | McFarland et al. |
| 4,956,302 A | 9/1990 | Gordon et al. |
| 4,960,691 A | 10/1990 | Gordon et al. |
| 4,960,692 A | 10/1990 | Lentrichia et al. |
| 4,963,325 A | 10/1990 | Lennon et al. |
| 4,981,786 A | 1/1991 | Dafforn et al. |
| 5,026,653 A | 6/1991 | Lee et al. |
| 5,120,643 A | 6/1992 | Ching et al. |
| 5,221,678 A | 6/1993 | Atkinson et al. |
| 5,312,921 A | 5/1994 | Glazer et al. |
| 5,348,891 A | 9/1994 | van Es et al. |
| 5,405,430 A | 4/1995 | Groves et al. |
| 5,415,994 A | 5/1995 | Imrich et al. |
| 5,436,134 A | 7/1995 | Haugland et al. |
| 5,496,562 A | 3/1996 | Burgoyne |
| 5,569,608 A | 10/1996 | Sommer |
| 5,607,863 A | 3/1997 | Chandler |
| 5,637,469 A | 6/1997 | Wilding et al. |
| 5,658,751 A | 8/1997 | Yue et al. |
| 5,695,949 A | 12/1997 | Galen et al. |
| 5,705,353 A | 1/1998 | Oh et al. |
| 5,714,341 A | 2/1998 | Thieme et al. |
| 5,756,126 A | 5/1998 | Burgoyne |
| 5,763,162 A | 6/1998 | Glazer et al. |
| 5,783,687 A | 7/1998 | Glazer et al. |
| 5,807,527 A | 9/1998 | Burgoyne |
| 5,824,268 A | 10/1998 | Bernstein et al. |
| 5,863,740 A | 1/1999 | Kientsch-Engel et al. |
| 5,869,345 A | 2/1999 | Chandler |
| 5,877,028 A | 3/1999 | Chandler et al. |
| 5,888,778 A | 3/1999 | Shuber |
| 5,939,252 A | 8/1999 | Lennon et al. |
| 5,945,345 A | 8/1999 | Blatt et al. |
| 5,972,386 A | 10/1999 | Burgoyne |
| 5,985,327 A | 11/1999 | Burgoyne |
| 5,985,675 A | 11/1999 | Charm et al. |
| 5,989,813 A | 11/1999 | Gerdes |
| 5,998,220 A | 12/1999 | Chandler |
| 6,002,734 A | 12/1999 | Steinman |
| 6,017,767 A | 1/2000 | Chandler |
| 6,037,127 A | 3/2000 | Ebersole et al. |
| 6,046,058 A | 4/2000 | Sun |
| 6,054,272 A | 4/2000 | Glazer et al. |
| 6,060,237 A | 5/2000 | Nygren et al. |
| 6,087,184 A | 7/2000 | Magginetti et al. |
| 6,106,779 A | 8/2000 | Buechler et al. |
| 6,136,610 A | 10/2000 | Polito et al. |
| 6,146,589 A | 11/2000 | Chandler |
| 6,225,046 B1 | 5/2001 | Vesey et al. |
| 6,235,539 B1 | 5/2001 | Carpenter |
| 6,284,550 B1 | 9/2001 | Carroll et al. |
| 6,335,205 B1 | 1/2002 | Bausback |
| 6,350,578 B1 | 2/2002 | Stark et al. |
| 6,355,429 B1 | 3/2002 | Nygren et al. |
| 6,358,752 B1 | 3/2002 | Durst et al. |
| 6,514,773 B1 | 2/2003 | Klein et al. |
| 6,548,309 B1 | 4/2003 | Moore et al. |
| 6,555,390 B2 | 4/2003 | Chandler |
| 6,565,808 B2 | 5/2003 | Hudak et al. |
| 6,566,101 B1 | 5/2003 | Shuber et al. |
| 6,569,627 B2 | 5/2003 | Wittwer et al. |
| 6,602,669 B2 | 8/2003 | Letsinger et al. |
| 6,727,073 B1 | 4/2004 | Moore et al. |
| 6,783,938 B2 | 8/2004 | Nygren et al. |
| 6,818,452 B2 | 11/2004 | Wong |
| 6,875,619 B2 | 4/2005 | Blackburn |
| 6,893,880 B2 | 5/2005 | Carpenter |
| 6,902,900 B2 | 6/2005 | Davies et al. |
| 7,189,522 B2 | 3/2007 | Esfandiari |
| 7,267,992 B2 | 9/2007 | Goerlach-Graw et al. |
| 7,309,611 B2 | 12/2007 | DiNello et al. |
| 7,314,763 B2 | 1/2008 | Song et al. |
| 7,341,837 B2 | 3/2008 | Lawton |
| 7,354,614 B2 | 4/2008 | Quinlan et al. |
| 7,371,582 B2 | 5/2008 | Nahm et al. |
| 7,374,950 B2 | 5/2008 | Kang et al. |
| 7,379,167 B2 | 5/2008 | Mawhirt et al. |
| 7,384,598 B2 | 6/2008 | Quirk et al. |
| 7,393,697 B2 | 7/2008 | Charlton |
| 7,425,302 B2 | 9/2008 | Piasio et al. |
| 7,459,314 B2 | 12/2008 | Guo et al. |
| 7,583,379 B2 | 9/2009 | Zhao et al. |
| 7,704,729 B2 | 4/2010 | Chandler |
| 7,723,124 B2 | 5/2010 | Aberl et al. |
| 7,732,132 B2 | 6/2010 | Huang et al. |
| 7,736,890 B2 | 6/2010 | Sia et al. |
| 7,741,103 B2 | 6/2010 | Guirguis |
| 7,910,381 B2 | 3/2011 | Ford et al. |
| 8,383,422 B2 | 2/2013 | Katada et al. |
| 8,603,835 B2 | 12/2013 | Esfandiari |
| 2003/0027866 A1 | 2/2003 | Johnson et al. |
| 2003/0049658 A1 | 3/2003 | Smart et al. |
| 2003/0073121 A1 | 4/2003 | Mendel-Hartvig et al. |

(56) References Cited

U.S. PATENT DOCUMENTS

| | | |
|---|---|---|
| 2003/0104506 A1 | 6/2003 | Durst et al. |
| 2003/0108940 A1 | 6/2003 | Inoko et al. |
| 2003/0119209 A1 | 6/2003 | Kaylor et al. |
| 2003/0186463 A1 | 10/2003 | Hudak et al. |
| 2003/0190681 A1 | 10/2003 | Shai |
| 2004/0101889 A1 | 5/2004 | Letsinger et al. |
| 2004/0110167 A1 | 6/2004 | Gerdes et al. |
| 2004/0152142 A1 | 8/2004 | Klepp et al. |
| 2004/0156037 A1 | 8/2004 | Mawhirt et al. |
| 2004/0203086 A1 | 10/2004 | Piasio et al. |
| 2004/0241779 A1 | 12/2004 | Piasio et al. |
| 2005/0032244 A1 | 2/2005 | Nie et al. |
| 2005/0130120 A1 | 6/2005 | Lambotte et al. |
| 2005/0164305 A1 | 7/2005 | Golz et al. |
| 2005/0175992 A1 | 8/2005 | Aberl et al. |
| 2005/0181517 A1 | 8/2005 | Chandler et al. |
| 2005/0221386 A1 | 10/2005 | Turner et al. |
| 2005/0227223 A1 | 10/2005 | Miyawaki |
| 2005/0227275 A1 | 10/2005 | Jung et al. |
| 2005/0239056 A1 | 10/2005 | Piasio et al. |
| 2005/0272106 A1 | 12/2005 | Moore et al. |
| 2006/0003390 A1 | 1/2006 | Schaffler et al. |
| 2006/0019406 A1 | 1/2006 | Wei et al. |
| 2006/0024843 A1 | 2/2006 | Lee et al. |
| 2006/0057608 A1 | 3/2006 | Kaufman |
| 2006/0110285 A1 | 5/2006 | Piasio et al. |
| 2006/0121626 A1 | 6/2006 | Imrich |
| 2006/0147927 A1 | 7/2006 | Geddes et al. |
| 2006/0148097 A1 | 7/2006 | Yamaguchi et al. |
| 2006/0160078 A1 | 7/2006 | Cardy et al. |
| 2006/0172434 A1 | 8/2006 | Rowell |
| 2006/0199278 A1 | 9/2006 | Leclipteux et al. |
| 2006/0216704 A1 | 9/2006 | Newton et al. |
| 2006/0223192 A1 | 10/2006 | Smith et al. |
| 2006/0240569 A1 | 10/2006 | Goldenbaum et al. |
| 2006/0263907 A1 | 11/2006 | Zweig |
| 2007/0003992 A1 | 1/2007 | Pentyala |
| 2007/0015290 A1 | 1/2007 | Raj |
| 2007/0059682 A1 | 3/2007 | Aberl et al. |
| 2007/0141564 A1 | 6/2007 | Aberl et al. |
| 2007/0184506 A1 | 8/2007 | Klepp |
| 2007/0202497 A1 | 8/2007 | Renuart et al. |
| 2007/0224701 A1 | 9/2007 | Rosenstein |
| 2007/0264629 A1 | 11/2007 | Holmes et al. |
| 2008/0003141 A1 | 1/2008 | Iketani |
| 2008/0032319 A1 | 2/2008 | Nam |
| 2008/0057493 A1 | 3/2008 | Gao et al. |
| 2008/0085525 A1 | 4/2008 | Van Herwijnen |
| 2008/0102473 A1 | 5/2008 | Fouquet et al. |
| 2008/0145843 A1 | 6/2008 | Song |
| 2008/0194041 A1 | 8/2008 | Guirguis |
| 2008/0318341 A1 | 12/2008 | Esfandiari |
| 2009/0011436 A1 | 1/2009 | Piasio et al. |
| 2009/0047673 A1 | 2/2009 | Cary |
| 2009/0155811 A1 | 6/2009 | Natan et al. |
| 2009/0203059 A1 | 8/2009 | Davis et al. |
| 2009/0232702 A1 | 9/2009 | Wu et al. |
| 2009/0289201 A1 | 11/2009 | Babu et al. |
| 2009/0291508 A1 | 11/2009 | Babu et al. |
| 2009/0305231 A1 | 12/2009 | Weidemaier et al. |
| 2009/0305290 A1 | 12/2009 | Sambursky et al. |
| 2010/0015634 A1 | 1/2010 | VanDine et al. |
| 2010/0112725 A1 | 5/2010 | Babu et al. |
| 2010/0143891 A1 | 6/2010 | Aberl et al. |
| 2010/0143941 A1 | 6/2010 | Wu et al. |
| 2010/0209297 A1 | 8/2010 | Raj et al. |
| 2010/0279310 A1 | 11/2010 | Sia et al. |
| 2010/0291536 A1 | 11/2010 | Viljoen et al. |
| 2010/0297611 A1 | 11/2010 | Sambursky et al. |
| 2011/0136258 A1* | 6/2011 | Sambursky et al. ......... 436/501 |
| 2011/0151584 A1 | 6/2011 | Esfandiari |
| 2011/0275542 A1 | 11/2011 | Eden et al. |

FOREIGN PATENT DOCUMENTS

| | | |
|---|---|---|
| EP | 0306772 A1 | 3/1989 |
| EP | 0582231 A1 | 2/1994 |
| EP | 1489416 A1 | 12/2004 |
| JP | 2006189317 A1 | 7/2006 |
| JP | 2007322310 A1 | 12/2007 |
| JP | 2008537145 A1 | 9/2008 |
| WO | 9960402 A1 | 11/1999 |
| WO | 0136975 A1 | 5/2001 |
| WO | 03073817 A2 | 9/2003 |
| WO | 2006115866 A1 | 11/2006 |
| WO | 2007063326 A2 | 6/2007 |
| WO | 2007070117 A1 | 6/2007 |
| WO | 2007081330 A1 | 7/2007 |
| WO | 2007110779 A2 | 10/2007 |
| WO | 2007123507 A1 | 11/2007 |
| WO | 2008014709 A1 | 2/2008 |
| WO | 2009044167 A1 | 4/2009 |
| WO | 2009108224 A1 | 9/2009 |

OTHER PUBLICATIONS

Baigent SJ, et al. Inhibition of beta interferon transcription by noncytopathogenic bovine viral diarrhea virus is though an interferon regulatory factor 3-dependent mechanism, J Vir. 2002; 76(18):8979-8988.

Baker MD, et al., Outpatient management without antibiotics of fever in selected infants. N Engl J Med 1993;329:1437-1441.

Barden LS, Dowell SF, Schwartz B, Lackey C. Current attitudes regarding use of antimicrobial agents, Clin Pediatr. 1998; 37:665-672.

Barnard, et al., Development of an Oligonucleotide-Based SNP Detection Method on Lateral Flow Strips Using Hexapet Tags, Point of Care, vol. 4, No. 3, pp. 108-118 (Sep. 2005).

Baskin MN, et al., Outpatient treatment of febrile infants 28 to 89 days of age with intramuscular administration of ceftriaxone. J Pediatr 1992;120:22-27.

Berezovski, et al., Cell lysis inside the capillary facilitated by transverse diffusion of laminar flow profiles (TDLFP), Anal Bioanal Chem (2007) 387:91-96.

Bruning et al., A rapid chromatographic strip test for the pen-side diagnosis of rinderpest virus, Journal of Virological Methods 81 (1999) 143-154.

Bulletin of the World Health Organization (WHO), 1998, 76(1): 101-103.

Calandra T, et al. Prognostic values of tumor necrosis factor/cachectin, interleukin-1, interferon-alpha, and interferon-gamma in the serum of patients with septic shock. J Infect Dis 1990;161:982-987.

Cals JWL, et al. Effect of point of care testing for C reactive protein and training in communication skills on antibiotic use in lower respiratory tract infections: cluster randomised trial, BMJ 2009; 338:b1374.

Charleston B and Stewart HJ. An interferon-induced Mx protein: cDNA sequence and high-level expression in the endometrium of pregnant sheep, Gene 1993; 137:327-331.

Chi H, Chin NC, LI WC, Huang FY, Etiology of acute pharyngitis in children: is antibiotic therapy needed?, J Microbial Immunol Infect 2003;36(1): 26-30.

Chieux V, et al. MxA protein in capillary blood of children with viral infections. J Med Virol. 1999;59:547-51.

Chieux V, et al. The MxA protein levels in whole blood lysates of patients with various viral infections. J Virol Methods. 1998;70:183-91.

Choi, et al., A rapid, simple measurement of human albumin in whole blood using a fluorescence immunoassay (I), Clinica Chimica Acta 339 (2004) 147-156.

Dahler Eriksen BS, et al. Near-patient test for C-reactive protein in general practice: assessment of clinical, organizational, and economic outcomes, Clin Chem 1999, 45(4):478-485.

Diederichsen HZ, et al. Randomised controlled trial of CRP rapid test as a guide to treatment of respiratory infections in general practice, Scand J Prim Health Care 2000, 18(1):39-43.

(56) References Cited

OTHER PUBLICATIONS

Dineva et al., Simultaneous Visual Detection of Multiple Viral Amplicons by Dipstick Assay, Journal of Clinical Microbiology, Aug. 2005, p. 4015-4021.
Djavani et al., Early Blood Profiles of Virus Infection in a Monkey Model for Lassa Fever, Journal of Virology, Aug. 2007, p. 7960-7973, vol. 81, No. 15.
Envitec SmartClip Brochure, Rapid Detection of Drugs of Abuse in Saliva or Sweat; ENVITEC-Wismar GmbH, Wismar, Germany, www.envitec.com, 2004.
Ewig, S., and A. Torres. Severe community-acquired pneumonia. Curr. Opin. Crit. Care. 2002; 8:453-460.
Extended European Search Report dated Apr. 17, 2013. European Application No. 10835165.1 (PCT/US2010058827).
Falk G, Fahey T. C-reactive protein and community-acquired pneumonia in ambulatory care: systematic review of diagnostic accuracy studies. Family Practice 2009;26(1): 10-21.
Flood RG, et al. The utility of serum C-reative protein in differentiating bacterial from nonbacterial pneumonia in children, Ped Infec Dis J 2008; 27(2):95-99.
Forster J, et al. MxA protein in infants and children with respiratory tract infection. Acta Paediatr 1996;85:163-167.
FTA Nucleic Acid Collection, Storage and Purification, http://whatman.com/products.aspx?PID=108, 2007.
Girardin E, et al. Tumor necrosis factor and interleukin-1 in the serum of children with severe infectious purpura. N Engl J Med 1988;319:397-400.
Goetschy JF,et al. Regulation of the interferon-inducible IFI-78K gene, the human equivalent of the murine Mx gene, by interferons, double-stranded RNA, certain cytokines, and viruses. J Virol 1989; 63(6):2616-22.
Gonzales R, et al. Excessive Antibiotic Use for Acute Respiratory Infections in the United States. Clin Infect Dis 2001;33:757-62.
Haller O, Kochs G, Interferon induced Mx proteins: Dynamin like GTPases with antiviral activity, Traffic. 2002; 3:710-717.
Halminen M, et al. Expression of MxA protein in blood lymphocytes discriminates between viral and bacterial infections in febrile children. Pediatr Res 1997;41:647-650.
Hansson LO, Carlsson I, Hansson E, Hovelius B, Svensson P, Tryding N, Measurement of C-reactive protein and the erythrocyte sedimentation rate in general practice, Scand J Prim Health Care 1995;13:39-45.
Hatherill et al. Diagnostic Markers of Infection: Comparison of Procalcitonin with C Reative Protein and Leucocyte Count; Arch Dis Child 1999: 81: 417-21.
Hedlund J, Hansson LO. Procalcitonin and C-reactive protein levels in community-acquired pneumonia: correlation with etiology and prognosis. Infection 2000;28:68-73.
Hjortdahl P, Melbye H, Does near-to-patient testing contribute to the diagnosis of streptococcal haryngitis in adults?, Scand J Prim Health Care 1994;12:70-6.
Horisberger MA. Interferon-induced human protein MxA is a GTPase which binds transiently to cellular proteins. J Virol 1992;66:4705-4709.
Huang N, et al. Antibiotic prescribing for children with nasopharyngitis (common colds), upper respiratory infections, and bronchitis who have health-professional parents. Pediatrics 2005;116:826-832.
International Search Report and Written Opinion dated Feb. 18, 2010, International Application No. PCT/US2009/050645.
International Search Report and Written Opinion dated Jan. 22, 2010, International Application No. PCT/US2009/046848.
International Search Report and Written Opinion dated Mar. 12, 2010, International Application No. PCT/US2009/050653.
International Search Report and Written Opinion for International Application No. PCT/US2010/058827 Issued on Nov. 30, 2011.
Itazawa T, et al. Increased lymphoid MxA expression in acute asthma exacerbation in children. Allergy 2001;56:895-898.
Itazawa T, et al. Theophylline metabolism in acute asthma with MxA-indicated viral infection. Pediatr Int 2006;48:54-57.
Jaskiewicz JA, et al. Febrile infants at low risk for serious bacterial infection—an appraisal of the Rochester criteria and implications for management. Pediatrics 1994;94: 390-396.
Jennings LC, Anderson TP, Beynon KA, et al., Incidence and characteristics of viral community-acquired pneumonia in adults 1Thorax 2008;63:42-48.
Karle, et al., Application of FTA-based Technology for Sample Collection, Transport, Purification, and Storage of PCR-ready Plant DNA (Nov. 2003).
Kawamura M, et al. New sandwich-type enzyme-linked immunosorbent assay for human MxA protein in a whole blood using monoclonal antibodies against GTP-binding domain for recognition of viral infection. J Clin Lab Anal. 2012;26:174-83.
Le Bon A, Tough DF, Links between innate and adaptive immunity via type I interferon, Curr Opin Immunol. 2002; 14: 432-436.
Lindback S, Hellgren U, Julander I, Hansson LO, The value of C-reactive protein as a marker of bacterial infection in patients with septicaemia/endocarditis and influenza, Scand J Infect Dis 1989;21:543-9.
International PCT Search Report for PCT/US2014/019771; Jun. 27, 2014; 14 pages.
Makela MJ, et al. Viruses and bacteria in the etiology of the common cold. J Clin Microbiol 1998; 36: 539-542.
McCarthy PL, Frank AL, Ablow RC, Masters SJ, Dolan TF, Value of C-reactive protein test in the differentiation of bacterial and viral pneumonia, J Pediatr 1978;92:454-6.
Melbye H, Straume B, Aasebo U, Brox J, The diagnosis of adult pneumonia in general practice. The diagnostic value of history, physical examination and some blood tests, Scand J Prim Health Care 1988;6:111-7.
Moulin F, et al. Procalcitonin in children admitted to hospital with community acquired pneumonia. Arch Dis Child 2001;84:332-336.
Muller et al. Calcitonin precursors are reliable markers of sepsis in a medical intensive care unit; Crit Care Med. 2000, 28: 977-83.
Muller-Doblies D, et al. Innate immune responses of calves during transient infection with a noncytopathic strain of bovine viral diarrhea virus, Clin Diag Lab Imm 2004; 11(2):302-312.
Nakabayashi M, et al. MxA-based recognition of viral illness in febrile children by a whole blood assay. Pediatr Res 2006;60:770-774.
Neumark T, et al. Use of rapid diagnostic tests and choice of antibiotics in respiratory tract infections in primary healthcare—a 6-y follow-up study, Scand J Infect Dis 2010; 42:90-96.
Okamura JM, et al. Potential clinical applications of C-reactive protein. J Clin Lab Anal 1990;4:231-235.
O'Mahony, et al., Integration of Bacteria Capture via Filtration and in Situ Lysis for Recovery of Plasmid DNA under Industry-Compatible Conditions, Biotechnol. Prog. 2007, 23, 895-903.
Parida M.M., Rapid and real-time detection technologies for emerging viruses of biomedical importance, J. Biosci. 33 (4), Nov. 2008, 617-628.
Pavlovic J, et al. Human and mouse Mx proteins inhibit different steps of the influenza virus multiplication cycle, J Vir. 1992; 66(4):2564-2569.
Penel et al., Fever and Solid Tumor: Diagnostic Utility of Procalcitonin and C-reactive Protein, Rev Med Interne 2001; 22:706-714.
Pitossi F, et al. A functional GTP-binding motif is necessary for antiviral activity of Mx proteins. J Vir. 1993; 67 (11):6726-32.
Powell and Dagan, Criteria for exclusion of serious bacterial infections in young infants, Journal of Pediatrics, Nov. 1992, pp. 831-832.
Rapid test for pink eye may curb overuse of antibiotics, http://www.stjohns.com/news/pinkeyetest.aspx (Jan. 26, 2009).
Restrepo, MI., JH Jorgensen, EM Mortensen, Anzueto A, Severe community-acquired pneumonia: current outcomes, epidemiology, etiology, and therapy, Curr. Opin. Infect. Dis. 2001;14:703-709.
Ronni T, et al. Control of IFN-inducible MxA gene expression in human cells. J Immunol 1993;150:1715-1726.
Ronni T, et al. Regulation of IFB-alpha/beta, MxA, 2'3 ,5'3 -oligoadenylate synthetase, and HLA gene expression in influenza A-infected human lung epithelial cells, J Immunol. 1997;158:2363-2374.

(56) References Cited

OTHER PUBLICATIONS

Rothenberger et al., Detection of acute phase response and infection. The role of procalcitonin and C-reactive protein, Clin Chem Lab Med, 1999, 37:275-9.
Sambursky et al., The RPS Adeno Detector for Diagnosing Adenoviral Conjunctivitis, Ophthalmology, vol. 113, No. 10, pp. 1758-1764 (Oct. 2006).
Sambursky, 510-K Summary of Safety and Effectiveness (Sep. 14, 2005), 48 pages.
Schwarz et al., Serum procalcitonin levels in bacterial and abacterial meningitis, Crit Care Med 2000, 28: 1828-32.
Selberg et al., Discrimination of sepsis and systemic inflammatory response syndrome by determination of circulating plasma concentrations of procalcitonin, protein complement 3a, and interleukin-6, Crit Care Med 2000, 28: 2793-8.
Simon A, et al. Interferon-regulated Mx genes are not responsive to interleukin-1, tumor necrosis factor, and other cytokines. J Virol 1991;65:968-971.
Smith RP, et al. C-reactive protein. A clinical marker in community-acquired pneumonia. Chest 1995;108:1288-1291.
Smith RP, Lipworth BJ. C-reactive protein in simple community-acquired pneumonia. Chest 1995;107:1028-1031.
Smith SM, et al. Antibiotics for acute bronchitis, Cochrane Database Syst Rev 2004, Issue 4, 47 pages.
Staeheli P, et al. Mx protein: constitutive expression in 3T3 cells transformed with cloned Mx cDNA confers selective resistance to influenza virus. Cell 1986;44:147-158.
Steinman MA, Gonzales R, Linder JA, Landefeld CS, Changing Use of Antibiotics in Community—Based Outpatient Practice, 1991-1999, Ann Intern Med 2003, 138(7):525-533.
Stuart J, Lewis SM. Monitoring the acute phase response [Editorial]. BMJ 1988;297:1143-4.
Summah H and Qu JM. Biomarkers: a definite plus in pneumonia, Mediators of Inflammation 2009; Article ID 675753, 9 pages.
Suprin et al., Procalcitonin: a valuable indicator of infection in a medical ICU? Intensive Care Med 2000, 26: 1232-8.
Thompson D, Milford Ward A, Whicher H, The value of acute phase protein measurements in clinical practice, Ann Clin Biochem 1992;29:123-31.
Toikka P, et al. Serum procalcitonin, C-reactive protein and interleukin-6 for distinguishing bacterial and viral pneumonia in children. Pediatr Infec Dis J 2000;19(7):598-602.
Towbin H, et al. A whole blood immunoassay for the interferon-inducible human Mx protein. J Interferon Res. 1992;12:67-74.
Uchio, et al., Rapid Diagnosis of Adenoviral Conjunctivitis on Conjunctival Swabs by 10-Minute Immunochromatography, Opthalmology, vol. 104, No. 8, Aug. 1997, pp. 1294-1299.
Udeh et al., Cost Effectiveness of a Point-of-Care Test for Adenoviral Conjunctivitis, The American Journal of the Medical Sciences, vol. 336, No. 3, pp. 254-264 (Sep. 2008).
Ugarte et al., Procalcitonin as a marker of infection in the intensive care unit, Crit Care Med 1999, 27: 498-504.
van der Bliek AM. Functional diversity in the dynamin family. Trends Cell Biol 1999;9:96-102.
Van Duijn HJ, et al. Determinants of prescribing of second-choice antibiotics for upper and lower respiratory tract episodes in Dutch general practice, J Antimicrob Chemother 2005;56(2):420-422.
Verheij T JM, et al., NHGStandaard Acuut hoesten. [Dutch College of General Practitioners Guidelines on Acute Cough], Huisarts Wet 2003;46(9):496-506. (Original reference in Dutch together with English machine translation.).
Viallon, et al. Serum and ascetic procalcitonin levels in cirrhotic patients with spontaneous bacterial peritonitis: diagnostic value and relationship to pro-inflammatory cytokines, Intensive Care Med 2000, 26: 1082-8.
Young B, Gleeson M, Cripps AW, C-reactive protein: a critical review, Pathology 1991;23:118-24.
Zurcher T, et al. Mechanism of human MxA protein action: variants with changed antiviral properties, EMBO Journal 1992; 11(4):1657-1661.
Extended European Search Report, European Patent Office, Feb. 9, 2012.
Leung, et al. InfectCheck CRP barcode-style lateral flow assay for semi-quantitative detection of C-reactive protein in distinguishing between bacterial and viral infections. Journal of Immunological Methods, 336 (2008), pp. 30-36.
Search Report and Written Opinion dated Sep. 25, 2014 for PCT/US2014/019773.

\* cited by examiner

Fig. 1

| Disease State | Visual Test Result | C-reactive Protein (> 15mg/L) | MxA (> 235 ng/ml) |
|---|---|---|---|
| Viral Infection | A | Negative | Positive |
| Bacterial Infection | B | Positive | Negative |
| Co Infection | C | Positive | Positive |
| Non-Infectious | D | Negative | Negative |

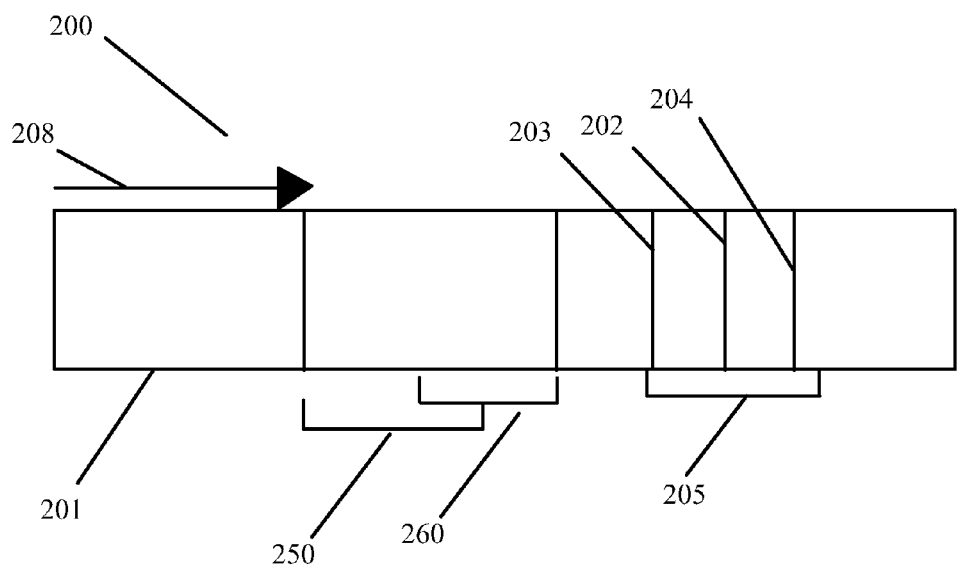
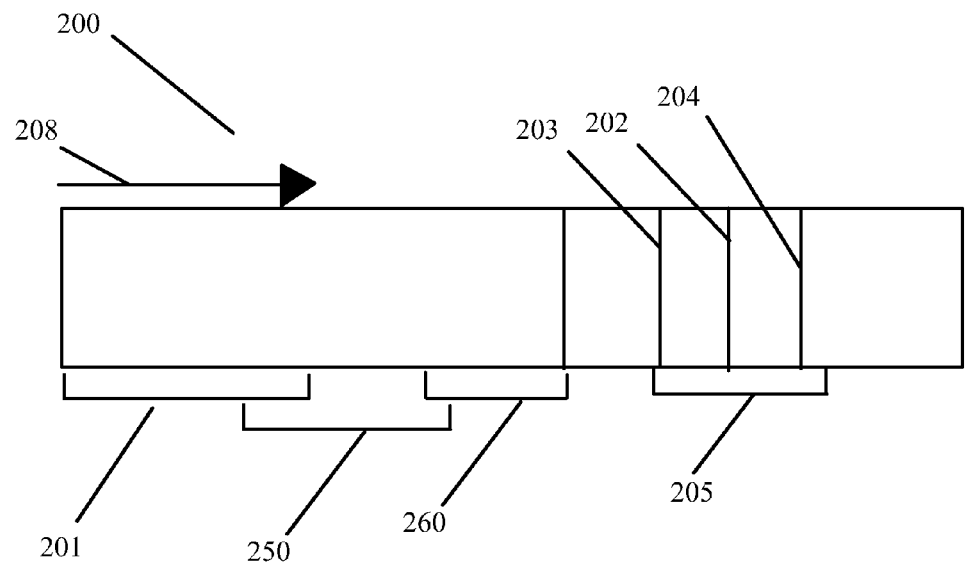

METHOD AND DEVICE FOR COMBINED DETECTION OF VIRAL AND BACTERIAL INFECTIONS

REFERENCE TO RELATED APPLICATIONS

This is a continuation-in-part patent application of:

Co-pending application Ser. No. 12/782,162, filed May 18, 2010, entitled "METHOD AND DEVICE FOR COMBINED DETECTION OF VIRAL AND BACTERIAL INFECTIONS", which claims one or more inventions which were disclosed in Provisional Application No. 61/179,059, filed May 18, 2009, entitled "METHOD AND DEVICE FOR COMBINED DETECTION OF VIRAL AND BACTERIAL INFECTIONS" and is also a continuation-in-part application of application Ser. No. 12/469,207, filed May 20, 2009, entitled "NANOPARTICLES IN DIAGNOSTIC TESTS", which claimed priority from Provisional Application No. 61/071,833, filed May 20, 2008, entitled "NANOPARTICLES IN DIAGNOSTIC TESTS", and is also a continuation-in-part of PCT application Serial Number PCT/US2009/057775, filed Sep. 22, 2009, entitled "METHOD AND DEVICE FOR COMBINED DETECTION OF VIRAL AND BACTERIAL INFECTIONS";

Co-pending application Ser. No. 12/481,631, filed Jun. 10, 2009, entitled "COMBINED VISUAL/FLUORESCENCE ANALYTE DETECTION TEST", which claimed priority from Provisional Application No. 61/060,258, filed Jun. 10, 2008, entitled "COMBINED VISUAL/FLUORESCENCE ANALYTE DETECTION TEST";

Co-pending application Ser. No. 12/502,626, filed Jul. 14, 2009, entitled "LATERAL FLOW NUCLEIC ACID DETECTOR", which claimed priority from Provisional Application No. 61/080,879, filed Jul. 15, 2008, entitled "LATERAL FLOW NUCLEIC ACID DETECTOR";

Co-pending application Ser. No. 12/502,662, filed Jul. 14, 2009, entitled "IN SITU LYSIS OF CELLS IN LATERAL FLOW IMMUNOASSAYS", which claimed priority from Provisional Application No. 61/098,935, filed Sep. 22, 2008, entitled "IN SITU LYSIS OF CELLS IN LATERAL FLOW IMMUNOASSAYS";

Co-pending application Ser. No. 12/958,454, filed Dec. 2, 2010, entitled "MULTIPLANAR LATERAL FLOW ASSAY WITH SAMPLE COMPRESSOR", which claimed priority from Provisional Application No. 61/266,641, filed Dec. 4, 2009, entitled "LATERAL FLOW NUCLEIC ACID DETECTOR", Provisional Application No. 61/331,966, filed May 6, 2010, entitled "MULTIPLANAR LATERAL FLOW ASSAY WITH SAMPLE COMPRESSOR", Provisional Application No. 61/352,093, filed Jun. 7, 2010, entitled "LATERAL FLOW ASSAYS", and Provisional Application No. 61/392,981, filed Oct. 14, 2010, entitled "MULTIPLANAR LATERAL FLOW ASSAY WITH SAMPLE COMPRESSOR"; and Co-pending application Ser. No. 13/788,616, filed Mar. 7, 2013, entitled "MULTIPLANAR LATERAL FLOW ASSAY WITH DIVERTING ZONE".

The benefit under 35 USC §119(e) of the United States provisional applications is hereby claimed, and the aforementioned applications are hereby incorporated herein by reference.

BACKGROUND OF THE INVENTION

1. Field of the Invention

The invention pertains to the field of lateral flow immunoassays. More particularly, the invention pertains to a lateral flow immunoassay that rapidly detects viral and bacterial infection.

2. Description of Related Art

Fever is a common cause of childhood visits to urgent care centers for both family practice and pediatric offices. Most commonly, this relates to either a respiratory infection or gastroenteritis. The high incidence of fever in children and the precautious administration of unnecessary antibiotics is reason to develop a rapid screening test for the biomarkers that indicate viral and/or bacterial infection.

It is often challenging to differentiate viral from bacterial infections. This is especially true in young children that cannot verbalize their symptoms and in the outpatient setting where access to laboratory diagnostics is expensive, time consuming, and requires several days to produce a result. More recently, many new diagnostic markers have been identified. Several of these markers show great promise to differentiate viral from bacterial infections. Two such proteins include MxA and C-Reactive Protein (CRP). Most respiratory infections are related to pharyngitis of which 40% are caused by viruses and 25-50% by group A beta hemolytic streptococcus. The lesser causes are acute bronchiolitis and pneumonia.

Severe community-acquired pneumonia is caused by bacterial infections in around 60% of cases, requiring admission to an intensive care unit (ICU) for about 10% of patients. The remaining 30% are related to respiratory viruses.

About 80% of all antimicrobials are prescribed in primary care, and up to 80% of these are for respiratory tract indications. Respiratory tract infections are by far the most common cause of cough in primary care. Broad spectrum antibiotics are often prescribed for cough, including acute bronchitis, and many of these prescriptions will benefit patients only marginally if at all, and may cause side effects and promote antibiotic resistance. Factors that urge physicians to give antibiotics include the absence of an adequate diagnostic marker of bacterial infections, the concern about lack of patient follow-up, and the time pressure.

Mx proteins are members of the superfamily of high molecular weight GTPases. Accordingly, these GTPases are upregulated by type 1 alpha/beta or type II interferons (IFN). The Mx GTPases are expressed exclusively in IFN alpha/beta but not IFN gamma treated cells. Type I interferons play important roles in innate immune responses and have immunomodulatory, antiproliferative, and antiviral functions. Human MxA, a 78 kDa protein, accumulates in the cytoplasm of IFN treated cells and inhibits the replication of a wide range of viruses. MxA protein may offer certain advantages as a marker for viral infection over the other induced proteins such as 2',5'-oligoadenylate synthetase, because of its lower basal concentration, longer half-life (2.3 days) and fast induction. MxA mRNA is detectable in isolated peripheral blood white blood cells stimulated with IFN within 1 to 2 h of IFN induction, and MxA protein begins to accumulate shortly thereafter.

Studies have shown that MxA protein expression in peripheral blood is a sensitive and specific marker for viral infection. The higher MxA levels in the viral infection group compared with the bacterial infection group can be explained by the fact that the MxA protein is induced exclusively by type I IFN and not by IFN-gamma, IL-1, TNF-alpha, or any of the other cyotokines by bacterial infection. Serum type I IFN levels remain within normal limits, even in patients with severe bacterial infections.

Similarly, most viral infections have been reported to cause little acute phase response, and low C-Reactive Protein (CRP) concentrations have been used to distinguish illnesses of viral origin from those of bacterial etiology. Because the plasma concentration of CRP increases rapidly after stimulation and decreases rapidly with a short half-life, CRP can be a very useful tool in diagnosing and monitoring infections and inflammatory diseases. In Scandinavia, point of care CRP testing is part of the routine evaluation of patients with respiratory infections in general practice, and its use has proved cost-effective. In general practice, CRP is found valuable in the diagnosis of bacterial diseases and in the differentiation between bacterial and viral infections. Often the diagnostic value of CRP is found superior to that of the erythrocyte sedimentation rate (ESR) and superior or equal to that of the white blood cell count (WBC).

Clinically, it can be challenging to differentiate certain systemic viral and bacterial infections. Bacterial cultures are usually performed in cases of severe infection such as pneumonia, or when the consequence of missing a diagnosis can lead to severe complications, such as with Strep throat. Often times, cultures are difficult to obtain. Unfortunately, viral cultures are not routinely performed due to the significant time delay in receiving results. New viral screening PCR panels are useful but they are expensive and do not provide information at the point of care. Thus, there remains a need for a simple, easy to use diagnostic test that is capable of differentiating viral and bacterial infections.

SUMMARY OF THE INVENTION

The present invention provides a lateral flow assay that is capable of detecting and differentiating viral and bacterial infections. A combined point of care diagnostic device tests markers for viral infection and markers for bacterial infection, to effectively assist in the rapid differentiation of viral and bacterial infections. In one preferred embodiment, the bacterial marker is CRP. In another preferred embodiment, the viral marker is MxA. In some embodiments of the invention, it is unnecessary to lyse the cells in the sample prior to applying it to the device.

In one preferred embodiment, a method determines if an infection is bacterial and/or viral by first collecting a sample. The sample is then transferred to a dual use two strip sample analysis device. The sample analysis device includes a first lateral flow chromatographic test strip with a first reagent zone and a second reagent zone. The first reagent zone includes at least one first reagent specific to a low level of C-reactive protein such that, when the sample contacts the first reagent, a first labeled complex forms if the low level of C-reactive protein is present in the sample. The second reagent zone includes at least one second reagent specific to MxA such that, when the sample contacts the second reagent, a second labeled complex forms if MxA is present in the sample. The first lateral flow chromatographic test strip also includes a first detection zone comprising a first binding partner which binds to the first labeled complex; and a second binding partner which binds to the second labeled complex. The two strip lateral flow assay device also includes a second lateral flow chromatographic test strip parallel in a lateral flow direction to the first lateral flow chromatographic test strip. The second lateral flow chromatographic test strip includes at least one third reagent zone including at least one third reagent specific to a high level of C-reactive protein, such that, when the sample contacts the third reagent, a third labeled complex forms if the high level of C-reactive protein is present in the sample. The third reagent on the second lateral flow chromatographic test strip only detects a level of C-reactive protein that is higher than the level of C-reactive protein detected by the second reagent on the first lateral flow chromatographic test strip. The second lateral flow chromatographic test strip also includes a second detection zone with a third binding partner which binds to the third labeled complex. The sample is also analyzed for a presence of the low level of C-reactive protein, MxA, and the high level of C-reactive protein.

In another preferred embodiment, a dual use two strip lateral flow assay device detects a bacterial and/or viral marker in a sample. The device includes a first lateral flow chromatographic test strip with a first reagent zone and a second reagent zone. The first reagent zone includes at least one first reagent specific to a low level of C-reactive protein such that, when the sample contacts the first reagent, a first labeled complex forms if the low level of C-reactive protein is present in the sample. The second reagent zone includes at least one second reagent specific to MxA such that, when the sample contacts the second reagent, a second labeled complex forms if MxA is present in the sample. The first lateral flow chromatographic test strip also includes a first detection zone comprising a first binding partner which binds to the first labeled complex; and a second binding partner which binds to the second labeled complex. The two strip lateral flow assay device also includes a second lateral flow chromatographic test strip parallel in a lateral flow direction to the first lateral flow chromatographic test strip. The second lateral flow chromatographic test strip includes at least one third reagent zone comprising at least one third reagent specific to a high level of C-reactive protein, such that, when the sample contacts the third reagent, a third labeled complex forms if the high level of C-reactive protein is present in the sample. The third reagent on the second lateral flow chromatographic test strip only detects a level of C-reactive protein that is higher than the level of C-reactive protein detected by the second reagent on the first lateral flow chromatographic test strip. The second lateral flow chromatographic test strip also includes a second detection zone with a third binding partner which binds to the third labeled complex.

Another preferred embodiment is a method for determining if an infection is bacterial and/or viral, and includes the step of collecting a sample. The sample is then transferred to a sample analysis device. The sample analysis device includes a sample compressor with a first reagent zone including at least one first reagent specific to a low level of C-reactive protein such that, when the sample contacts the first reagent, a first labeled complex forms if the low level of C-reactive protein is present in the sample, and at least one second reagent specific to MxA such that, when the sample contacts the second reagent, a second labeled complex forms if MxA is present in the sample, and a second reagent zone including at least one third reagent specific to a high level of C-reactive protein, where the third reagent only detects a level of C-reactive protein that is higher than the level of C-reactive protein detected by the second reagent, such that, when the sample contacts the third reagent, a third labeled complex forms if the high level of C-reactive protein is present in the sample. The device also includes a first lateral flow chromatographic test strip that includes a first detection zone including a first binding partner which binds to the first labeled complex, a second binding partner which binds to the second labeled complex and a first diverting zone located upstream of the first detection zone on the lateral flow chromatographic test strip. The first diverting zone interrupts lateral flow on the first lateral flow chromatographic test strip. The device also includes a second lateral flow chromatographic test strip parallel in a lateral flow direction to the first lateral flow chromatographic test strip. The second lateral flow chromatographic test strip includes a second detection zone including a third binding partner which binds to the third labeled complex and a second diverting zone located upstream of the first detection zone on the lateral flow chromatographic test strip. The second diverting zone interrupts lateral flow on the second lateral flow chromatographic test strip. The device also includes a first sample application zone where sample is placed on the sample analysis device. The first sample application zone is located in a location selected from the group consisting of: i) on the first lateral flow chromatographic test strip upstream of the detection zone and ii) on the first reagent zone of the sample compressor. The device also includes a second sample application zone where sample is placed on the sample analysis device. The second sample application zone is located in a location selected from the group consisting of: i) on the second lateral flow chromatographic test strip upstream of the detection zone and ii) on the second reagent zone of the sample compressor. The sample compressor is in a different plane than the first lateral flow chromatographic test strip and the second lateral flow chromatographic test strip. The first reagent zone of the sample compressor creates a bridge over the first diverting zone and the second reagent zone of the sample compressor creates a bridge over the second diverting zone, diverting flow onto the sample compressor and returning flow to the first chromatographic test strip and the second chromatographic test strips at the end of the first diverting zone and the second diverting zone. The sample is analyzed for a presence of the low level of C-reactive protein, MxA, and the high level of C-reactive protein.

Another preferred embodiment is a lateral flow device for detecting an analyte in a sample. The device includes a sample compressor with a first reagent zone including at least one first reagent specific to a low level of C-reactive protein such that, when the sample contacts the first reagent, a first labeled complex forms if the low level of C-reactive protein is present in the sample, and at least one second reagent specific to MxA such that, when the sample contacts the second reagent, a second labeled complex forms if MxA is present in the sample, and a second reagent zone including at least one third reagent specific to a high level of C-reactive protein, where the third reagent only detects a level of C-reactive protein that is higher than the level of C-reactive protein detected by the second reagent, such that, when the sample contacts the third reagent, a third labeled complex forms if the high level of C-reactive protein is present in the sample. The device also includes a first lateral flow chromatographic test strip that includes a first detection zone including a first binding partner which binds to the first labeled complex, a second binding partner which binds to the second labeled complex and a first diverting zone located upstream of the first detection zone on the first lateral flow chromatographic test strip. The first diverting zone interrupts lateral flow on the first lateral flow chromatographic test strip. The device also includes a second lateral flow chromatographic test strip parallel in a lateral flow direction to the first lateral flow chromatographic test strip. The second lateral flow chromatographic test strip includes a second detection zone comprising a third binding partner which binds to the third labeled complex and a second diverting zone located upstream of the first detection zone on the lateral flow chromatographic test strip. The second diverting zone interrupts lateral flow on the second lateral flow chromatographic test strip. The device also includes a first sample application zone where sample is placed on the sample analysis device. The first sample application zone is located in a location selected from the group consisting of: i) on the first lateral flow chromatographic test strip upstream of the detection zone and ii) on the first reagent zone of the sample compressor. The device also includes a second sample application zone where sample is placed on the sample analysis device. The second sample application zone is located in a location selected from the group consisting of: i) on the second lateral flow chromatographic test strip upstream of the detection zone and ii) on the second reagent zone of the sample compressor. The sample compressor is in a different plane than the first lateral flow chromatographic test strip and the second lateral flow chromatographic test strip. The first reagent zone of the sample compressor creates a bridge over the first diverting zone and the second reagent zone of the sample compressor creates a bridge over the second diverting zone, diverting flow onto the sample compressor and returning flow to the first chromatographic test strip and the second chromatographic test strips at the end of the first diverting zone and the second diverting zone.

In another preferred embodiment, a method simultaneously detects at least one extracellular analyte and at least one intracellular analyte, by collecting a sample and transferring the sample to a sample analysis device. The sample is also lysed and the extracellular analyte and the intracellular analyte are simultaneously detected on the same sample analysis device. In one preferred embodiment, the extracellular analyte is C-reactive protein and the intracellular analyte is MxA protein.

In another preferred embodiment, a method of detecting MxA protein and C-reactive protein in a sample includes the steps of adding the sample to a mixture of an antibody to MxA protein conjugated to a first label and an antibody to C-reactive protein conjugated to a second label different from the first label, detecting a presence of MxA protein by determining whether the antibody to MxA protein has agglutinated, and detecting a presence of C-reactive protein by determining whether the antibody to C-reactive protein has agglutinated.

In another preferred embodiment, a method of detecting the presence of an unknown viral infection in a sample first collects the sample. The sample is then transferred to a sample application zone of a sample analysis device. The sample analysis device includes a conjugate zone including a sialic acid nanomicelle with a label inside the nanomicelle and a detection zone laterally downstream from the sample application zone, which includes a sialic acid homolog nanoparticle. The sample is analyzed for a positive result in the detection zone.

In another preferred embodiment, a method of detecting the presence of an unknown viral infection in a sample first collects the sample. The sample is then transferred to a sample application zone of a sample analysis device. The sample analysis device includes a conjugate zone with a molecule selected from the group consisting of: a nanomicelle including a binding partner for a specific virus that causes the viral infection and a label and a sialic acid homolog nanomicelle including a label inside the nanomicelle. The sample analysis device also includes a detection zone laterally downstream from the sample application zone, with a nanoparticle specific for the virus that causes the viral infection. The sample is analyzed for a positive result in the detection zone.

BRIEF DESCRIPTION OF THE DRAWINGS

FIG. 1 shows rapid screening test window visual test results to distinguish viral and bacterial infections and an interpretation of those results.

FIG. 5C shows a sample analysis device including a lysis zone overlapping a reagent zone in an embodiment of the present invention.

FIG. 5D shows a sample analysis device including a lysis zone overlapping a sample application zone and a reagent zone in an embodiment of the present invention.

DETAILED DESCRIPTION OF THE INVENTION

Figure 2:
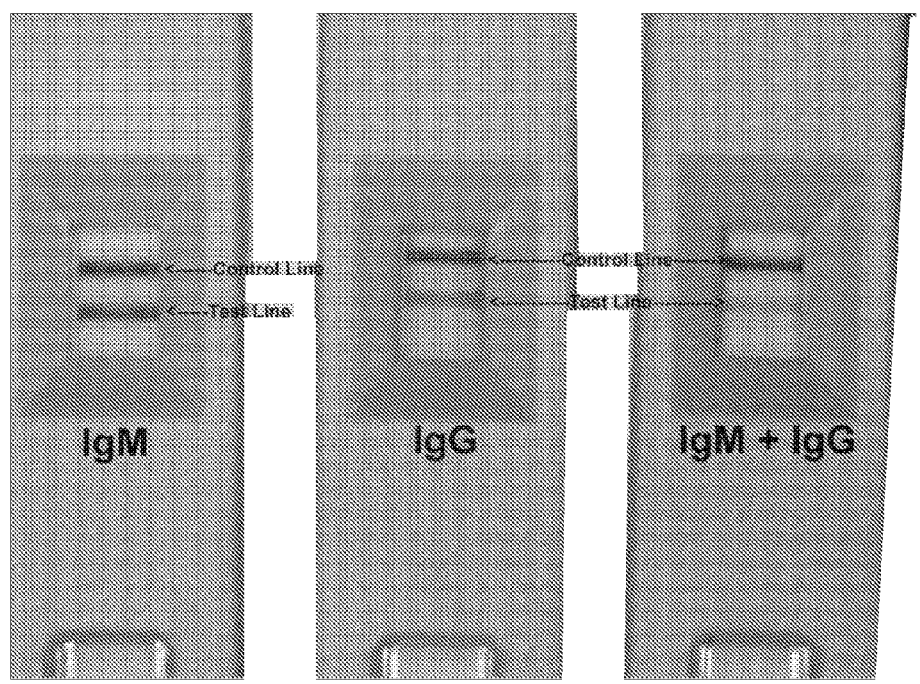
FIG. 2 shows three cassettes with different colored test lines.

The present invention provides a lateral flow assay that is capable of differentiating between viral and bacterial infections. Instead of testing for analytes specific to a particular bacterial or viral infection, the lateral flow assays described herein test for diagnostic markers that are specifically produced in a host in response to general, unspecified bacterial infection and general, unspecified viral infection. The diagnostic markers are preferably markers of an unspecified and/or unknown illness of bacterial or viral origin. In preferred embodiments, the diagnostic markers are specific markers for an immune response to an unspecified and/or unknown bacterial and/or viral infection.

A combined point of care diagnostic device tests markers for both viral and bacterial infection and can effectively assist in the rapid differentiation of viral and bacterial infections, for example at the outpatient office or during an urgent care visit. This ability can dramatically reduce health care costs by limiting misdiagnosis and the subsequent overuse of antibiotics. Such a practice may limit antibiotic allergies, adverse events, and antibiotic resistance. The rapid result obtained from the test also permits a diagnosis while the patient is still being examined by the practitioner. In a preferred embodiment, the test result is obtained in under 10 minutes after applying the sample to the device, and it is preferably read at approximately 10 minutes. In samples that are highly positive, the test line is visible within approximately 1-5 minutes.

In a preferred embodiment of the present invention, the lateral flow immunoassay device of the present invention includes a sample-transporting liquid, which can be a buffer, and a chromatographic test strip containing one or several fleece materials or membranes with capillary properties through which sample flows. Some preferred materials and membranes for the test strip include, but are not limited to, Polyethylene terephthalate (PET) fibers, such as Dacron® fibers, nitrocellulose, polyester, nylon, cellulose acetate, polypropylene, glass fibers, and combinations of these materials and their backings. In some embodiments of the invention, it is unnecessary to lyse the cells in the sample or treat the sample in any way prior to applying it to the test strip.

One preferred method of the present invention uses a sample analysis device, for example a chromatographic test strip, to determine if an infection is bacterial or viral. In this method, a sample is collected, and transferred to the chromatographic test strip. In a preferred embodiment, the sample is a sample including leukocytes. The test strip includes a reagent zone. The reagent zone preferably includes at least one first reagent specific to a bacterial marker such that, when the bacterial marker present in the sample contacts the first reagent, a first labeled complex forms. The reagent zone also preferably includes at least one second reagent specific to a viral marker such that, when the viral marker present in the sample contacts the second reagent, a second labeled complex forms. A detection zone includes both a bacterial marker binding partner which binds to the first labeled complex and a viral marker binding partner which binds to the second labeled complex. The sample is then analyzed for the presence of the viral marker and/or the bacterial marker.

A preferred embodiment of a device of the present invention includes a sample application zone. The device also includes a reagent zone, which includes at least one first reagent specific to a bacterial marker such that, when a bacterial marker present in the sample contacts the first reagent, a first labeled complex forms and at least one second reagent specific to a viral marker such that, when a viral marker present in the sample contacts the second reagent, a second labeled complex forms. A detection zone on the device includes a bacterial marker binding partner which binds to the first labeled complex and a viral marker binding partner which binds to the second labeled complex. One example of a device that could be used is a chromatographic test strip. In other preferred embodiments, some of the zones of the device are on one or more chromatographic test strips, while other zones (for example, the reagent zone, the sample application zone, and/or the control binding partner) are on a sample compressor, separate from and in a different plane than the chromatographic test strip.

In a preferred embodiment, the presence of the viral marker or the bacterial marker is indicated by a test line visible to the naked eye. The presence of the viral marker may be indicated by a first test line while the presence of the bacterial marker is indicated by a second test line. In some embodiments, the first test line displays a first color when positive and the second test line displays a second color different from the first color when positive. In embodiments where both the first test line and the second test line are located in the same space on the sample analysis device, a third color is preferably formed when both the first test line and the second test line are positive. In other embodiments, the two test lines are spatially separate from each other on the device.

Viral and bacterial infections are highly contagious and difficult to clinically differentiate due to a significant overlap in signs and symptoms, which often leads to the over prescription of systemic antibiotics and fosters antibiotic resistance. In developed countries, acute respiratory infections are the leading cause of morbidity, accounting for: 20% of medical consultations, 30% of absences from work, and 75% of all antibiotic prescriptions. In the U.S., there are approximately 76 million physician office visits annually for acute respiratory infection. The ability to detect an immune response to an infection aids in the clinical diagnostic ability to differentiate infections resulting from a viral and/or bacterial etiology.

In one preferred embodiment, the bacterial marker is CRP. In another preferred embodiment, the viral marker is MxA. In some preferred embodiments, the detection zone also includes a control line that is visible to the naked eye when the device is working.

In one preferred embodiment, the marker for viral infection is MxA and the marker for bacterial infection is C-reactive protein (CRP). High MxA protein levels are strongly correlated with systemic viral infection and increased CRP is more associated with bacterial infections. The present invention includes a rapid infectious screening test for identifying MxA and CRP in samples. MxA is present in leukocytes (white blood cells). Therefore, the sample can be taken anywhere leukocytes are available, for example in a peripheral blood sample, nasopharyngeal aspirates, tears, spinal fluid, and middle ear aspirates.

In some preferred embodiments with a single test strip containing CRP and MxA, the threshold concentration of CRP in a sample needed to elicit a positive result is approximately 6-15 mg/L. In other preferred embodiments, the threshold concentration of MxA in a sample to elicit a positive result may be as low as approximately 15 ng/ml; however, the threshold concentration may by higher, in a range from approximately 20 ng/ml to approximately 250 ng/ml. The threshold concentration may depend on the size of the sample being applied to the test strip, as well as its dilution, if applicable.

In some embodiments, the devices and methods described herein allow for the rapid, visual, qualitative in vitro detection of both MxA and CRP directly from peripheral whole blood. In one preferred embodiment, the test measures an immune response to a suspected viral and/or bacterial infection in patients older than one year that present within seven days of onset of a fever, with respiratory symptoms consistent with respiratory disease, and with a suspected diagnosis of acute pharyngitis or community acquired pneumonia. Negative results do not necessarily preclude respiratory infection and should not be used as the sole basis for diagnosis, treatment, or other management decisions. In some embodiments, the use of additional laboratory testing (e.g., bacterial and viral culture, immunofluorescence, viral polymerase chain reaction, and radiography) and clinical presentation is preferably additionally used to confirm whether a specific lower respiratory or pharyngeal pathogen exists.

In addition, there are some conditions that lead to erroneous false positives or negatives. These include, but are not limited to, current use of immunosuppressive drugs by the patient providing the sample, current use of oral anti-infective drugs by the patient providing the sample, current use of interferon therapy (e.g. for multiple sclerosis, HIV, HBV, HCV) by the patient providing the sample and live viral immunization within the last 30 days by the patient providing the sample. Both false negatives and false positives are possible since the levels can fluctuate due to therapy.

In preferred embodiments, the devices and methods are intended for professional use in an outpatient office or urgent care clinic and should be used in conjunction with other clinical (laboratory or radiographic) and epidemiological information.

In preferred embodiments, a dual-use dual chromatographic test strip assay detects the body's immune response to viral and/or bacterial infections in patients using a multiplexed pattern of results. In one specific preferred embodiment, the assay tests for Myxovirus resistance A (MxA), low levels of C-reactive Protein ("low" CRP), and high levels of C-reactive Protein ("high" CRP). Two test strips are preferably used. In some embodiments, a sample compressor in a different plane from the chromatographic test strips is also used. The first test strip assays for MxA and low levels of C-reactive Protein, and the second test strip is an assay for high levels of C-reactive Protein. The first test strip and/or the sample compressor include reagents to detect MxA protein and a low level of C-reactive protein. The second test strip and/or the sample compressor include reagents to detect a high level of C-reactive protein. The two test strips are preferably run side-by-side, and each strip also preferably includes a control line. The control reagents are preferably either on the test strips or on the sample compressor. These tests detect and classify biological infections as viral, bacterial, or a co-infection of virus and bacteria. In some preferred embodiments, the dual-use dual chromatographic test strip assay is used to detect samples from patients with a febrile respiratory illness.

In some preferred embodiments with two test strips, on the first test strip, a threshold concentration of CRP ("low" CRP level) of approximately 6-15 mg/L (serum cut-off value) in the sample is needed to elicit a positive result and a threshold concentration of at least 15 ng/ml MxA in a sample is needed to elicit a positive result. In other preferred embodiments, the threshold concentration for MxA may be in a range from approximately 15 ng/ml to approximately 250 ng/ml to elicit a positive result. The threshold concentration may depend on the size of the sample being applied to the test strip, as well as its dilution, if applicable. In one preferred embodiment, the threshold concentration of low CRP, for example in extracellular serum from a blood sample, is 7 mg/L for a fingerstick cut-off value, which is equivalent to 10 mg/L for a serum cut-off value. In one preferred embodiment, the threshold concentration of MxA, for example in peripheral blood mononuclear cells from a blood sample, is 40 ng/ml for a fingerstick cut off value, which is equivalent to a 40 ng/ml venous blood cut-off value. On the second test strip, a threshold concentration of CRP ("high" CRP level) of approximately 60-100 mg/L in the sample is needed to elicit a positive result in some preferred embodiments. In one particularly preferred embodiment, a threshold concentration of high CRP on the second test strip is approximately 80 mg/L on a fingerstick cut-off value.

In other embodiments, other markers for viral infection and/or bacterial infection may be used. For example, approximately 12% of host genes alter their expression after Lymphocytic Choriomeningitis Virus (LCMV) infection, and a subset of these genes can discriminate between virulent and nonvirulent LCMV infection. Major transcription changes have been given preliminary confirmation by quantitative PCR and protein studies and are potentially valuable candidates as biomarkers for arenavirus disease. Other markers for bacterial infection include, but are not limited to, procalcitonin, urinary trypsin inhibitor (uTi), lipopolysaccharide, IL-1, IL-6, IL-8, IL-10, ESR and an elevated WBC count (increased bands), Lactate, Troponin, vascular endothelial growth factor, platelet derived growth factor, cortisol, proadrenomedullin, macrophage migratory inhibitory marker, activated protein C, CD 4,8,13,14, or 64, caspase, placenta derived growth factor, calcitonin gene-related peptide, high mobility group 1, copeptin, naturietic peptides, lipopolysaccharide binding protein, tumor necrosis factor alpha, circulating endothelial progenitor cells, complement 3a, and triggering receptor expresssed on myeloid cells (trem-1).

In one embodiment, the infections being distinguished are respiratory infections. In other embodiments, other types of infections, which can be bacterial or viral, are differentiated using the system of the present invention. Some examples include, but are not limited to, encephalitis, meningitis, gastroenteritis, febrile respiratory illness (including bronchitis, pharyngitis, pneumonia), sinusitis, otitis media, urinary tract infections, and conjunctivitis.

Lateral flow devices are known, and are described in, e.g., U.S. Published Patent Application Nos. 2005/0175992 and 2007/0059682. The contents of both of these applications are incorporated herein by reference. Other lateral flow devices known in the art could alternatively be used with the systems and methods of the present invention.

U.S. Published Patent Application No. 2007/0059682 discloses detecting an analyte and a sample which can also contain one or more interfering substances. This publication teaches separating the analyte from the interfering substances by capturing the interfering substances on the chromatographic carrier, and detecting the analyte on the carrier separated from the interfering substances.

U.S. Published Patent Application No. 2005/0175992 discloses a method for detecting targets, such as pathogens and/or allergy-associated components, in a human body fluid where the body fluid sample is collected by a collection device, such as a swab member. The samples are transferred from the swab member to a sample analysis device, on which an analysis of the targets can occur by immunochemical or enzymatic means. The test result is capable of being displayed within a very short period of time and can be directly read out by the user. This enables point-of-care testing with results available during a patient visit. The inventions disclosed in this copending application are particularly advantageous for the diagnosis of conjunctivitis.

In a method of the invention, the sample to be analyzed is applied to a chromatographic carrier. The carrier can be made of one single chromatographic material, or preferably several capillary active materials made of the same or different materials and fixed on a carrier backing. These materials are in close contact with each other so as to form a transport path along which a liquid driven by capillary forces flows from an application zone, passing a reagent zone, towards one or more detection zones and optionally a waste zone at the other end of the carrier. In other embodiments, the liquid passes the reagent zone prior to flowing into the sample application zone. In an especially preferred embodiment, the carrier is a chromatographic test strip. In other preferred embodiments, the sample may be applied to a sample compressor in a different plane from the chromatographic test strip, and then transferred to the chromatographic test strip by the sample compressor.

In some embodiments, the sample is directly applied to the carrier by dipping the carrier's application zone into the sample. Alternatively, application of the sample to the carrier may be carried out by collecting the sample with a dry or wetted wiping element from which the sample can be transferred, optionally after moistening, to the carrier's application zone. Usually, the wiping element is sterile and may be dry or pretreated with a fluid before the collection step. Materials suitable for wiping elements according to the invention may comprise synthetic materials, woven fabrics or fibrous webs. Some examples of such wiping elements are described in German Patents DE 44 39 429 and DE 196 22 503, which are hereby incorporated by reference. In other embodiments, the sample may be collected by a collection receptacle, such as a pipette, and transferred directly to the carrier.

Depending on the type of detection method, different reagents are present in the carrier's reagent zone, which, in some embodiments, is preferably located between the application zone and the detection zone or, in other embodiments, is preferably located before the application zone. In yet other embodiments, the reagents may be on a sample compressor separate from and in a different plane than the carrier including the detection zone.

In a sandwich immunoassay, it is preferred to have a labeled, non-immobilized reagent in the reagent zone that is specific to each bacterial and viral marker that is being detected. Thus, when a viral or bacterial marker present in the sample contacts the corresponding labeled viral or bacterial reagent present in the reagent zone, a labeled complex is formed between the marker and the corresponding labeled reagent. The labeled complex in turn is capable of forming a further complex with an immobilized viral or bacterial marker binding partner at a test line in the detection zone. In a competitive immunoassay, the reagent zone preferably contains a labeled, non-immobilized marker analogue which competes with the marker for the immobilized marker binding partner in the detection zone. The marker binding partners in the reagent zone and in the detection zone are preferably monoclonal, polyclonal or recombinant antibodies or fragments of antibodies capable of specific binding to the corresponding marker.

In a preferred embodiment, the present invention provides for the reduction of interfering substances that might be present in the sample to be tested. Since an interfering substance, e.g. a human anti-mouse antibody (HAMA), may also be capable of forming a complex with the labeled, non-immobilized reagent of the reagent zone and the immobilized binding partner of the detection zone, thus indicating a positive test result in the immunoassay, the carrier may further include at least one capturing zone. Each capturing zone contains an immobilized capturing reagent specifically binding to a certain interfering substance, thereby immobilizing the interfering substance in the capturing zone. As the capturing zone is separated from the detection zone by space, and the sample starts to migrate over the reagent zone and the capturing zone before reaching the carrier's detection zone, the method allows a separation of the interfering substance or substances from the analyte or analytes of interest. Preferably, the capturing zone is located between the reagent zone and the detection zone. However, the capturing zone may also be located between the application zone and the reagent zone.

Detection of the marker may be achieved in the detection zone. The binding molecule immobilizes the labeled complex or the labeled marker-analogue by immune reaction or other reaction in the detection zone, thus building up a visible test line in the detection zone during the process. Preferably, the label is an optically detectable label. Forming a complex at the test line concentrates and immobilizes the label and the test line becomes visible for the naked eye, indicating a positive test result. Particularly preferred are direct labels, and more particularly gold labels which can be best recognized by the naked eye. Additionally, an electronic read out device (e.g. on the basis of a photometrical, acoustic, impedimetrical, potentiometric and/or amperometric transducer) can be used to obtain more precise results and a semi-quantification of the analyte. Other labels may be latex, fluorophores or phosphorophores.

In one embodiment, the sensitivity of visually read lateral flow immunoassay tests is enhanced by adding a small quantity of fluorescing dye or fluorescing latex bead conjugates to the initial conjugate material. When the visible spectrum test line is visibly present, the test result is observed and recorded. However, in the case of weak positives that do not give rise to a distinct visual test line, a light of an appropriate spectrum, such as a UV spectrum, is cast on the test line to excite and fluorescent the fluorescing latex beads which are bound in the test line to enhance the visible color at the test line.

In a preferred embodiment, the reagents are configured such that the visible test line corresponding to the presence of the viral marker will be separate from the test line corresponding to the presence of the bacterial marker. Therefore, it can be readily determined whether the sample contained bacterial or viral markers (or both) simply by the location of the development of the test lines in the detection zone. In another preferred embodiment, the reagents may be chosen such that differently colored test lines are developed. That is, the presence of a viral marker will cause the development of a differently colored line than that developed by the presence of a bacterial marker. For example, the label corresponding to the reagent recognizing the viral marker may be red, whereas the label corresponding to the reagent recognizing the bacterial marker may be green. Differently colored labels that may be attached to the non-immobilized reagents are well known. Some examples include, but are not limited to, colloidal gold, colloidal selenium, colloidal carbon, latex beads, paramagnetic beads, fluorescent and chemiluminescent labels and mixtures thereof.

Figure 4A:
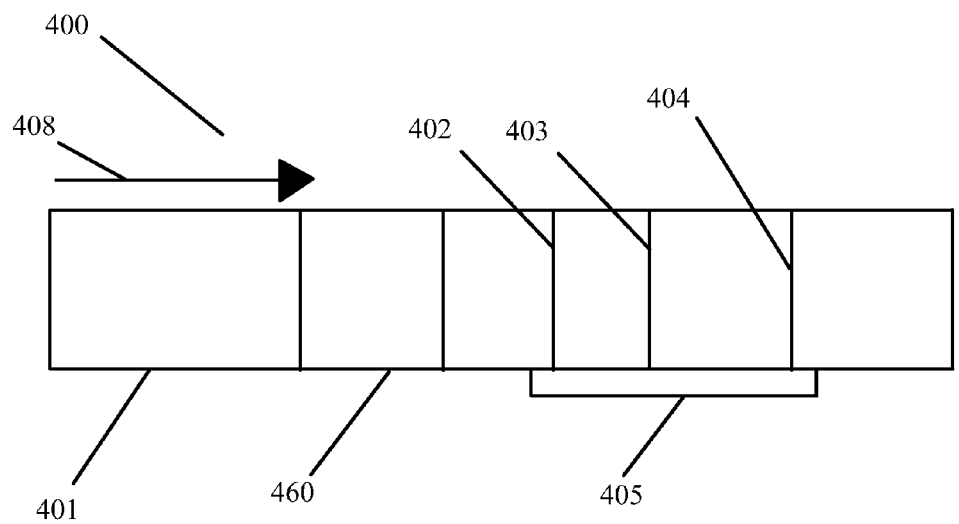
FIG. 4A shows a device with a test line corresponding to the presence of a viral marker and a second, separate test line that detects the presence of a bacterial marker in an embodiment of the present invention.
Figure 4B:
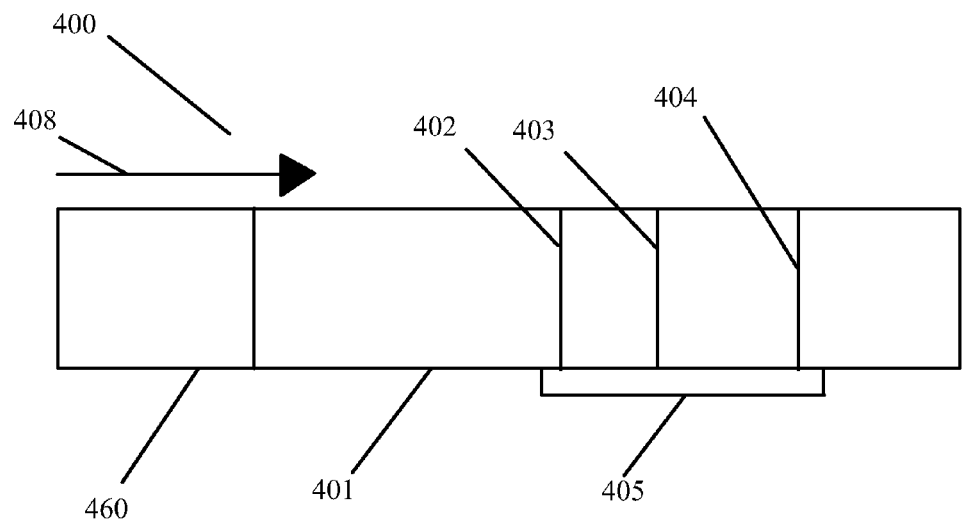
FIG. 4B shows a device with a test line corresponding to the presence of a viral marker and a second, separate test line that detects the presence of a bacterial marker in another embodiment of the present invention.

FIGS. 4A and 4B show a chromatographic test strip (400) with a test line (402) corresponding to the presence of a viral marker and a second, separate test line (403) that detects the presence of a bacterial marker. The sample is applied to the application zone (401) of the chromatographic test strip (400). As shown in FIG. 4A, the sample then passes a reagent zone (460) containing at least one labeled viral binding partner and at least one labeled bacterial binding partner that is eluted by and then able to migrate with a sample transport liquid (e.g. a buffer solution). Alternatively, as shown in FIG. 4B, the reagent zone (460) is located upstream of the sample application zone (401) such that the labeled binding partners in the reagent zone are eluted by the sample transport liquid and travel to the sample. The labeled viral binding partner is capable of specifically binding to a viral marker of interest to form a complex which in turn is capable of specifically binding to another specific reagent or binding partner in the detection zone. The labeled bacterial binding partner is capable of specifically binding to a bacterial marker of interest to form a complex which in turn is capable of specifically binding to another specific reagent or binding partner in the detection zone. Although not shown in these Figures, an absorbent pad, as well as other known lateral flow immunoassay components including, but not limited to, a waste zone, a carrier backing, a housing, and an opening in the housing for result read out, may optionally also be a component of the test strip (400) in these embodiments.

The test strip (400) also includes a detection zone (405) containing at least one first section for detection of a viral marker, e.g. a test line (402), including an immobilized specific binding partner, complementary to the viral reagent complex formed by the viral marker and its labeled binding partner. Thus, at the test line (402), detection zone binding partners trap the labeled viral binding partners from the reagent zone (460) along with their bound viral markers. This localization of the viral marker with its labeled binding partners gives rise to an indication at the test line (402). At the test line (402), the presence of the viral marker is determined by qualitative and/or quantitative readout of the test line (402) indication resulting from the accumulation of labeled binding partners.

The detection zone (405) also includes at least one second section for detection of a bacterial marker, e.g. a test line (403), including an immobilized specific binding partner, complementary to the bacterial reagent complex formed by the bacterial marker and its labeled binding partner. Thus, at the test line (403), detection zone binding partners trap the labeled bacterial binding partners from the reagent zone (460) along with their bound bacterial markers. This localization of the bacterial marker with its labeled binding partners gives rise to an indication at the test line (403). At the test line (403), the presence of the bacterial marker is determined by qualitative and/or quantitative readout of the test line (403) indication resulting from the accumulation of labeled binding partners. While test line (402) is upstream of test line (403) relative to the direction of flow (408) in the figures, in alternative embodiments, test line (403) is upstream of test line (402). In still other embodiments, test lines (402) and (403) are located in the same location on the test strip.

Optionally, the detection zone (405) may contain further test lines to detect other viral and/or bacterial markers, as well as a control line (404). The control line (404) indicates that the labeled specific binding partner traveled through the length of the assay, even though it may not have bound any viral or bacterial markers, thus confirming proper operation of the assay. As shown in FIGS. 4A through 4B, the control zone (404) is preferably downstream of the test lines (402) and (403). However, in other embodiments, the control zone (404) may be located upstream of either or both of the test lines (402) and (403).

In a preferred embodiment, the control line (404) includes an antibody or other recombinant protein which binds to a component of the elution medium or other composition being used in the test. In embodiments where nucleic acids are the targets, the control line (404) preferably includes a nucleic acid complementary to the labeled nucleic acid being used as a binding partner for the target nucleic acid.

Although only one test line is shown in the figures for each of the viral and bacterial markers, multiple test lines for both or either of the viral and bacterial markers may be used within the spirit of the invention. In some embodiments where there are multiple bacterial and/or viral targets, the presence of each target preferably corresponds to a separate test line (402) or (403). In other embodiments, both the bacterial marker and the viral marker are detected on a single test line. In these embodiments, the presence of both a bacterial marker and a viral marker on the same test line has different characteristics than the presence of either a bacterial or viral marker alone. For example, the presence of both a bacterial marker and a viral marker on the same test line may be visually indicated by a different color than the presence of either a bacterial marker or a viral marker alone.

Fresh whole blood samples of patients showing symptoms of viral infections (flu like symptoms and fever of >100.5° F.) were tested to determine what levels of MxA in the blood could be detected with the lateral flow tests described herein. The lateral flow assays used in these experiments had a similar configuration as the device shown in FIG. 4B described above, without a second test line for the presence of a bacterial marker. More specifically, the test strip included a reagent zone upstream of a sample application zone. The reagent zone included mobilizable antibodies to MxA (Kyowa Hakko Kirin Co., Ltd., Tokyo, Japan) labeled with colloidal gold. The test strip also included a test line in a detection zone. The test line included an immobilized antibody for MxA (Kyowa Hakko Kirin Co., Ltd., Tokyo, Japan). The control line in the detection zone included rabbit anti-chicken antibody plus rabbit Ig (for an extra stabilizing effect), which binds to mobilized chicken IgY labeled with blue latex beads.

The whole blood samples were collected with EDTA as the anticoagulant. In these tests, the amount of MxA protein in the blood samples was determined using an MxA Protein ELISA Test kit (Kyowa Hakko Kirin Co., Ltd., Tokyo, Japan). The blood was lysed 1:10 with lysing solution provided in the kit, prior to being applied to the test strip. 100 µl of lysed blood was tested in the ELISA test. 10 µl of lysed blood was used as the sample in the MxA lateral flow test.

The lysed blood samples were applied to the application zone of the test strip. The labeled MxA antibodies in the reagent were eluted by the sample transport liquid and travelled to the blood samples. At the test line, the immobilized MxA antibody trapped any labeled MxA antibody from the reagent zone bound to MxA. This localization of the MxA with its labeled antibody gave rise to a red visual indication at the test line if there was a sufficient concentration of MxA.

TABLE 1

| Calibrator Concentration (ng/ml) | OD | Lateral Flow MxA Test |
|---|---|---|
| 24 | 2.223 | + |
| 12 | 1.259 | Shadow |
| 6 | 0.700 | Not tested |
| 3 | 0.391 | Not tested |
| 1.5 | 0.220 | Not tested |
| .75 | 0.140 | Not tested |
| 0.38 | 0.102 | Not tested |

Table 1 shows the MxA ELISA kit standards run per the test instructions. As shown in Table 1, an MxA concentration of 24 ng/ml produced a positive result in the lateral flow test. The kit standard was used to generate the standard curve from which the MxA concentrations were determined Table 2 shows the results of clinical fresh whole blood samples of patients showing symptoms of viral infections (flu like symptoms and fever of >100.5° F.)).

TABLE 2

| Sample | OD | Concentration (ng/ml) | Concentration x dilution (10x) (ng/ml) | Lateral Flow MxA Test |
|---|---|---|---|---|
| A | 0.008 | 0 | 0 | − |
| B | 0.123 | 0.591 | 5.911 | − |
| C | 1.125 | 10.489 | 104.894 | + |
| D | 0.111 | 0.487 | 4.872 | − |
| E | 0.068 | 0.121 | 1.211 | − |
| F | 0.300 | 2.177 | 21.77 | + |
| G | 0.027 | 0 | 0 | − |

The OD (optical density) values were used in combination with the standard curve from the kit's standard in order to determine the MxA concentration in the samples. The concentration (ng/ml) column was the concentration as diluted with the lysing agent. The concentration×dilution (10×) (ng/ml) column was the actual concentration in the whole blood sample. As shown in the table, the lateral flow test produced a positive result for MxA in samples C and F, which had approximately 105 ng/ml of MxA and approximately 22 ng/ml of MxA, respectively, in the samples.

Table 3 shows the results of frozen whole blood samples from normal individuals from the Tennessee blood bank. None of the blood samples had any discernible amounts of MxA, and all of them were negative in the lateral flow test.

TABLE 3

| Sample | OD | CONCEN-TRATION (ng/ml) | CONCEN-TRATION X DILUTION (10X)(ng/ml) | Lateral Flow MxA Test |
|---|---|---|---|---|
| 1 | 0.003 | 0 | 0 | − |
| 2 | 0.014 | 0 | 0 | − |
| 3 | 0.008 | 0 | 0 | − |
| 4 | 0.035 | 0 | 0 | − |
| 5 | 0.011 | 0 | 0 | − |
| 6 | 0.007 | 0 | 0 | − |
| 7 | (0.017) | 0 | 0 | − |
| 8 | (0.006) | 0 | 0 | − |
| 9 | 0.028 | 0 | 0 | − |
| 10 | 0.012 | 0 | 0 | − |
| 11 | 0.028 | 0 | 0 | − |
| 12 | 0.02 | 0 | 0 | − |
| 13 | 0.044 | 0 | 0 | − |
| 14 | 0.023 | 0 | 0 | − |
| 15 | 0.032 | 0 | 0 | − |

TABLE 3-continued

| Sample | OD | CONCEN-TRATION (ng/ml) | CONCEN-TRATION X DILUTION (10X)(ng/ml) | Lateral Flow MxA Test |
|---|---|---|---|---|
| 16 | 0.02 | 0 | 0 | – |
| 17 | 0.032 | 0 | 0 | – |
| 18 | 0.009 | 0 | 0 | – |
| 19 | 0.035 | 0 | 0 | – |
| 20 | 0.022 | 0 | 0 | – |
| 21 | 0.017 | 0 | 0 | – |
| 22 | 0.188 | 1.163 | 11.631 | – |
| 23 | 0.014 | 0 | 0 | – |
| 24 | 0.005 | 0 | 0 | – |
| 25 | 0.039 | 0 | 0 | – |

Table 4 shows freshly frozen whole blood samples from BioReclamation (BioReclamation, Hicksville, N.Y.) of patients showing apparent symptoms of viral infections (flu like symptoms and fever of >100.5° F.)). None of these patients had ODs that corresponded to MxA levels higher than approximately 8 ng/ml. These samples were all negative in the lateral flow test.

TABLE 4

| Sample | OD | Concentration (ng/ml) | Concentration x dilution (10x) (ng/ml) | Lateral Flow MxA Test |
|---|---|---|---|---|
| 26 | 0.029 | 0 | 0 | – |
| 27 | 0.026 | 0 | 0 | – |
| 28 | 0.018 | 0 | 0 | – |
| 29 | 0.146 | 0.792 | 7.92 | – |
| 30 | 0.004 | 0 | 0 | – |
| 31 | 0.128 | 0.635 | 6.35 | – |

The results of these tests indicate that the lateral flow tests described herein can detect MxA levels at least as low as approximately 20 ng/ml in a 10 μl sample (diluted 1:10).

One example of a rapid screening test for distinguishing viral and bacterial infection is shown in FIG. 1. As discussed above, MxA is a diagnostic marker for viral infection, while CRP is a diagnostic marker for bacterial infection. In this example, a blue line ("control line" in A-D of the Figure) represents the control. A green line represents a C-reactive protein (CRP) level >15 mg/L ("CRP test" in A-D of the figure). A red line represents an MxA level >20 ng/ml ("MxA test" in A-D of the figure). A positive result for the MxA protein, with a negative result for the CRP protein indicates only a viral infection (Visual Test Result A). A positive result for the (CRP) with a negative result for the MxA protein indicates only a bacterial infection (Visual Test Result B). A positive result for both MxA and CRP indicates co-infection (infection with both a bacteria and a virus) (Visual Test Result C). No bacterial or viral infection is indicated by a negative result for both MxA and CRP (Visual Test Result D). While particular color lines are discussed in this example, other colors, or the same colors at different locations on the test strip to indicate viral or bacterial markers, are within the spirit of the present invention.

When development of different colored lines is utilized, the lines may or may not be separated by space. In the latter instance, the labels are chosen such that the color seen when both markers are present is different from the colors seen when the individual markers are present. For example, the presence of the viral marker may be indicated by a red line; the presence of the bacterial marker by a blue line; and the presence of both by a purple line (combined red and blue).

The use of two colors to distinguish acute and chronic infection is shown in FIG. 2. In the first cassette, only IgM antibodies are present, which indicates an acute infection. In this cassette, the test line is red. In the second cassette, the test line is blue because the immunoglobulins are IgG. The third cassette shows an intermediate case, where both IgM and IgG antibodies are present. Consequently, the test line is purple. While this example is shown to test for IgMs and IgGs, the same concept is alternatively used with a single line which detects both viral and bacterial markers for infection.

In another preferred embodiment, the test strip may also include a control section which indicates the functionality of the test strip. FIG. 1 shows a control line. FIG. 2 shows an example where there is a control section for all three cassettes. If present, the control section can be designed to convey a signal to the user that the device has worked. For example, the control section may contain a reagent (e.g., an antibody) that will bind to the labeled reagents from the reagent zone. In one preferred embodiment, rabbit anti chicken is used as the control line and chicken IgY conjugated to a label, for example blue latex beads, is the control conjugate. Alternatively, the control section may contain an anhydrous reagent that, when moistened, produces a color change or color formation, e.g. anhydrous copper sulphate which will turn blue when moistened by an aqueous sample. As a further alternative, the control section could contain immobilized viral and bacterial markers which will react with excess labeled reagent from the reagent zone. The control section may be located upstream or downstream from the detection zone. A positive control indicator tells the user that the sample has permeated the required distance through the test device.

Figure 3:
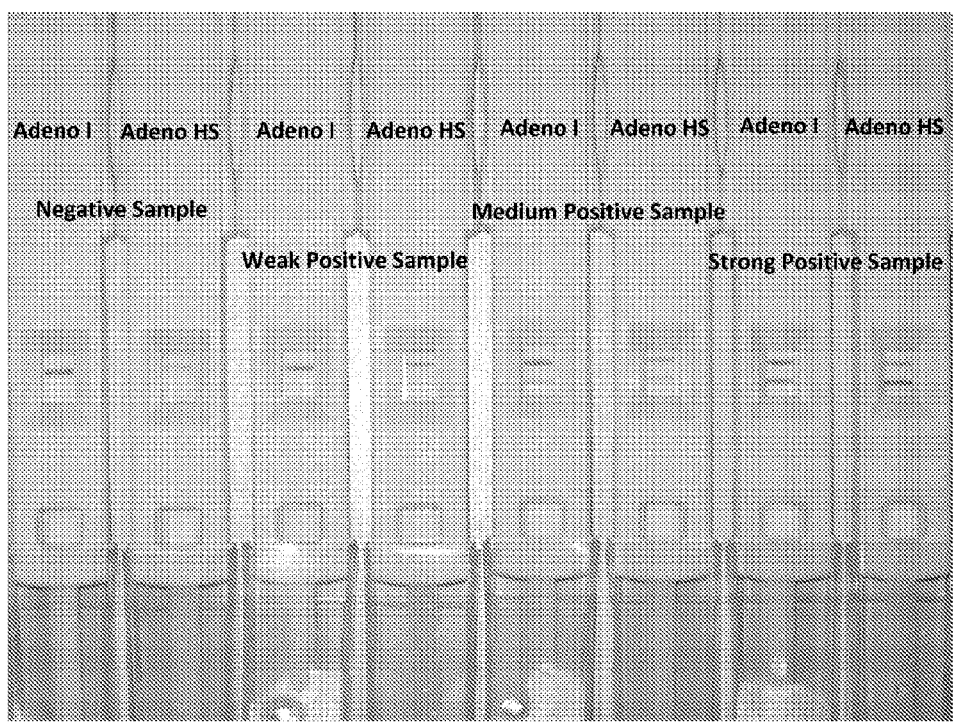
FIG. 3 shows a comparison of a two line detector, where both lines are the same color, and an extra sensitive two line detector, where the two lines are different colors.

FIG. 3 compares two test strips, the "Adeno 1" and the "Adeno HS", which both include control lines. In the Adeno 1, both the control (upper line on each cassette) and test (lower line on each cassette) lines are red. In the Adeno HS, the control line is blue and the test line is red. In embodiments where the control line is a different color than the test line, it is easier to distinguish between the two lines, and to ensure that the test is working.

In some preferred embodiments, the devices and methods of the present invention include a lysis zone to help differentiate viral and bacterial infections. In these embodiments, the sample that has been collected is not lysed prior to collection and transfer to the sample analysis device. This decreases the number of steps needed to collect and prepare the sample for analysis. One situation where a lysis agent improves assay efficiency is in assaying for the presence of MxA. As discussed herein, the presence of this protein can help to distinguish between bacterial and viral infection in febrile children. In situ lysis using a combination of 1% to 6% weight/volume CHAPS and 0.5% to 2% weight/volume NP40 as the lysis agent improves detection of MxA in fresh or frozen whole blood.

In the embodiments utilizing a lysis agent, following sample loading, the sample traveling with the transport liquid (buffer) will encounter the lysis agent. The lysis agent will have preferably been pre-loaded onto the test strip and is eluted by the transport liquid. In some preferred embodiments the lysis agent has been dried into the test strip. Alternatively, the lysis agent may be pre-dried by freeze drying or lyophilizing and then pre-loaded into the test strip. In other embodiments, the lysis agent may be absorbed, adsorbed, embedded or trapped on the test strip. The initially dried lysis agent is preferably localized between the sample application zone and a reagent zone. In embodiments where the reagent zone is upstream of the sample application zone, the lysis zone is downstream of the sample application zone. The lysing agent is preferably soluble in the sample transport liquid, and the lysing agent is solubilized and activated upon contact with the sample transport liquid. The sample transport liquid then contains both lysing agent in solution or suspension and sample components in suspension. Any lysis-susceptible components in a sample, then being exposed in suspension to the lysing agent, are themselves lysed in situ. The running buffer then carries the analyte, including any lysis-freed components, to the detection zone.

The location where the lysis agent is pre-loaded and dried can be varied as needed. In order to maximize the time that the sample has to interact with the lysis agent as well as to minimize the amount of lysis agent reaching the detection zone, the dried, absorbed, adsorbed, embedded, or trapped lysis agent may be located in or just downstream of the sample application zone. Or, in order to minimize the distance along which the lysis product must travel before reaching the reagent zone, the dried lysis agent may be located closer to the reagent zone. In other embodiments, the lysis agent may be included in the running buffer.

The concentration of lysis agent pre-loaded onto a test strip is preferably between 0.001% and 5% weight/volume. The volume to be pre-loaded depends on where the lysis agent is pre-loaded. Appropriate ranges are 1 to 10 microliters when pre-loaded into the sample collector fleece (the sample application zone) or 5 to 50 microliters when pre-loaded into the absorbent pad or into other locations within the test strip. Ideally, the amount pre-loaded should be approximately 3 microliters pre-loaded into the sample collector fleece or approximately 10 microliters pre-loaded into the absorbent pad or into other locations within the test strip.

Selection of a specific lysing environment and agent will depend on the viral and bacterial markers and the assay. The pH and ionic strength are key to the lysing environment. As to pH established by the lysis agent, a pH below 4.0 tends to precipitate materials, especially proteins. Higher pH, above approximately 10.0, tends to lyse materials such as proteins and cells walls. Therefore, a pH of approximately 10.0 or above is preferable for many applications. Alternatively, lower pH may be preferred for nucleic acid targets.

As to ionic strength established by the lysis agent, both the high and low ionic strength may be used to lyse. For example, a lower ionic strength (hypotonic) tends to break up erythrocytes. For example, water by itself can lyse erythrocytes. Higher ionic strength environments may be used to rupture certain cell walls and membranes.

As to specific lysis agents, they may be grouped and selected based on their properties: salts, amphoteric and cationic agents, ionic and non-ionic detergents. The salt, Ammonium Chloride ($NH_4Cl$), lyses erythrocytes. Other salts, including, but not limited to, high concentrations of Sodium Chloride (NaCl) and Potassium Chloride (KCl), may rupture certain cell walls and membranes. Other lysis agents are amphoteric agents including, but not limited to, Lyso PC, CHAPS, and Zwittergent. Alternatively, cationic agents including, but not limited to, C16 TAB and Benzalkonium Chloride may be used as a lysis agent. Both ionic and non-ionic detergents are often used to break or lyse the cell wall or cell membrane components such as lipoproteins and glycoproteins. Common ionic detergents include, but are not limited to, SDS, Cholate, and Deoxycholate. Ionic detergents are good solubilizing agents. Antibodies retain their activity in 0.1% SDS or less. Common non-ionic detergents include, but are not limited to, Octylglucoside, Digitonin, C12E8, Lubrol, Triton X-100, Noniodet P-40, Tween 20, and Tween 80. Non-ionic and mild ionic detergents are weaker denaturants and often are used to solubilize membrane proteins such as viral surface proteins. Additional lysis agents include, but are not limited to, urea and enzymes. Combinations of different lysis agents may be used to optimize the lysing environment.

Surfactants are generally wetting agents and lower the surface tension of a liquid. This then allows easier spreading by lowering the interfacial tension between liquids. So, surfactants can interfere with the natural binding of antigen and antibody or ligand and receptors. The concentrations are, therefore, experimentally chosen for each class of lysis agent. Once lysis occurs, it is important that the desired binding reactions not be hindered. Generally, 0.001% lysis agent concentration is considered the lower limit, and the upper limit is approximately 1%. There is an additive or synergistic effect when combinations of lysis agents are used. This expands the working range of concentration to run from approximately 0.001% to 1%. Finally, some undesirable non-specific binding may be prevented at a Tween 20 concentration of 5%. In all cases, the total amount of lysis agent pre-loaded onto all locations of an individual test strip must be sufficient to lyse barriers to immunodetection, permitting practical operation of the test strip.

The lysis agent itself should not interfere with any other assay detector or indicator agents and thus does not interfere with any other assay interactions and reactions to such an extent as to prevent practical operation of the assay. A lysis agent should have sufficient shelf life to allow manufacture, distribution and storage before use of a test strip in point-of-care testing.

In preferred embodiments where MxA is the viral marker, in situ lysis using a combination of 1% to 6% weight/volume CHAPS and 0.5% to 2% weight/volume NP40 as the lysis agent is preferably used. As a more specific example, 2 microliters of 100 mM HEPES buffer (pH 8.0) containing 5% CHAPS and 2% NP-40 with 150 mM Sodium Chloride, 0.1% BSA, and 0.1% Sodium Azide (all percentages weight/volume) are dried onto a lysis zone of a test strip.

In a preferred embodiment, as shown in FIGS. 5A through 5D, the sample is applied to the application zone (201) on a chromatographic test strip (200). The sample passes a lysis zone (250), where a lysis agent will have preferably been pre-loaded onto the test strip and is eluted by the transport liquid. The lysis agent lyses any lysis-susceptible components in the sample in situ.

The chromatographic test strip contains a sample application zone (201), a lysis zone (250) containing a lysis agent, and a reagent zone (260) containing at least one labeled binding partner that binds to a viral marker and at least one labeled binding partner that binds to a bacterial marker that are eluted by and then able to migrate with a sample transport liquid (e.g. a buffer solution). While the reagent zone (260) is shown downstream of the sample application zone in these figures, in alternative embodiments, the reagent zone (260) could be upstream of the sample application zone (see FIG. 4B), as long as the reagents encounter the sample at some point after the sample reaches the lysis zone and is effectively lysed. The labeled binding partners are capable of specifically binding to a viral or bacterial marker of interest to form a complex which in turn is capable of specifically binding to another specific reagent or binding partner in the detection zone. Although not shown in these Figures, an absorbent pad, as well as other known lateral flow immunoassay components including, but not limited to, a waste zone, a carrier backing, a housing, and an opening in the housing for result read out, may optionally also be a component of the test strip (200) in these embodiments.

In a preferred embodiment, the lysis agent is localized in the lysis zone (250) between the sample application zone (201) and the reagent zone (260). The lysis agent is preferably soluble or miscible in the sample transport liquid, and the lysis agent is solubilized and activated upon contact with the sample transport liquid. The sample transport liquid then contains both lysis agent in solution or suspension and sample components in suspension. Any lysis-susceptible components in a sample, then being exposed in suspension to the lysis agent, are themselves lysed in situ. The running buffer then carries the sample, including any lysis-freed components, to the detection zone (205).

Figure 5A:
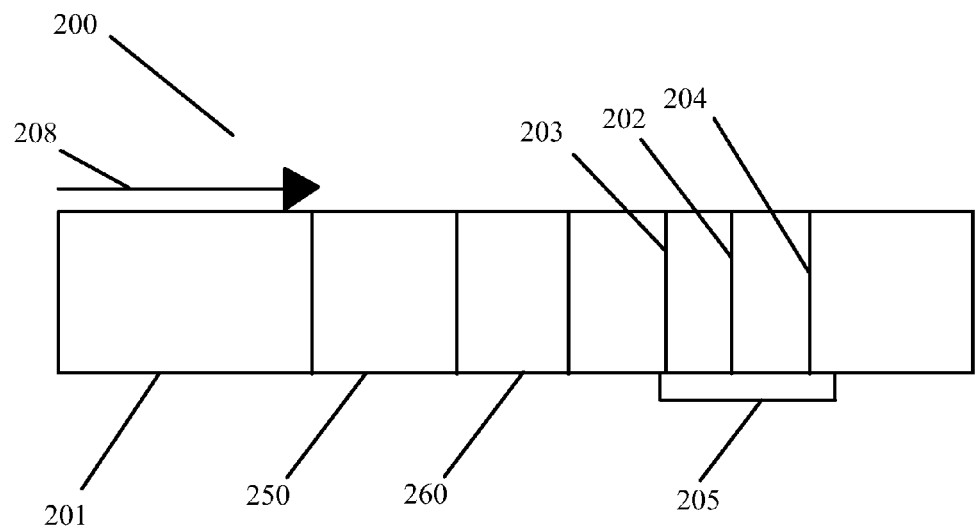
FIG. 5A shows a sample analysis device including a lysis zone located between a sample application zone and a reagent zone in an embodiment of the present invention.
Figure 5B:
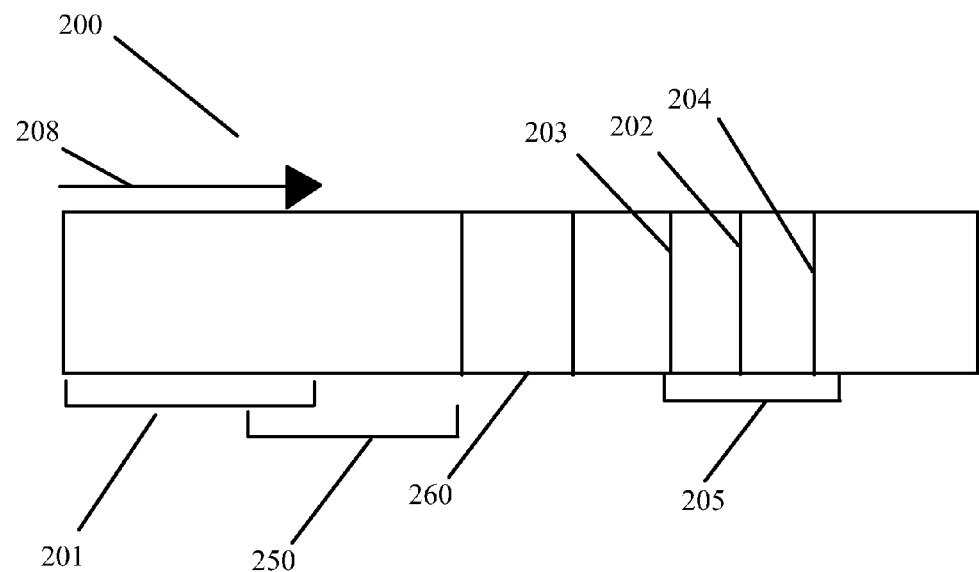
FIG. 5B shows a sample analysis device including a lysis zone overlapping a sample application zone in an embodiment of the present invention.

The lysis zone (250) is preferably located between the sample application zone (201) and the reagent zone (260), as shown in FIG. 5A. In other embodiments, the lysis zone (250) overlaps the sample application zone (201), the reagent zone (260) or both the sample application zone (201) and the reagent zone (260) as shown in FIGS. 5B, 5C, and 5D, respectively. Note that the figures are schematic, and are not drawn to scale. The amount of overlap between the different zones (as shown in FIGS. 5B through 5D) may be highly variable.

The test strip (200) also includes a detection zone (205) containing a first section for detection of at least one bacterial marker, e.g. a test line (203), including an immobilized specific binding partner, complementary to the bacterial conjugate formed by the bacterial marker and its labeled binding partner. Thus, at the test line (203), detection zone binding partners trap the bacterial labeled binding partners from the reagent zone (260) along with their bound bacterial markers. This localization of the bacterial markers with their labeled binding partners gives rise to an indication at the test line (203). At the test line (203), the presence of a bacterial marker is determined by qualitative and/or quantitative readout of the test line (203) indication resulting from the accumulation of labeled binding partners.

The detection zone (205) also includes a second section for detection of at least one viral marker, e.g. a test line (202), including an immobilized specific binding partner, complementary to the viral conjugate formed by the viral marker and its labeled binding partner. Thus, at the test line (202), detection zone binding partners trap the viral labeled binding partners from the reagent zone (260) along with their bound viral markers. This localization of the viral markers with their labeled binding partners gives rise to an indication at the test line (202). At the test line (202), the presence of a viral marker is determined by qualitative and/or quantitative readout of the test line (202) indication resulting from the accumulation of labeled binding partners. While test line (203) is upstream of test line (202) relative to the direction of flow (208) in the figures, in alternative embodiments, test line (202) is upstream of test line (203). In still other embodiments, test lines (202) and (203) are located in the same location on the test strip.

Optionally, the detection zone (205) may contain further test lines to detect other bacterial and/or viral markers, as well as a control line (204). The control line (204) indicates that the labeled specific binding partner traveled through the length of the assay, even though it may not have bound any markers, thus confirming proper operation of the assay. As shown in FIGS. 5A through 5D, the control zone (204) is preferably downstream of the test lines (203) and (202). However, in other embodiments, the control zone (204) may be located upstream of either or both of the test lines (203) and (202).

In a preferred embodiment, the control line (204) includes an antibody or other recombinant protein which binds to a component of the elution medium or other composition being used in the test. In embodiments where nucleic acids are the targets, the control line (204) preferably includes a nucleic acid complementary to the labeled nucleic acid being used as a binding partner for the target nucleic acid.

Although only one test line is shown in the figures, multiple test lines are within the spirit of the invention. In some embodiments where there are multiple targets, the presence of each target preferably corresponds to a separate test line (202). In other embodiments where there are multiple targets, the presence of multiple targets may be indicated on the same test line such that the presence of more than one target has different characteristics than the presence of a single target. For example, the presence of multiple targets on the same test line may be visually indicated by a different color than the presence of each of the targets alone.

In other embodiments, it is possible to have one or more mild lysis agents in the running buffer itself. In these embodiments, there is no adverse effect on the reagent zone which will be downstream and the sample can either be upstream or downstream of the reagent zone. A lysing enzyme in the running buffer can "target" its substrate and cut it to open up the cell membrane or cell wall. As an example, penicillin can excise or "punch a hole" in a susceptible bacteria. In other embodiments, when the lysis agent is applied to the sample collection material, then the reagent zone may be upstream of the sample application zone.

As an example, one or more lysis agents are dried onto the sample application zone of a lateral flow strip. On a per strip basis, the lysis agent is made of approximately 2 microliters of 100 mM HEPES buffer (pH 8.0) containing 5% CHAPS and 2% NP-40 with 150 mM Sodium Chloride, 0.1% BSA, and 0.1% Sodium Azide (all percentages weight/volume). Up to 10 microliters of whole blood are then added to the sample application zone to be lysed in situ. MxA protein is released from inside white blood cells to react with an MxA monoclonal antibody on a visual tag (colloidal gold or visible latex beads). This complex traverses with a running buffer containing Triton X-100 and is captured by MxA monoclonal antibodies immobilized at the test line of the nitrocellulose membrane. This binding at the test line gives rise to a visible indication.

Sample Analysis Device with Bimodal Dual Test Strips

MxA is a derivative of interferon alpha/beta cells that becomes elevated in the presence of viral infections but is not specific for a particular type of virus. MxA protein expression in peripheral blood is a sensitive and specific marker for viral infection.

MxA inhibits the replication of a wide range of viruses. MxA has a low basal concentration [less than 50 ng/ml] and a fast induction [1-2 hours]. It peaks at 16 hours and remains elevated in the presence of elevated interferon. MxA also has a long half-life [2.3 days] and constant titres in presence of interferonemia. Viral infections elevate MxA levels while only having a modest increase in CRP levels.

In one prospective clinical trial using ELISA (Towbin H et al. J Interferon Res 1992; 12:67-74, herein incorporated by reference), the trial enrolled 87 normal healthy adults. The MxA levels were measured to be <5 ng/ml in 66% of the adults, between 5-50 ng/ml in 29% of the adults, and above 50 ng/ml in 5% of the adults.

Another prospective clinical trial using ELISA (Chieux V et al., J Virol Methods 1998; 70:183-191, herein incorporated by reference) enrolled 174 children. 45 of these children had acute fever (respiratory infection and/or gastroenteritis) and there were 30 age-matched controls. The MxA values were 7 ng/ml±7 ng/ml in the 30 age-matched controls. The MxA values were 10 ng/ml±6 ng/ml in 13 confirmed bacterial infections.

Another prospective clinical trial using ELISA enrolled 60 patients (Kawamura M et al. J Clin Lab Anal 2012; 26:174-183, herein incorporated by reference). 42 of the patients had acute fever (respiratory infection and/or gastroenteritis) and there were 18 age matched controls. The median MxA value was 110.0 ng/ml in 31 confirmed viral infections. The median MxA value was 10.6 ng/ml in 11 confirmed bacterial infections. The median MxA value was 2.0 ng/ml in the 18 age matched controls. The ELISA test had a sensitivity of 87.1% and a specificity of 90.9% for differentiating viral from bacterial infection, but only tested MxA values to make this determination. Patients with viral infection were sharply distinguished from the healthy controls with 100% sensitivity and specificity. A cut-off of 36.7 ng/ml MxA was used to determine viral infection by ELISA in this study.

Another prospective clinical trial using ELISA enrolled 174 children (Nakabayashi M et al., Pediatr Res 2006; 60:770-774, herein incorporated by reference, data corrected for recalibrated ELISA standard). 122 of the children had acute fever (respiratory infection and/or gastroenteritis) and there were 52 age-matched controls. The mean MxA value was 123.7 ng/ml±83.0 ng/ml in 95 confirmed viral infections. The mean MxA value was 12.3 ng/ml±10.0 ng/ml in 27 confirmed bacterial infections. The mean MxA value was 14.5 ng/ml±11.0 ng/ml in the 52 age matched controls. The test showed a 92.6% specificity and a positive likelihood ratio of 13.1 for accurately identifying viral infection. A cut-off of 36.7 ng/ml MxA was used to determine viral infection by ELISA in this study.

The cut-off in the ELISA test is artificial and is picked to discriminate between positive and negative. Therefore, it is preferable to routinely assign 10% CV from this cut-off. In a point of care test, 100% of the people can visibly see the test line at >40 ng/ml, but some people can see a positive result at lower levels.

CRP becomes elevated in the presence of bacterial infections but is not specific for a particular type of bacteria. CRP is a nonspecific indicator for the presence of acute inflammation and is elevated in the presence of bacterial infections. CRP is an acute-phase protein synthesized by the liver. IL-6 is the primary mediator of CRP production. Bacterial infection is a potent stimulus of marked CRP elevation. Following antibiotic treatment, CRP levels fall rapidly. Bacterial infections dramatically elevate CRP levels while MxA levels remain low. Bacterial infection is a potent stimulus of CRP with marked elevation in serum CRP levels occurring within a few hours. CRP levels elevate within 4-6 hours after stimulation and peak after 36 hours. The serum concentration of CRP is normally less than 3 mg/L. With severe infection or inflammation, CRP can rise above 500 mg/L.

Pneumonia has elevated serum CRP levels (>10 mg/L). The serum CRP levels are typically greater than 100 mg/L for severe pneumonia. 32% of patients with pneumococcal bacteremia had serum CRP less than 60 mg/L. Serum CRP is not usually elevated above 10 mg/L in viral infection. Invasive Adenovirus and Influenza can raise CRP to 10-80 mg/L. Very infrequently, the CRP levels exceed 60 mg/L in viral infections.

Meta analysis of ten studies (Aouifi et al., Crit care Med. 2000, 28:3171-6; Hatherill et al., Arch Dis Child 1999: 81: 417-21; Muller et al., Crit Care Med. 2000, 28: 977-83; Penel et al., Rev Med Interne 2001:22: 706-714; Rothenberger et al., Clin Chem Lab Med, 1999, 37: 275-9; Schwarz et al., Crit Care Med 2000, 28: 1828-32; Selberg et al., Crit Care Med 2000, 28: 2793-8; Suprin et al., Intensive Care Med 2000, 26: 1232-8; Ugarte et al., Crit Care Med 1999, 27: 498-504; Viallon et al., Intensive Care Med 2000, 26: 1082-8, all herein incorporated by reference) that looked at a single value for serum CRP to be used as a cut-off for bacterial disease resulted in a bimodal outcome. Three of the studies (Aouifi et al., Crit care Med. 2000, 28:3171-6; Penel et al., Rev Med Interne 2001:22: 706-714; Schwarz et al., Crit Care Med 2000, 28: 1828-32) recommended that the CRP cut-off value be set at 6-15 mg/L, while the other seven studies (Hatherill et al., Arch Dis Child 1999: 81: 417-21; Muller et al., Crit Care Med. 2000, 28: 977-83; Rothenberger et al., Clin Chem Lab Med, 1999, 37: 275-9; Selberg et al., Crit Care Med 2000, 28: 2793-8; Suprin et al., Intensive Care Med 2000, 26: 1232-8; Ugarte et al., Crit Care Med 1999, 27: 498-504; Viallon et al., Intensive Care Med 2000, 26: 1082-8) recommended a cut-off of 60-100 mg/L.

In isolation, neither MxA nor CRP alone is sensitive or specific at identifying both viral and bacterial infection. Low cut-off values of CRP show high sensitivity and low specificity for detecting bacterial infection. High cut-off values of CRP show low sensitivity and high specificity for detecting bacterial infection. MxA is specific to identify viral infection, but it is not sensitive for bacterial infection. A multiplexed pattern of results including medical decision points reflected cut-off levels of low CRP, high CRP, and MxA together provide a sensitive and specific way to identify an immune response to a viral and/or bacterial infection.

In one preferred embodiment of a multiplexed lateral flow immunoassay, the fingerstick blood pattern of test results shows a positive result with a serum equivalence to a low CRP level cut-off of approximately 10 mg/L, a serum equivalence to a high CRP level cut-off of approximately 80 mg/L, and a MxA cut-off of approximately 40 ng/ml. These preferred values are shown in Table 5.

TABLE 5

| Biomarker | Location | Fingerstick Cut-off value |
|---|---|---|
| MxA | Intracellular (Peripheral Blood Mononuclear Cells) | 40 ng/ml |
| CRP-low | Extracellular (Serum) | 7 mg/L |
| CRP-high | Extracellular (Serum) | 80 mg/L |

The specificity of the test is further enhanced by restricting the intended use. For example, in preferred embodiments, only certain ages of the patient population are tested (preferably one year of age or older) and/or patients with specific underlying conditions that may lead to confounding factors are preferably not given this test.

A rapid, point-of-care MxA immunoassay was developed and compared to the MxA ELISA in 25 peripheral blood samples from patients with a febrile respiratory illness, as shown in Table 6. Table 7 sorts the same data from lowest to highest amounts of MxA in the ELISA test.

The MxA ELISA cut-off value was 36.7 ng/ml (+/−10% CV=33 ng/ml to 40/5 ng/ml). Patient 19 had a positive result in the MxA rapid point of care test, even though the ELISA results were much less than 40 ng/ml (15 ng/ml). However, the MxA immunoassay demonstrated 100% (9/9) sensitivity and 94% (15/16) specificity.

TABLE 6

| Number | MxA rapid test (40 ng/ml) | MxA EIA |
|---|---|---|
| 1 | Negative | 32.9 |
| 2 | Negative | 5.9 |
| 3 | Negative | 18.8 |
| 4 | Negative | 5.9 |
| 5 | Negative | 19.2 |
| 6 | Negative | 0.0 |
| 7 | Negative | 6.0 |
| 8 | Negative | 4.0 |
| 9 | Negative | 7.0 |
| 10 | Positive | 42.0 |
| 11 | Negative | 21.3 |
| 12 | Positive | 49.0 |
| 13 | Positive | 58.1 |
| 14 | Negative | 7.3 |
| 15 | Negative | 3.8 |
| 16 | Negative | 15.0 |
| 17 | Negative | 0.0 |
| 18 | Positive | 47.2 |
| 19 | Positive | 15.9 |
| 20 | Positive | 89.5 |
| 21 | Positive | 67.4 |
| 22 | Negative | 19.4 |
| 23 | Positive | 36.0 |
| 24 | Positive | 57.0 |
| 25 | Positive | 47.6 |

TABLE 7

| Number | MxA rapid test (40 ng/ml) | MxA EIA |
|---|---|---|
| 15/16 | Negative | 0.0 |
|  | Negative | 0.0 |
|  | Negative | 3.8 |
|  | Negative | 4.0 |
|  | Negative | 5.9 |
|  | Negative | 5.9 |
|  | Negative | 6.0 |
|  | Negative | 7.0 |
|  | Negative | 7.3 |
|  | Positive | 15.0 |
|  | Negative | 15.9 |
|  | Negative | 18.8 |
|  | Negative | 19.2 |
|  | Negative | 19.4 |
|  | Negative | 21.3 |
|  | Negative | 32.9 |
| 9/9 | Positive | 36.0 |
|  | Positive | 42.0 |
|  | Positive | 47.2 |
|  | Positive | 47.6 |
|  | Positive | 49.0 |
|  | Positive | 57.0 |
|  | Positive | 58.1 |
|  | Positive | 67.4 |
|  | Positive | 89.5 |

Rapid, point-of-care low-CRP level and high-CRP level immunoassays were developed and compared to the CRP ELISA in 25 peripheral blood samples from patients with a febrile respiratory illness. These patients are the same patients that were tested for MxA in Tables 6 and 7. The results are shown in Table 8.

TABLE 8

| Number | High CRP Rapid Test (80 mg/L) | Low CRP Rapid Test (10 mg/L) | CRP EIA |
|---|---|---|---|
| 1 | Negative | Positive | 10.8 |
| 2 | Negative | Positive | 45.1 |
| 3 | Negative | Positive | 56.0 |
| 4 | Negative | Positive | 37.6 |
| 5 | Negative | Positive | 27.8 |
| 6 | Positive | Positive | 67.0 |
| 7 | Negative | Positive | 16.2 |
| 8 | Positive | Positive | 59.0 |
| 9 | Negative | Negative | 40.7 |
| 10 | Negative | Positive | 43.0 |
| 11 | Negative | Positive | 13.3 |
| 12 | Negative | Positive | 6.2 |
| 13 | Negative | Positive | 16.1 |
| 14 | Negative | Positive | 36.2 |
| 15 | Negative | Positive | 28.4 |
| 16 | Negative | Positive | 11.4 |
| 17 | Positive | Positive | 110.0 |
| 18 | Negative | Positive | 43.7 |
| 19 | Negative | Positive | 15.3 |
| 20 | Positive | Positive | 110.0 |
| 21 | Negative | Positive | 44.0 |
| 22 | Negative | Positive | 20.0 |
| 23 | Negative | Positive | 80.0 |
| 24 | Negative | Positive | 28.0 |
| 25 | Negative | Positive | 32.0 |

Patient number 6 and 8 showed a positive CRP result even though the ELISA results were below 80 mg/L. Patient 23 showed a negative result even though the ELISA results were exactly 80 mg/L. Patient number 9 showed a negative low CRP test result even though the ELISA results for that patient were above 10 mg/L. But, overall, the CRP values correlated well with the CRP ELISA at both cut-off values.

Using an MxA and CRP ELISA, RPS analyzed 25 healthy, normal blood bank samples for the presence or absence of elevated MxA and CRP. The average CRP concentration in plasma was shown to be 1.6 mg/L. CRP levels were shown to range from 0.1 to 3.7 mg/L. The results are shown in Table 9.

TABLE 9

| Sample | MxA ELISA Concentration (ng/ml) | CRP ELISA Concentration (mg/L) | MxA Rapid Test |
|---|---|---|---|
| 1 | 0 | 1.8 | − |
| 2 | 0 | 1.5 | − |
| 3 | 0 | 1.0 | − |
| 4 | 0 | 1.8 | − |
| 5 | 0 | 3.0 | − |
| 6 | 0 | 0.8 | − |
| 7 | 0 | 2.9 | − |
| 8 | 0 | 0.8 | − |
| 9 | 0 | 1.5 | − |
| 10 | 0 | 0.2 | − |
| 11 | 0 | 1.5 | − |
| 12 | 0 | 1.2 | − |
| 13 | 0 | 3.7 | − |
| 14 | 0 | 0.1 | − |
| 15 | 0 | 0.4 | − |
| 16 | 0 | 2.3 | − |
| 17 | 0 | 2.4 | − |
| 18 | 0 | 3.1 | − |
| 19 | 0 | 0.9 | − |
| 20 | 0 | 0.5 | − |
| 21 | 0 | 2.3 | − |
| 22 | 11.631 | 1.8 | − |
| 23 | 0 | 1.7 | − |
| 24 | 0 | 3.2 | − |
| 25 | 0 | 0.5 | − |

The bimodal dual test strips can be used to differentiate bacterial and viral infection in humans, but also may be used in veterinary applications for animals. Since CRP differs depending upon the species, there are not common antibodies to CRP between species. Therefore, the veterinary tests need to include CRP specific to the particular species being tested. MxA is well conserved among species, so it is possible to use human MxA in veterinary tests. However, MxA to a particular species could alternatively be used to try to further increase specificity. Veterinary tests using the bimodal dual test strips described herein may be developed for a specific species, including, but not limited to, cats, dogs, rabbits, pigs, sheep, horses, cows, monkeys, chimpanzees, baboons, and orangutans.

The strip with MxA and low CRP could be made with any configuration, for example the configurations shown in FIGS. 4A and 4B, or FIGS. 5A through 5D, where MxA is the viral marker being detected and relatively low levels of CRP is the bacterial marker being detected. In other embodiments, the MxA test line and the CRP test line could overlap, or be in the same location on the test strip. In these embodiments, the presence of low CRP and MxA on the same test line has different characteristics than the presence of either a bacterial or viral marker alone. For example, the presence of both low CRP and MxA on the same test line may be visually indicated by a different color than the presence of either MxA or low CRP alone. In these embodiments, a positive result for MxA would give a different color or indication than a positive result for low CRP, so that the person reading the assay could distinguish between a completely negative result, a positive result for MxA, a positive result for low CRP, and a positive result for both MxA and low CRP. For example, a positive result for MxA could result in a red test line, and a positive result for low CRP could result in a blue test line. So, when a sample is positive for both MxA and low CRP, the line is visibly purple.

Some embodiments for lateral flow assay devices to detect high levels of CRP are shown in FIGS. 6A-6B and 7A-7D. These configurations are similar to the configurations shown in FIGS. 4A-4B and 5A-5D, without a test line for a viral marker, and the same reference numerals are used for the same components of the strip (600), (700).

Figure 6A:
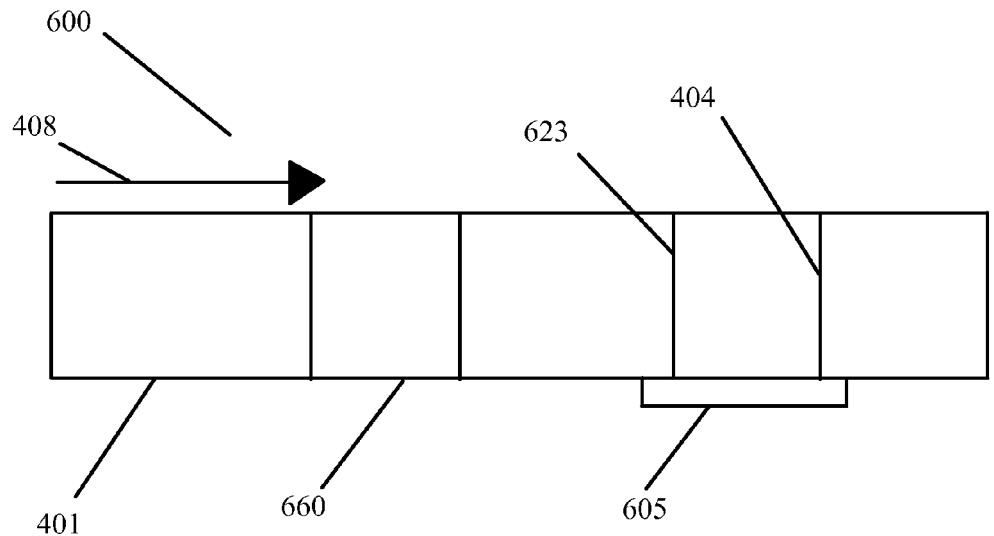
FIG. 6A shows a device with a test line corresponding to the presence of a bacterial marker such as high CRP levels in an embodiment of the present invention.
Figure 6B:
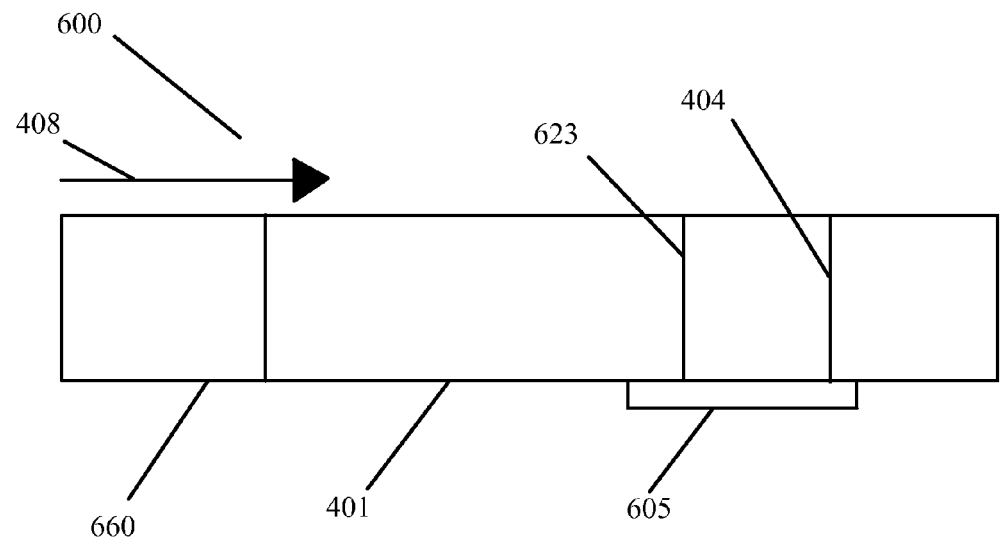
FIG. 6B shows a device with a test line corresponding to the presence of a bacterial marker such as high CRP levels in another embodiment of the present invention.

FIGS. 6A and 6B show a chromatographic test strip (600) with a test line (623) that detects the presence of a bacterial marker, such as high levels of CRP. The sample is applied to the application zone (401) of the chromatographic test strip (600). As shown in FIG. 6A, the sample then passes a reagent zone (660) containing at least one labeled bacterial binding partner that is eluted by and then able to migrate with a sample transport liquid (e.g. a buffer solution). Alternatively, as shown in FIG. 6B, the reagent zone (660) is located upstream of the sample application zone (401) such that the labeled binding partners in the reagent zone are eluted by the sample transport liquid and travel to the sample. The labeled bacterial binding partner is capable of specifically binding to a bacterial marker of interest, for example high levels of CRP, to form a complex which in turn is capable of specifically binding to another specific reagent or binding partner in the detection zone. Although not shown in these Figures, an absorbent pad, as well as other known lateral flow immunoassay components including, but not limited to, a waste zone, a carrier backing, a housing, and an opening in the housing for result read out, may optionally also be a component of the test strip (600) in these embodiments.

The test strip (600) also includes a detection zone (605) containing a section for detection of a bacterial marker, e.g. a test line (623), including an immobilized specific binding partner, complementary to the bacterial reagent complex formed by the bacterial marker and its labeled binding partner. Thus, at the test line (623), detection zone binding partners trap the labeled bacterial binding partners from the reagent zone (660) along with their bound bacterial markers. This localization of the bacterial marker with its labeled binding partners gives rise to an indication at the test line (623). At the test line (623), the presence of the bacterial marker is determined by qualitative and/or quantitative readout of the test line (623) indication resulting from the accumulation of labeled binding partners.

Optionally, the detection zone (605) may contain further test lines to detect other bacterial and/or viral markers, as well as a control line (404). The control line (404) indicates that the labeled specific binding partner traveled through the length of the assay, even though it may not have bound any bacterial markers, thus confirming proper operation of the assay. As shown in FIGS. 6A through 6B, the control zone (404) is preferably downstream of the test line (623). However, in other embodiments, the control zone (404) may be located upstream of the test line (623).

In a preferred embodiment, the control line (404) includes an antibody or other recombinant protein which binds to a component of the elution medium or other composition being used in the test. In embodiments where nucleic acids are the targets, the control line (404) preferably includes a nucleic acid complementary to the labeled nucleic acid being used as a binding partner for the target nucleic acid.

In other preferred embodiments to test for a bacterial marker, such as high CRP levels, as shown in FIGS. 7A through 7D, the sample passes a lysis zone (250), where a lysis agent will have preferably been pre-loaded onto the test strip and is eluted by the transport liquid. The lysis agent lyses any lysis-susceptible components in the sample in situ.

The chromatographic test strip (700) contains a sample application zone (201), a lysis zone (250) containing a lysis agent, and a reagent zone (760) containing at least one labeled binding partner that binds to a bacterial marker, for example high levels of CRP, that is eluted by and then able to migrate with a sample transport liquid (e.g. a buffer solution). While the reagent zone (760) is shown downstream of the sample application zone in these figures, in alternative embodiments, the reagent zone (760) could be upstream of the sample application zone (see FIG. 6B), as long as the reagents encounter the sample at some point after the sample reaches the lysis zone and is effectively lysed. The labeled binding partner is capable of specifically binding to a bacterial marker of interest, for example high levels of CRP, to form a complex which in turn is capable of specifically binding to another specific reagent or binding partner in the detection zone. Although not shown in these Figures, an absorbent pad, as well as other known lateral flow immunoassay components including, but not limited to, a waste zone, a carrier backing, a housing, and an opening in the housing for result read out, may optionally also be a component of the test strip (700) in these embodiments.

In a preferred embodiment, the lysis agent is localized in the lysis zone (250) between the sample application zone (201) and the reagent zone (760). The lysis agent is preferably soluble or miscible in the sample transport liquid, and the lysis agent is solubilized and activated upon contact with the sample transport liquid. The sample transport liquid then contains both lysis agent in solution or suspension and sample components in suspension. Any lysis-susceptible components in a sample, then being exposed in suspension to the lysis agent, are themselves lysed in situ. The running buffer then carries the sample, including any lysis-freed components, to the detection zone (705).

Figure 7A:
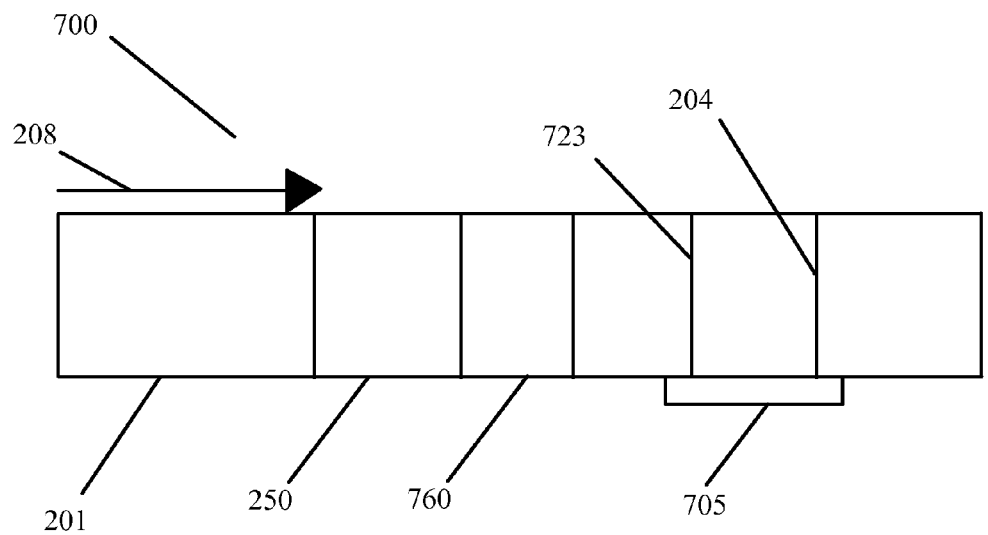
FIG. 7A shows a sample analysis device including a lysis zone located between a sample application zone and a reagent zone in an embodiment of the present invention.
Figure 7B:
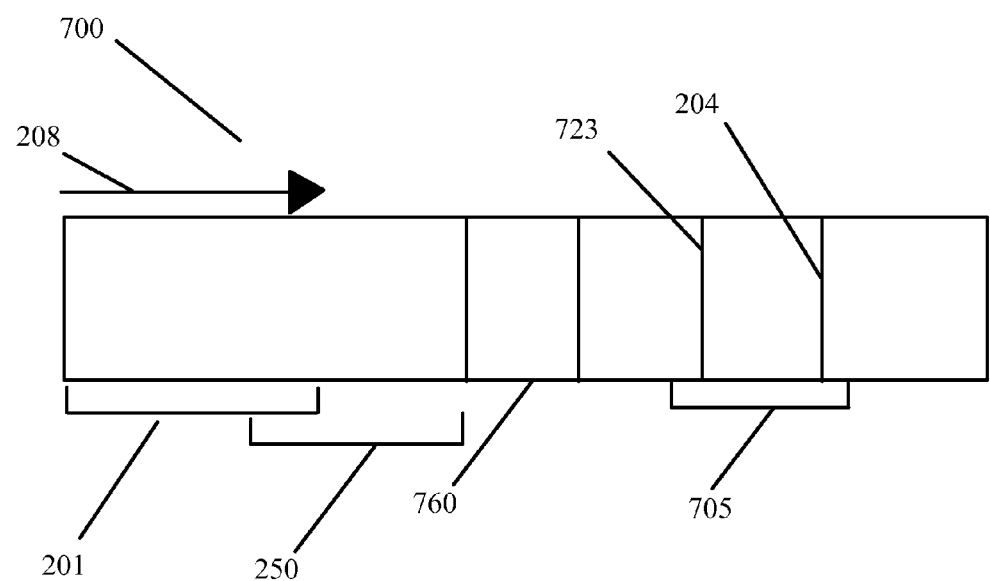
FIG. 7B shows a sample analysis device including a lysis zone overlapping a sample application zone in an embodiment of the present invention.
Figure 7C:
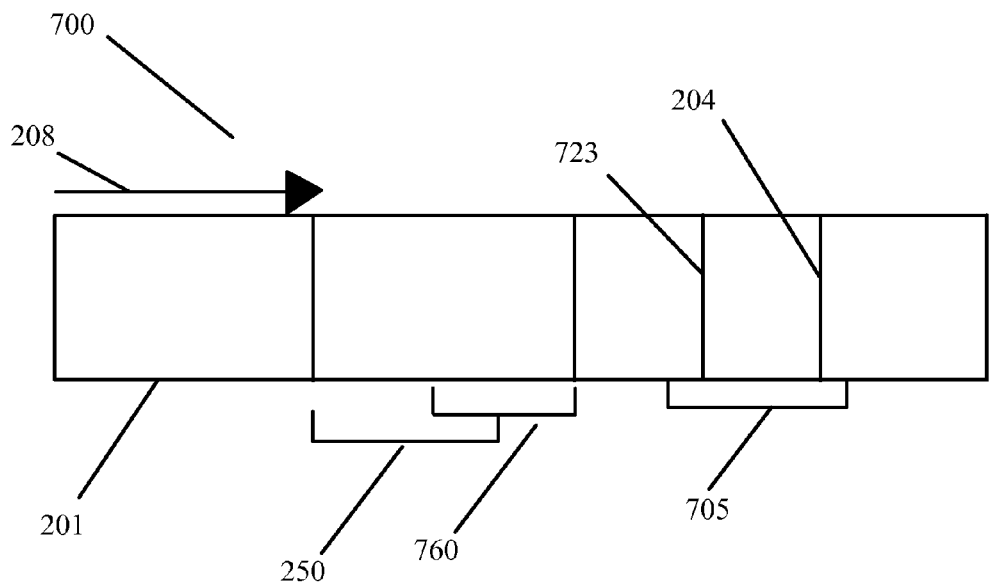
FIG. 7C shows a sample analysis device including a lysis zone overlapping a reagent zone in an embodiment of the present invention.
Figure 7D:
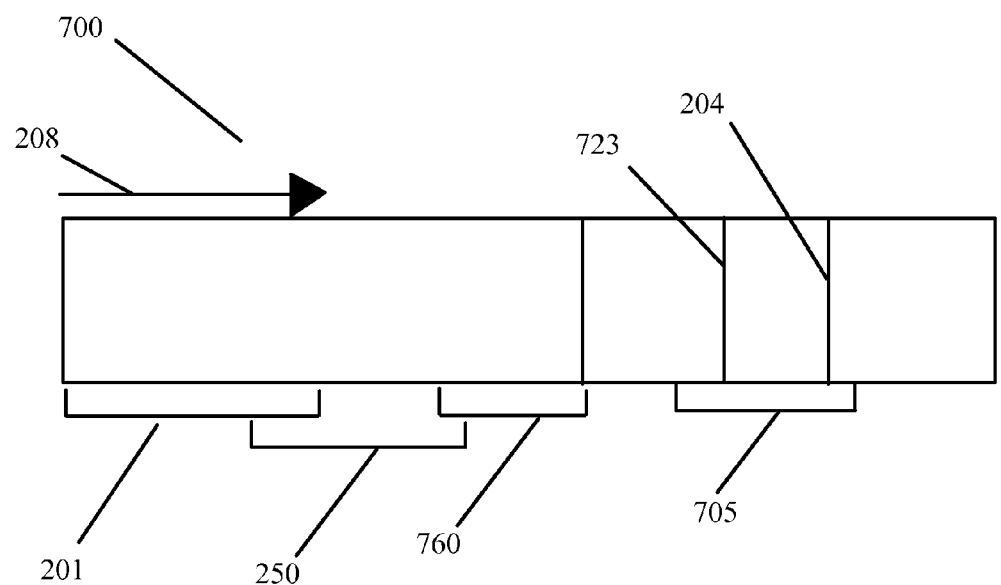
FIG. 7D shows a sample analysis device including a lysis zone overlapping a sample application zone and a reagent zone in an embodiment of the present invention.

The lysis zone (250) is preferably located between the sample application zone (201) and the reagent zone (760), as shown in FIG. 7A. In other embodiments, the lysis zone (250) overlaps the sample application zone (201), the reagent zone (760) or both the sample application zone (201) and the reagent zone (260) as shown in FIGS. 7B, 7C, and 7D, respectively. Note that the figures are schematic, and are not drawn to scale. The amount of overlap between the different zones (as shown in FIGS. 7B through 7D) may be highly variable.

The test strip (700) also includes a detection zone (705) containing a section for detection of at least one bacterial marker, e.g. a test line (723), including an immobilized specific binding partner, for example, a specific binding partner for a high level of CRP, complementary to the bacterial conjugate formed by the bacterial marker and its labeled binding partner. Thus, at the test line (723), detection zone binding partners trap the bacterial labeled binding partners from the reagent zone (760) along with their bound bacterial markers. This localization of the bacterial markers with their labeled binding partners gives rise to an indication at the test line (723). At the test line (723), the presence of a bacterial marker is determined by qualitative and/or quantitative readout of the test line (723) indication resulting from the accumulation of labeled binding partners.

Optionally, the detection zone (705) may contain further test lines to detect other bacterial and/or viral markers, as well as a control line (204). The control line (204) indicates that the labeled specific binding partner traveled through the length of the assay, even though it may not have bound any markers, thus confirming proper operation of the assay. As shown in FIGS. 7A through 7D, the control zone (204) is preferably downstream of the test line (723). However, in other embodiments, the control zone (204) may be located upstream of the test line (723).

In a preferred embodiment, the control line (204) includes an antibody or other recombinant protein which binds to a component of the elution medium or other composition being used in the test. In embodiments where nucleic acids are the targets, the control line (204) preferably includes a nucleic acid complementary to the labeled nucleic acid being used as a binding partner for the target nucleic acid.

Figure 8A:
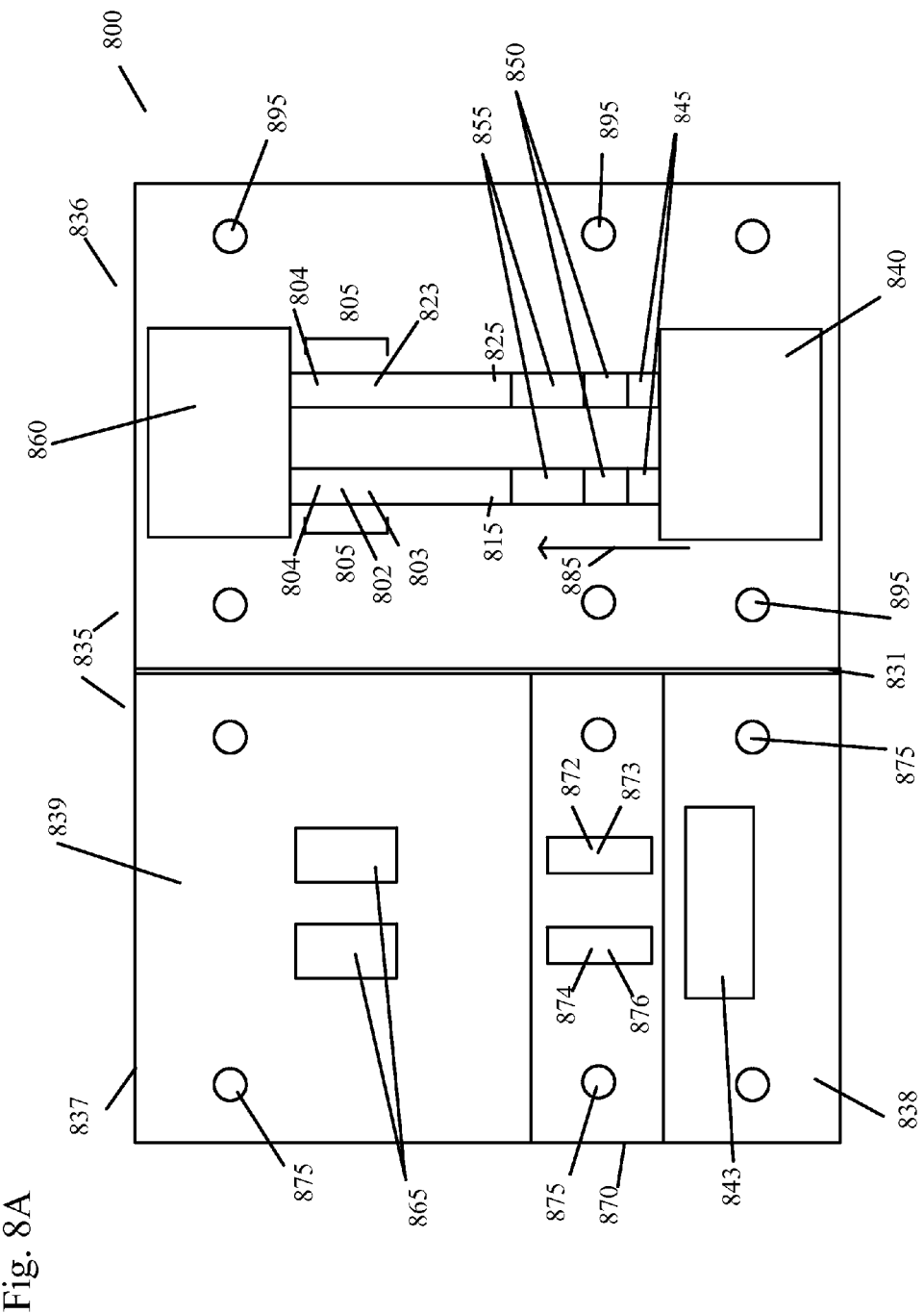
FIG. 8A shows a fully open sample analysis device with dual test strips, as well as a conjugate zone and a sample application zone on a sample compressor in a plane separate from the test strips in an embodiment of the present invention.
Figure 8B:
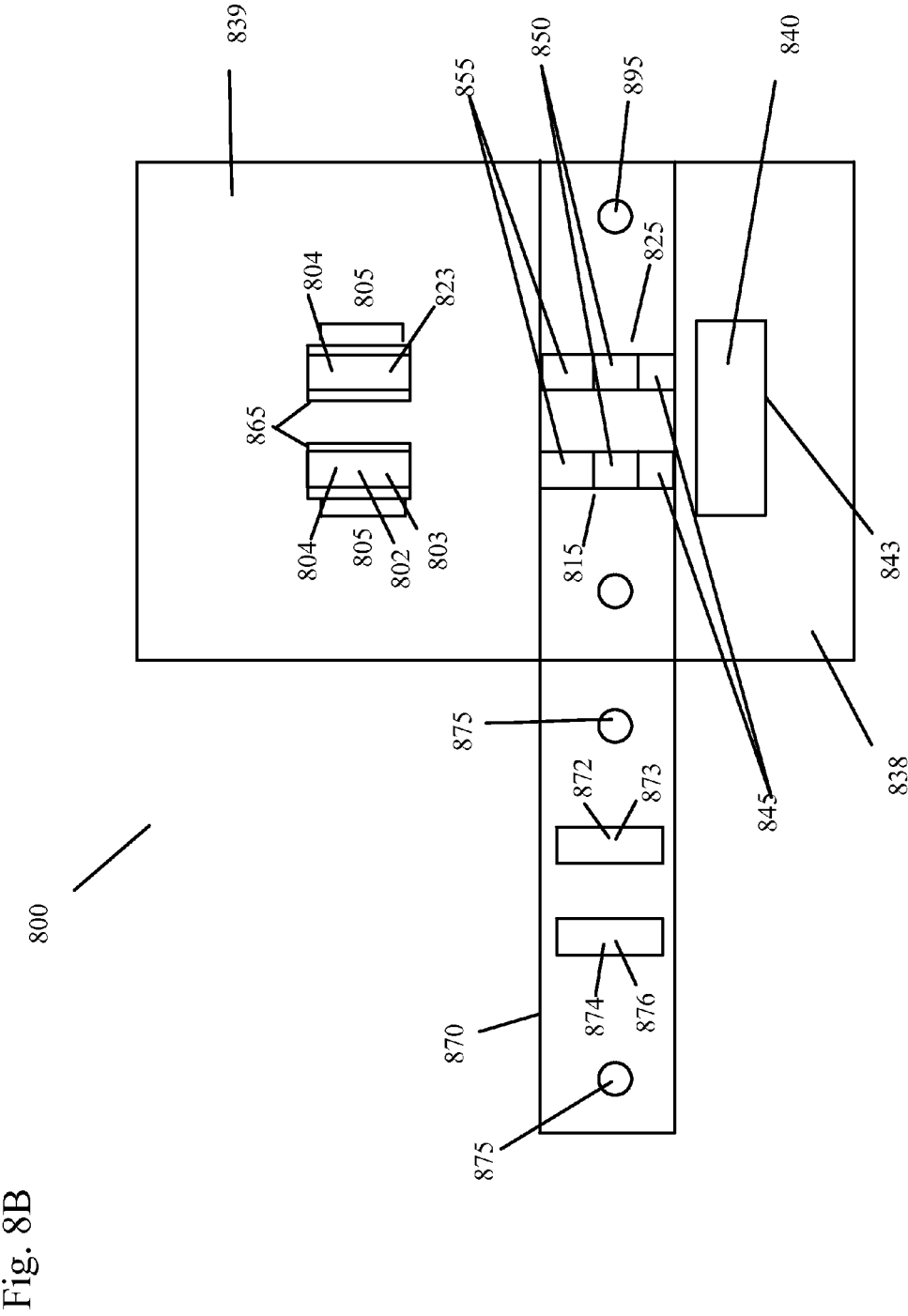
FIG. 8B shows the sample analysis device of FIG. 8A with part of the housing closed, but the conjugate zone still visible on the left side of the device.
Figure 8C:
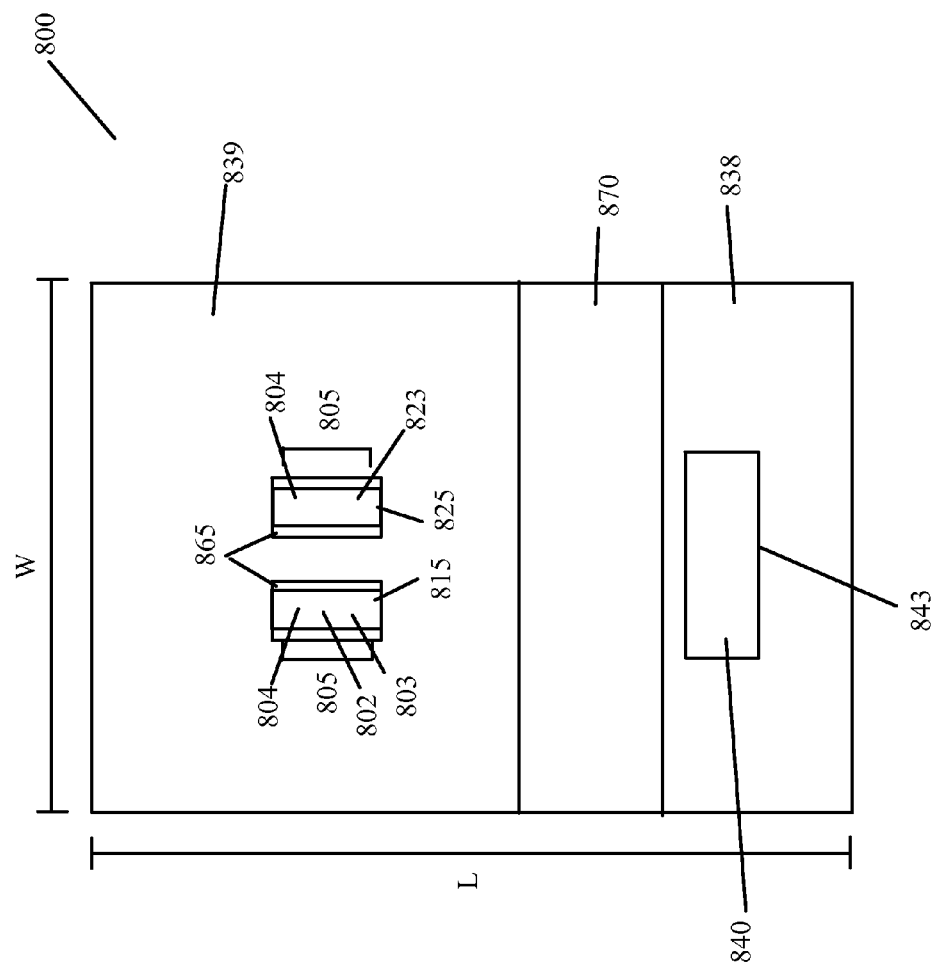
FIG. 8C shows the sample analysis device of FIG. 8A after the test has been initiated.

One preferred configuration for a bimodal dual test strip sample analysis device is shown in FIGS. 8A through 8C. The sample analysis device or test card (800) includes a closable housing (835) with two sides (836), (837) and a spine or hinged portion (831). In one preferred embodiment, the test card (800) is approximately 11.5 cm long (L)×7 cm wide (W) when the two sides (836), (837) are closed. However, any size test card (800) that accommodates all of the components may be used. Within the first side (836) of the housing (835), there are two test strips (815), (825), each including a receiving pad (845), a diverting zone (850), a transfer pad (855) and a detection zone (805). The first side (836) also includes an absorbent pad (840) and preferably a waste pad (860). The first test strip (815) preferably includes a detection zone (805) with an MxA test line (802), a low CRP test line (803) and a control line (804). The second test strip (825) preferably includes a detection zone (805) with a high CRP test line (823) and a control line (804). All of the test lines are visible through the windows (865) on the second side (837) of the housing (835) when the housing (835) is closed. The absorbent pad (840) is preferably a single pad that the running buffer is added to to start lateral flow. Similarly, the waste pad (860) is preferably a single pad that collects excess running buffer at the end of the test. However, in other embodiments, each strip could have a separate absorbent pad (840) and/or waste pad (860).

The second side (837) of the housing (835) includes three separate sections (838), (839) and (870). The middle portion, a sample compressor or flap (870), preferably includes two conjugate zones (872), (874), each including a labeled binding partner for at least one analyte, and a labeled control. A window (843) is located in the lower portion (838) of the second side (837) of the housing so that the buffer can be added to the absorbent pad (840) when the housing (835) is closed. The viewing windows (865) for the detection zones (805) are on the upper portion (839) of the second side (837) of the housing (835).

The upper portion (839) and the lower portion (838) of the second side (837) of the housing (835) also preferably each include at least one knob, peg or protrusion (875) that mates with one or more holes (895) so that the upper and lower portions (838), (839) may be easily fastened onto the first side (836) of the housing (835). In a preferred embodiment, there are two pegs (875) on the lower portion (838) that mate with two holes (895) flanking the absorbent pad (840) on the first side (836) of the housing (835) and two pegs (875) on the upper portion (839) that mate with two holes (895) flanking the waste pad (860) on the first side (836) of the housing (835). In other embodiments, the holes (895) are on the second side (837) of the housing (835) and the pegs (875) are on the first side (836) of the housing (835). In yet other embodiments, other reversible fastening mechanisms could be used to secure the upper portion (838) and/or lower portion (839) of the second side (837) of the housing (835) to the first side (836) of the housing (835). In other embodiments, the upper and lower sections (838), (839) are permanently closed, for example using an adhesive, before use.

The flap (870), also known as a sample compressor, on the second side (837) of the housing includes two conjugate zones (872), (874) and two sample application zones (873), (876), and can be easily opened and closed. The flap (870) also preferably includes at least one knob, peg or protrusion (875) that mates with one or more holes (895) so that the flap (870) is easily correctly closed onto the first side (836) of the housing (835) after sample has been added to the sample application zones (873), (876). In other embodiments, the holes (895) are on the second side (837) of the housing (835) and the pegs (875) are on the first side (836) of the housing (835). In yet other embodiments, other reversible fastening mechanisms could be used to secure the flap (870) to the first side (836) of the housing (835).

The conjugate zones (872), (874) and the sample application zones (873), (876) preferably overlap. In preferred embodiments, the conjugate zones (872), (874) are colored due to the dyes in the sample conjugates and control conjugates, and the sample is placed directly on the colored portion of the flap (870). In one preferred embodiment, the conjugate zone (872) that is used for the first test strip (815) contains an MxA binding partner that is labeled with a red dye, a low CRP binding partner that is labeled with a black dye, and a control binding partner that is labeled with a blue dye. In this embodiment, the conjugate zone (872) appears purplish. The other conjugate zone (874) contains a high CRP binding partner that is labeled with a black dye and a control binding partner that is labeled with a blue dye. In this embodiment, the conjugate zone (874) appears bluish.

The diverting zone (850) preferably includes a gap or barrier that interrupts lateral flow, diverting the running buffer up into the flap (870) that includes the conjugate zones (872), (874) and the sample application zones (873), (876).

In operation, the upper and lower portions (838), (839) of the second side (837) of the housing (835) are preferably snapped closed before use by securing the pegs (875) to the holes (895). The sample analysis device, or test card (800) is preferably placed on a flat surface. If the flap (870) is not already open, the user opens it to access the sample application zones (873), (876). A blood sample to be tested is taken from the patient. The sample may be taken by any procedure known in the art. In a preferred embodiment, a sample of 5 µl of blood is added to each of the sample application zones (873), (876) and then the flap (870) is closed. Each of the 5 µl samples is preferably collected independently of each other. The blood samples are preferably added directly to the device (800), without any pretreatment.

To ensure that the sample compressor or flap (870) has been closed correctly, pressure is preferably applied to the housing (835) above the pegs (875) to snap the pegs (875) closed. The top of the flap (870) needs to be flush with the top of the rest of the second side (837) of the housing (835) for the test to run properly. Running buffer is added to the absorbent pad (840), which initiates lateral flow (885). In preferred embodiments, the running buffer includes one or more lysis agents, for example detergents, to lyse the blood sample and expose the intracellular MxA in the sample. When the running buffer reaches the diverting zone (850), it is diverted up into the flap (870). It travels through the conjugate zones (872), (874), collecting any complexes formed between the MxA binding partner and MxA in the sample, the low CRP binding partner and low levels of CRP in the sample, the high CRP binding partner and high levels of CRP in the sample, as well as the control conjugate.

Since the conjugate zones (872), (874) bridge the diverting zone (850) on the lateral flow test strips (815), (825), the running buffer, which now contains sample, conjugate, and the complexes described above, then travels into the transfer pad (855), and to the detection zones (805) on each of the test strips (815), (825). If MxA is present in the sample, the MxA test line (802) on the first test strip (815) will be red. If a threshold low level of CRP is present in the sample, the low CRP test line (803) on the first test strip (815) will be black. If a threshold high level of CRP is present in the sample, the high CRP test line (823) on the second test strip (825) will be black. If the test is run correctly, the control lines (804) on both the first strip (815) and the second test strip (825) will be blue. In preferred embodiments, the levels of detection are 40 ng/ml for MxA, 10 mg/L for low CRP on the first test strip (815) and 80 mg/L for high CRP on the second test strip (825). The results of the test should be visible after approximately 5-20 minutes, preferably within about 10 minutes.

Since the control binding partner is on the sample compressor or flap (870) and not on either of the test strips (815), (825), there is a true procedural control to this configuration. If the flap (870) is not closed properly, nothing will show up in the detection zone (805), indicating that the test was run improperly.

FIGS. 9A through 9F show test results using the device (800) shown in FIGS. 8A through 8C, with two test strips (815), (825) side by side, where a first test strip (815) tests for the presence of both MxA and low levels of CRP and the second test strip (825) tests for high levels of CRP.

Figure 9A:
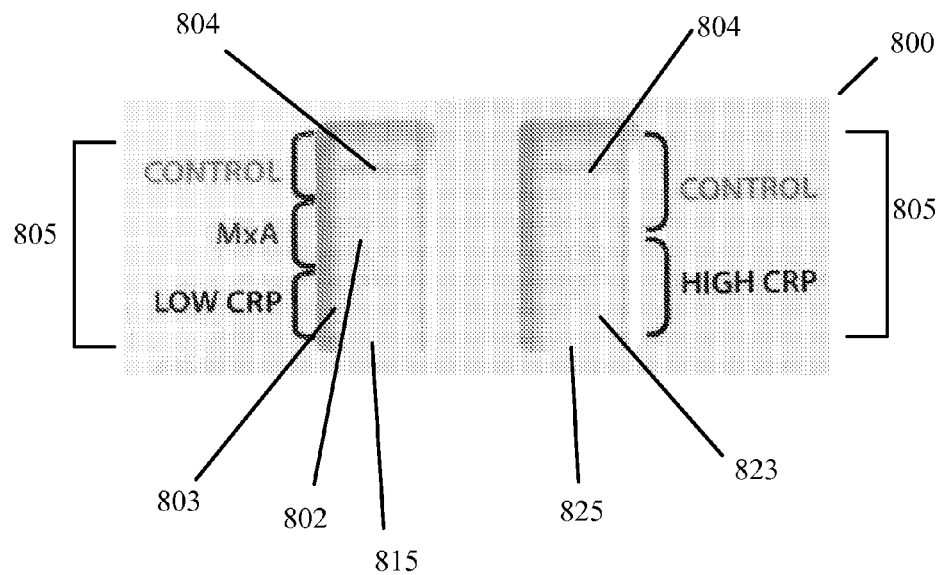
FIG. 9A shows a test result negative for both MxA and CRP in an embodiment of the present invention.

FIG. 9A shows a negative result at the MxA test line (802) and a negative result at the low CRP test line (803) on the first test strip (815), as well as a negative result at the high CRP test line (823) on the second test strip (825). More specifically, the only visible lines in the detection zone (805) of the lateral flow assay (800) are the two blue control lines (804). This result indicates that the sample is negative for both viral and bacterial infection.

Figure 9B:
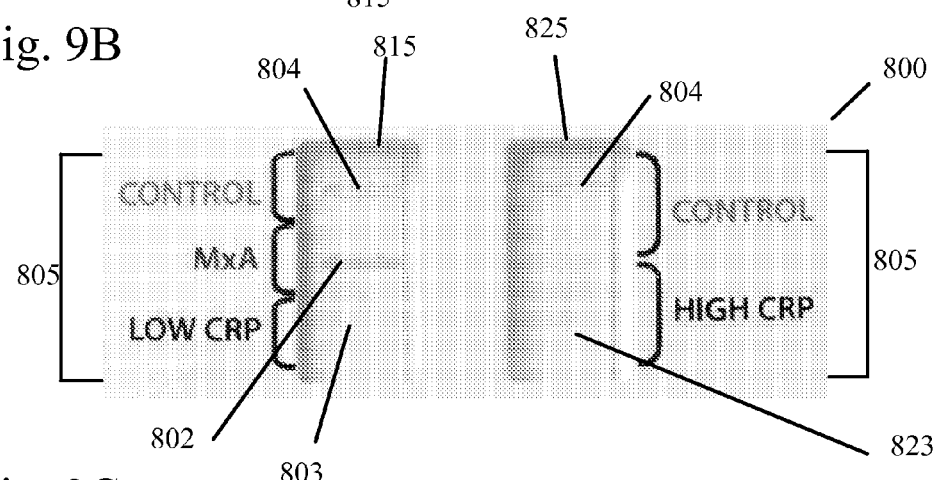
FIG. 9B shows a test result positive for MxA in an embodiment of the present invention.
Figure 9C:
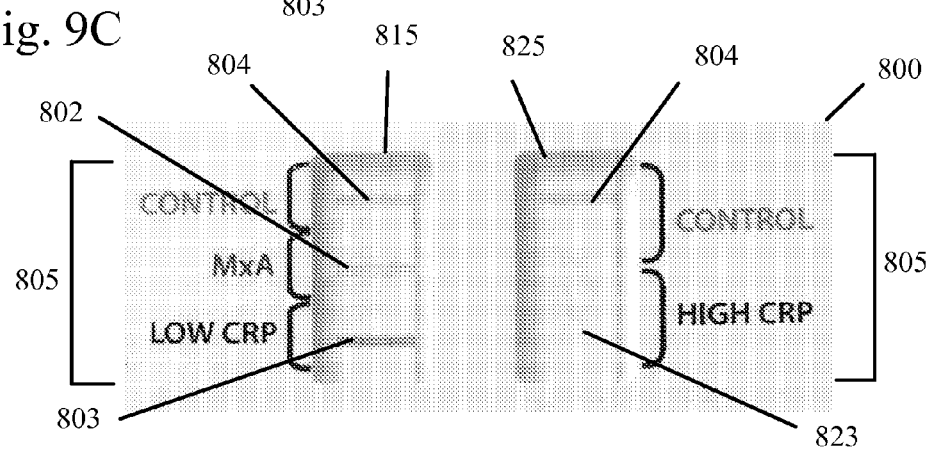
FIG. 9C shows a test result positive for MxA in an embodiment of the present invention.

FIGS. 9B and 9C are positive for viral infection. In FIG. 9B, the presence of two blue control lines (804) and a red MxA line (802) indicate a viral infection. In FIG. 8C, the presence of two blue control lines (804) and a red MxA line (802) indicate a viral infection. Since there is also a black low CRP line (803) in FIG. 9C, there is a possibility of bacterial co-infection, although there is an absence of a high CRP line (823).

Figure 9D:
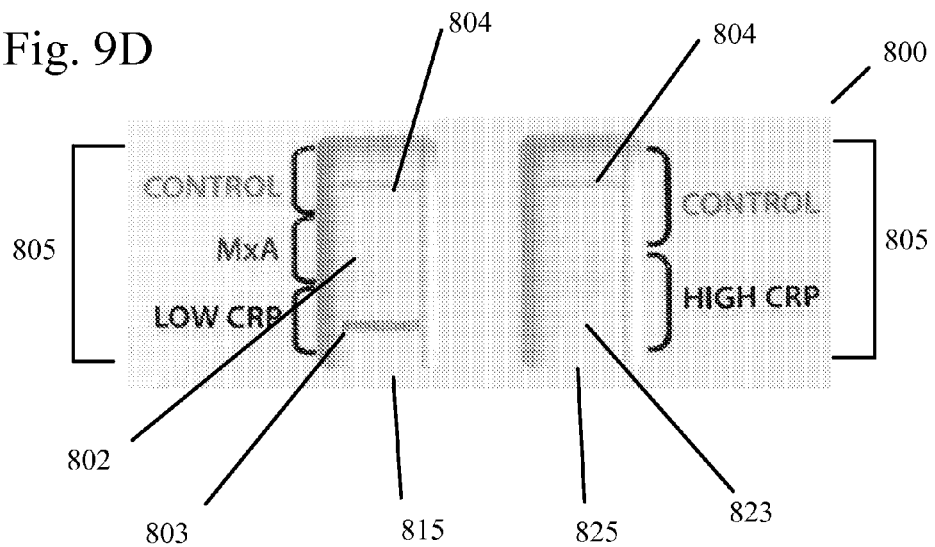
FIG. 9D shows a test result positive for CRP in an embodiment of the present invention.
Figure 9E:
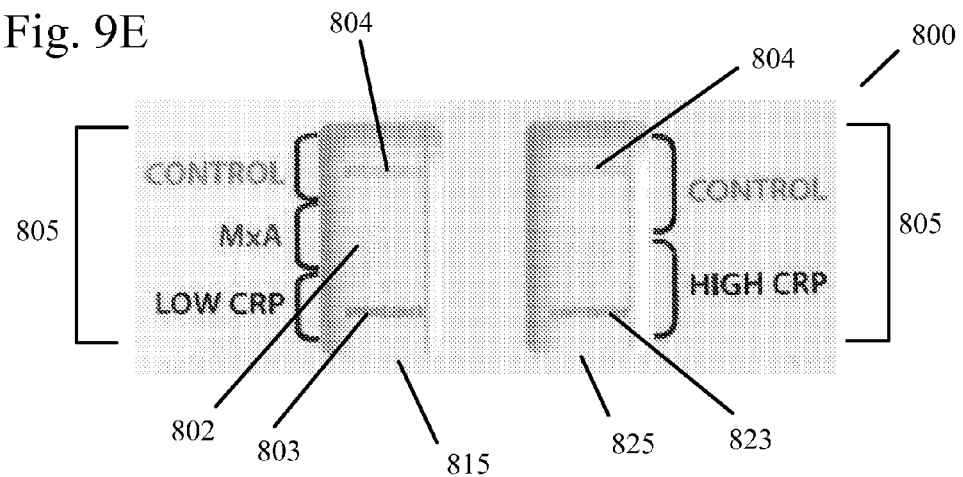
FIG. 9E shows a test result positive for CRP in an embodiment of the present invention.

FIGS. 9D and 9E are positive for bacterial infection. In FIG. 9D, the presence of two blue control lines (804) and a black low CRP line (803) indicates a bacterial infection. In FIG. 9E, the presence of two blue control lines (804), a black low CRP line (803), and a black high CRP line (823) also indicates a bacterial infection. The MxA line is absent in both FIGS. 9D and 9E, indicating an absence of a viral infection.

Figure 9F:
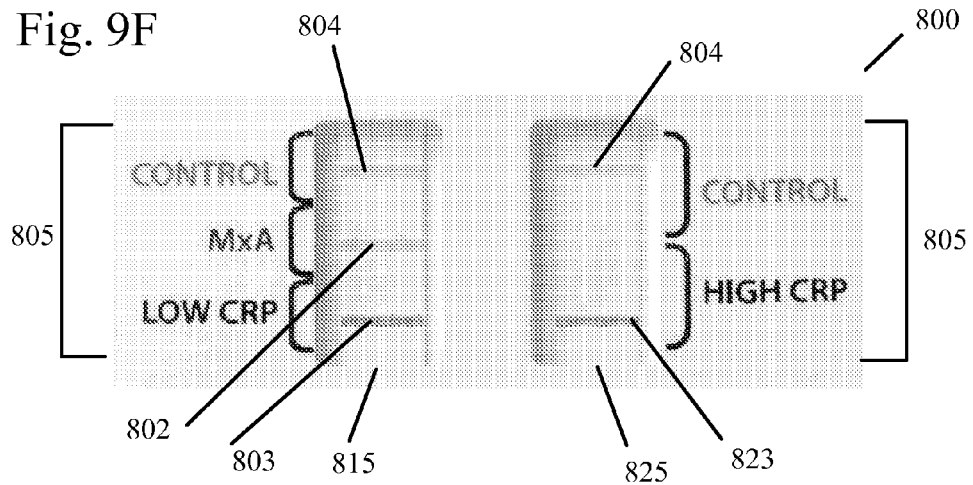
FIG. 9F shows a test result positive for both CRP and MxA, indicating co-infection, in an embodiment of the present invention.

FIG. 9F indicates co-infection (both bacterial and viral infection). The presence of two blue control lines (804), a red MxA line (802), a black low CRP line (803), and a black high CRP line (823) indicates the presence of both viral and bacterial infection.

Figure 10A:
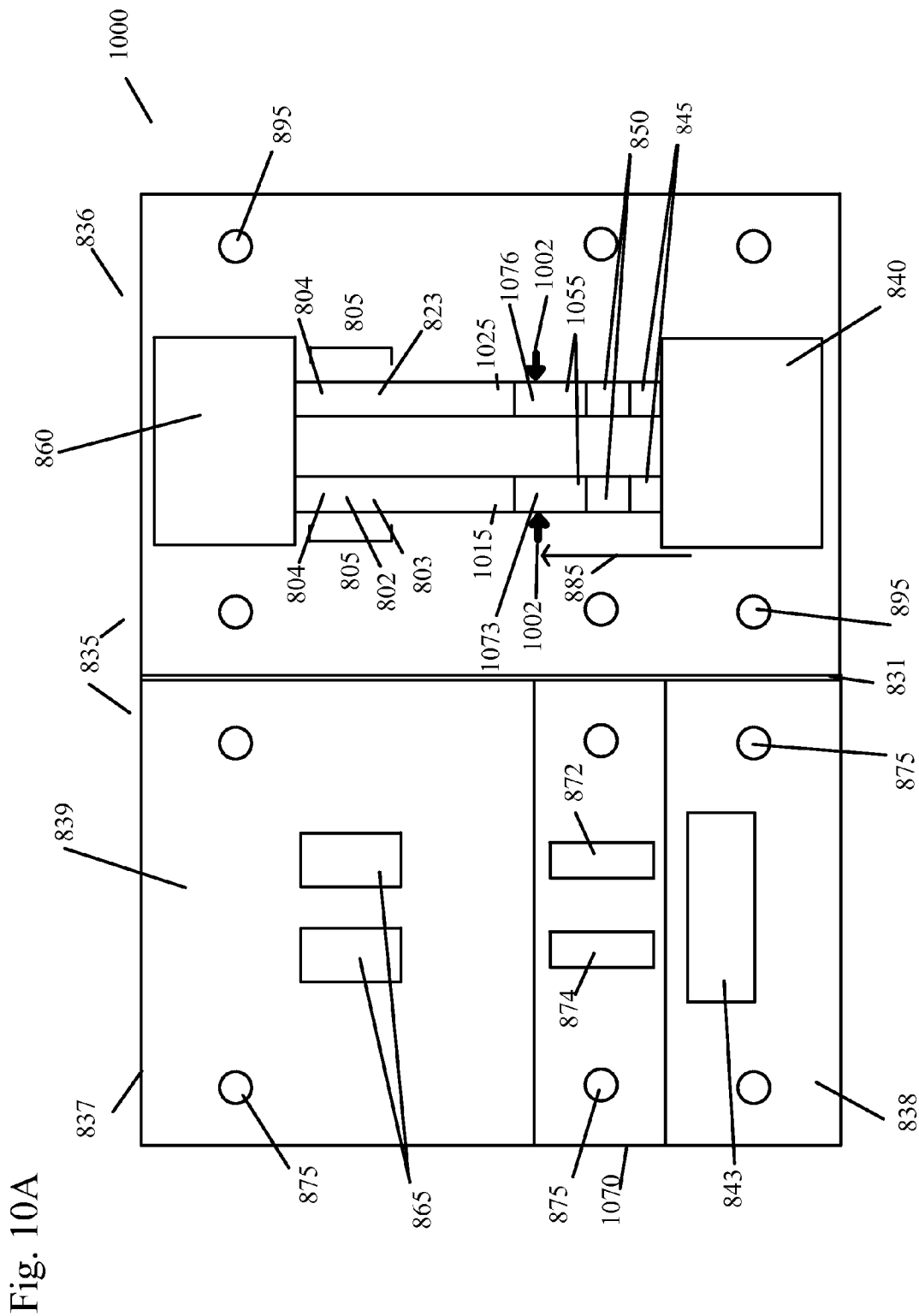
FIG. 10A shows a fully open sample analysis device with dual test strips and a conjugate zone on a sample compressor in a plane separate from the test strips in an embodiment of the present invention.
Figure 10B:
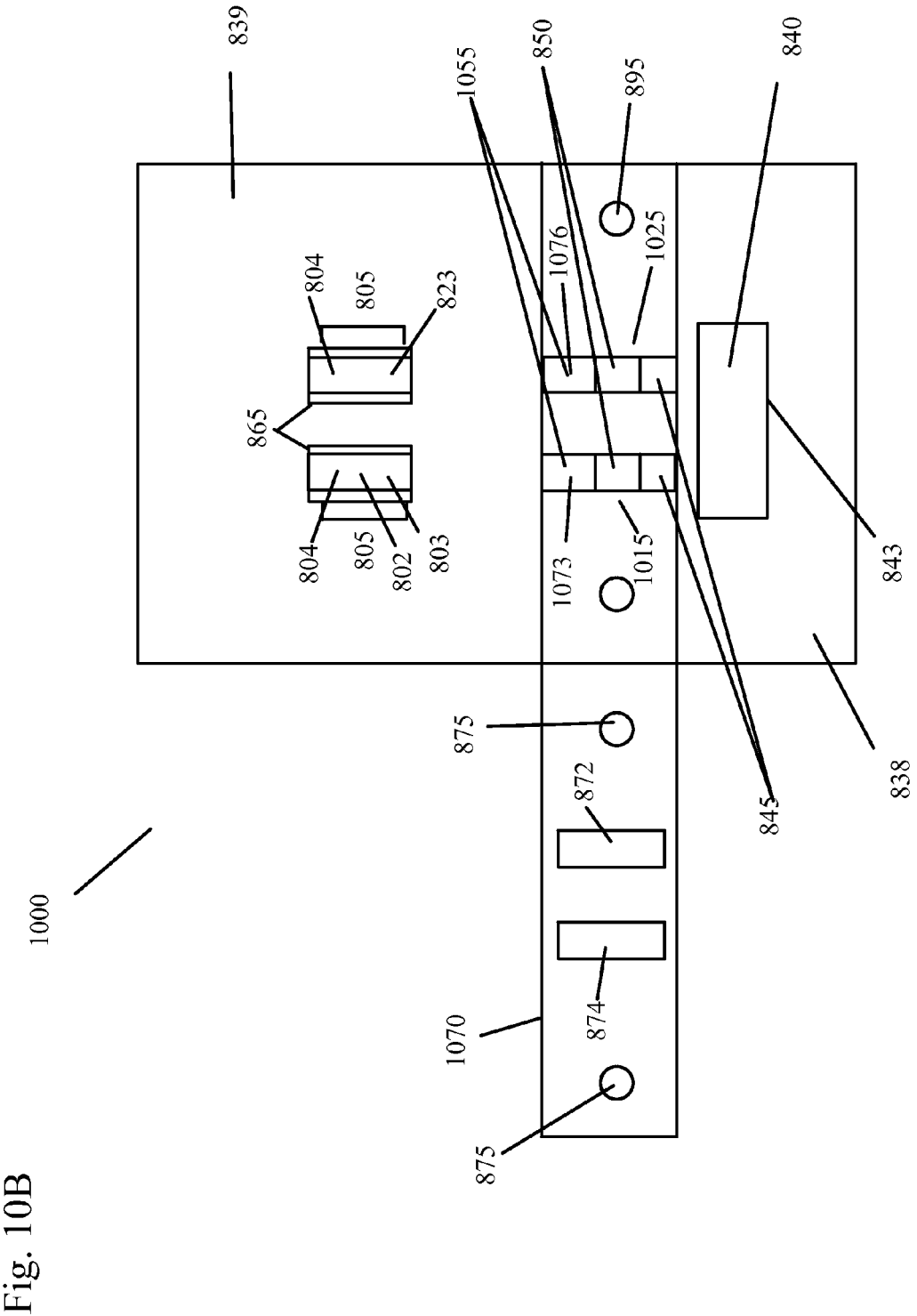
FIG. 10B shows the sample analysis device of FIG. 10A with part of the housing closed, but the conjugate zone still visible on the left side of the device.
Figure 10C:
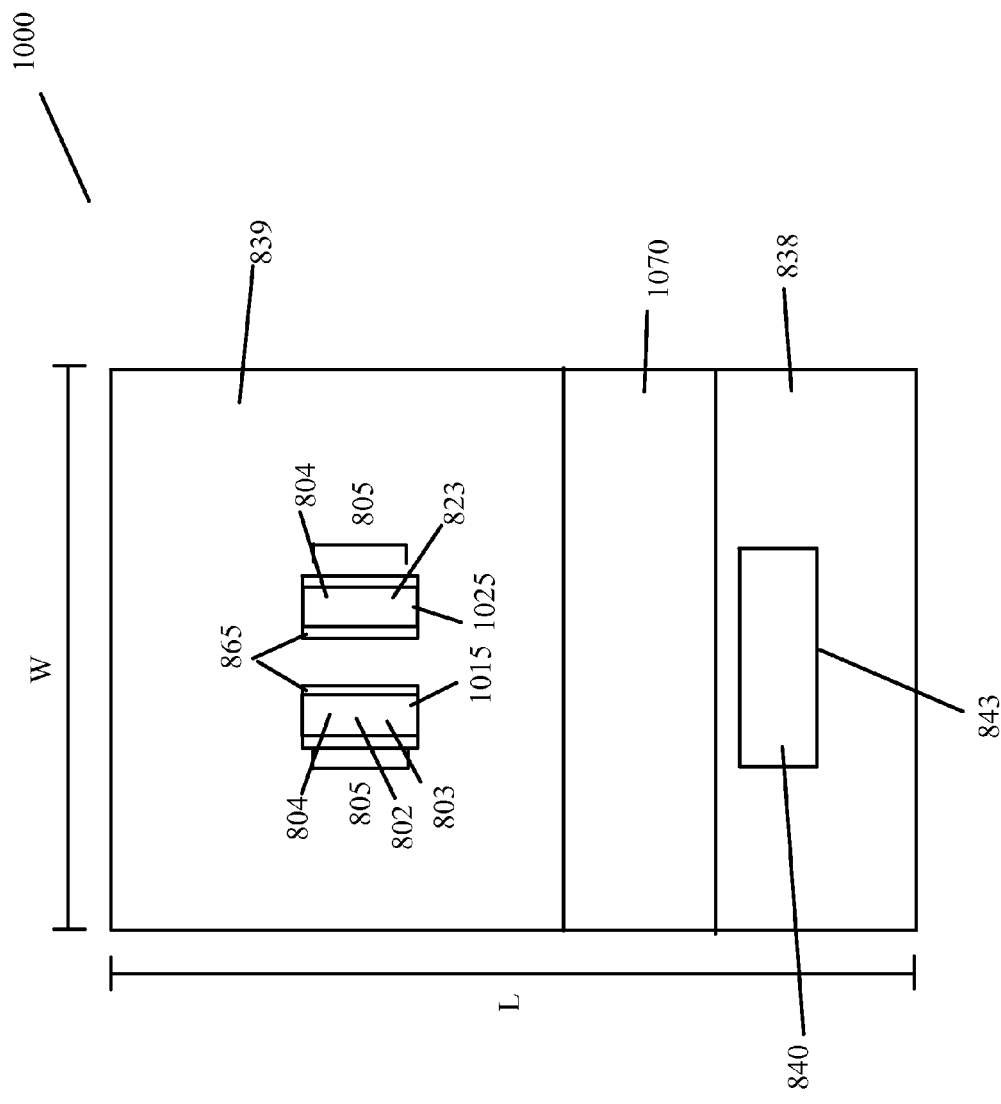
FIG. 10C shows the sample analysis device of FIG. 10A after the test has been initiated.

Another preferred configuration for a bimodal dual test strip sample analysis device (1000) is shown in FIGS. 10A through 10C. This configuration is similar to the configuration (800) shown in FIGS. 8A through 8C, but the sample application zones (1073), (1076) are located on each of the test strips (1015), (1025), downstream of the diverting zone (850). The sample analysis device or test card (1000) includes a closable housing (835) with two sides (836), (837) and a spine or hinged portion (831). In one preferred embodiment, the test card (1000) is approximately 11.5 cm long (L)×7 cm wide (W) when the two sides (836), (837) are closed. However, any size test card (1000) that accommodates all of the components may be used. Within the first side (836) of the housing (835), there are two test strips (1015), (1025), each including a receiving pad (845), a diverting zone (850), a transfer pad (1055) and a detection zone (805). The first side (836) also includes an absorbent pad (840) and preferably a waste pad (860). The first test strip (1015) preferably includes a detection zone (805) with an MxA test line (802), a low CRP test line (803) and a control line (804). The second test strip (1025) preferably includes a detection zone (805) with a high CRP test line (823) and a control line (804). All of the test lines are visible through the windows (865) on the second side (837) of the housing (835) when the housing (835) is closed. The absorbent pad (840) is preferably a single pad to which the running buffer is added to start lateral flow. Similarly, the waste pad (860) is preferably a single pad that collects excess running buffer at the end of the test. However, in other embodiments, each strip could have a separate absorbent pad (840) and/or waste pad (860).

The second side (837) of the housing (835) includes three separate sections (838), (839) and (1070). The middle portion, or flap (1070), also known as a sample compressor, preferably includes two conjugate zones (872), (874), each including a labeled binding partner for at least one analyte, and a labeled control. A window (843) is located in the lower portion (838) of the second side (837) of the housing so that the buffer can be added when the housing (835) is closed. The viewing windows (865) for the detection zones (805) are on the upper portion (839) of the second side (837) of the housing (835).

The upper portion (839) and the lower portion (838) of the second side (837) of the housing (835) also preferably each include at least one knob, peg or protrusion (875) that mates with one or more holes (895) so that the upper and lower portions (838), (839) may be easily fastened onto the first side (836) of the housing (835). In a preferred embodiment, there are two pegs (875) on the lower portion (838) that mate with two holes (895) flanking the absorbent pad (840) on the first side (836) of the housing (835) and two pegs (875) on the upper portion (839) that mate with two holes (895) flanking the waste pad (860) on the first side (836) of the housing (835). In other embodiments, the holes (895) are on the second side (837) of the housing (835) and the pegs (875) are on the first side (836) of the housing (835). In yet other embodiments, other reversible fastening mechanisms could be used to secure the upper portion (838) and/or lower portion (839) of the second side (837) of the housing (835) to the first side (836) of the housing (835). In other embodiments, the upper and lower sections (838), (839) are permanently closed, for example using an adhesive, before use.

The flap (1070) on the second side (837) of the housing includes two conjugate zones (872), (874) and can be easily opened and closed. The flap (1070) also preferably includes at least one knob, peg or protrusion (875) that mates with one or more holes (895) so that the flap (1070) is easily correctly closed onto the first side (836) of the housing (835) after sample has been added to the sample application zones (1073), (1076) on the test strips (1015), (1025). In other embodiments, the holes (895) are on the second side (837) of the housing (835) and the pegs (875) are on the first side (836) of the housing (835). In yet other embodiments, other reversible fastening mechanisms could be used to secure the flap (1070) to the first side (836) of the housing (835).

In preferred embodiments, the conjugate zones (872), (874) are colored due to the dyes in the sample conjugates and control conjugates. In one preferred embodiment, the conjugate zone (872) that is used for the first test strip (1015) contains an MxA binding partner that is labeled with a red dye, a low CRP binding partner that is labeled with a black dye, and a control binding partner that is labeled with a blue dye. In this embodiment, the conjugate zone (872) appears purplish. The other conjugate zone (874) contains a high CRP binding partner that is labeled with a black dye and a control binding partner that is labeled with a blue dye. In this embodiment, the conjugate zone (874) appears bluish.

The diverting zone (850), which preferably includes a gap or barrier, interrupts lateral flow, diverting the running buffer up into the flap (1070) that includes the conjugate zones (872), (874).

In operation, the upper and lower portions (838), (839) of the second side (837) of the housing (835) are preferably snapped closed before use by securing the pegs (875) to the holes (895). The sample analysis device, or test card (1000) is preferably placed on a flat surface. If the flap (1070) is not already open, the user opens it to access the sample application zones (1073), (1076). The sample application zones (1073), (1076) may be located in any portion of the transfer pad (1055). A blood sample to be tested is taken from the patient. The sample may be taken by any procedure known in the art. In a preferred embodiment, a sample of 5 µl of blood is added to each of the sample application zones (1073), (1076) zones and then the flap (1070) is closed. Each of the 5 µl samples is preferably collected independently of each other. The blood is preferably added directly to the device (1000), without any pretreatment. In preferred embodiments, an arrow (1002) or other indication (shown in FIG. 10A), for example the words "add sample here" shows the user where to place the sample on the test strips (1015), (1025).

To ensure that the flap (1070) has been closed correctly, pressure is preferably applied to the housing (835) above the pegs (875) to snap the pegs (875) closed. The top of the flap (1070) needs to be flush with the top of the rest of the second side (837) of the housing (835) for the test to run properly. Running buffer is added to the absorbent pad (840), which initiates lateral flow (885). In preferred embodiments, the running buffer includes one or more lysis agents, for example detergents, to lyse the blood sample and expose the intracellular MxA in the sample. When the running buffer reaches the diverting zone (850), it is diverted up into the flap (1070). It travels through the conjugate zones (872), (874), collecting the MxA binding partners, the low CRP binding partners, and the high CRP binding partners, as well as the control conjugate.

Since the conjugate zones (872), (874) bridge the diverting zone (850) on the lateral flow test strips (1015), (1025), the running buffer, which now contains conjugate, then travels into the transfer pad (1055), which includes the sample application zones (1073), (1076), and to the detection zones (805) on each of the test strips (1015), (1025). If MxA is present in the sample, the MxA test line (802) on the first test strip (1015) will be red. If a threshold low level of CRP is present in the sample, the low CRP test line (803) on the first test strip (1015) will be black. If a threshold high level of CRP is present in the sample, the high CRP test line (823) on the second test strip (1025) will be black. In preferred embodiments, the levels of detection are 40 ng/ml for MxA, 10 mg/L for low CRP on the first test strip (1015) and 80 mg/L for high CRP on the second test strip (1025). The results of the test should be visible after approximately 5-20 minutes, preferably within about 10 minutes. If the test was run correctly, the control lines (804) on both the first strip (815) and the second test strip (825) will be blue.

Since the control binding partner is on the flap (1070) and not on either of the test strips (1015), (1025), there is a true procedural control to this configuration. If the flap (1070) is not closed properly, nothing will show up in the detection zone (805), indicating that the test was run improperly.

In an alternative embodiment, the sample application zones (1073), (1076) are located on the receiving pad (845), before the diverting zone (850). In this embodiment, the running buffer travels through the sample application zones (1073), (1076), and then is diverted into the flap (1070).

In preferred embodiments of the configurations shown in FIGS. 8A through 8C and 10A through 10C, greater than approximately 1.2 ml of running buffer is placed on the absorbent pad (840). If less than 1.0 ml is added in embodiments where the diverting zone (850) is a gap, the buffer gets stalled at the gap because the gap holds approximately 1.0 ml.

Figure 11:
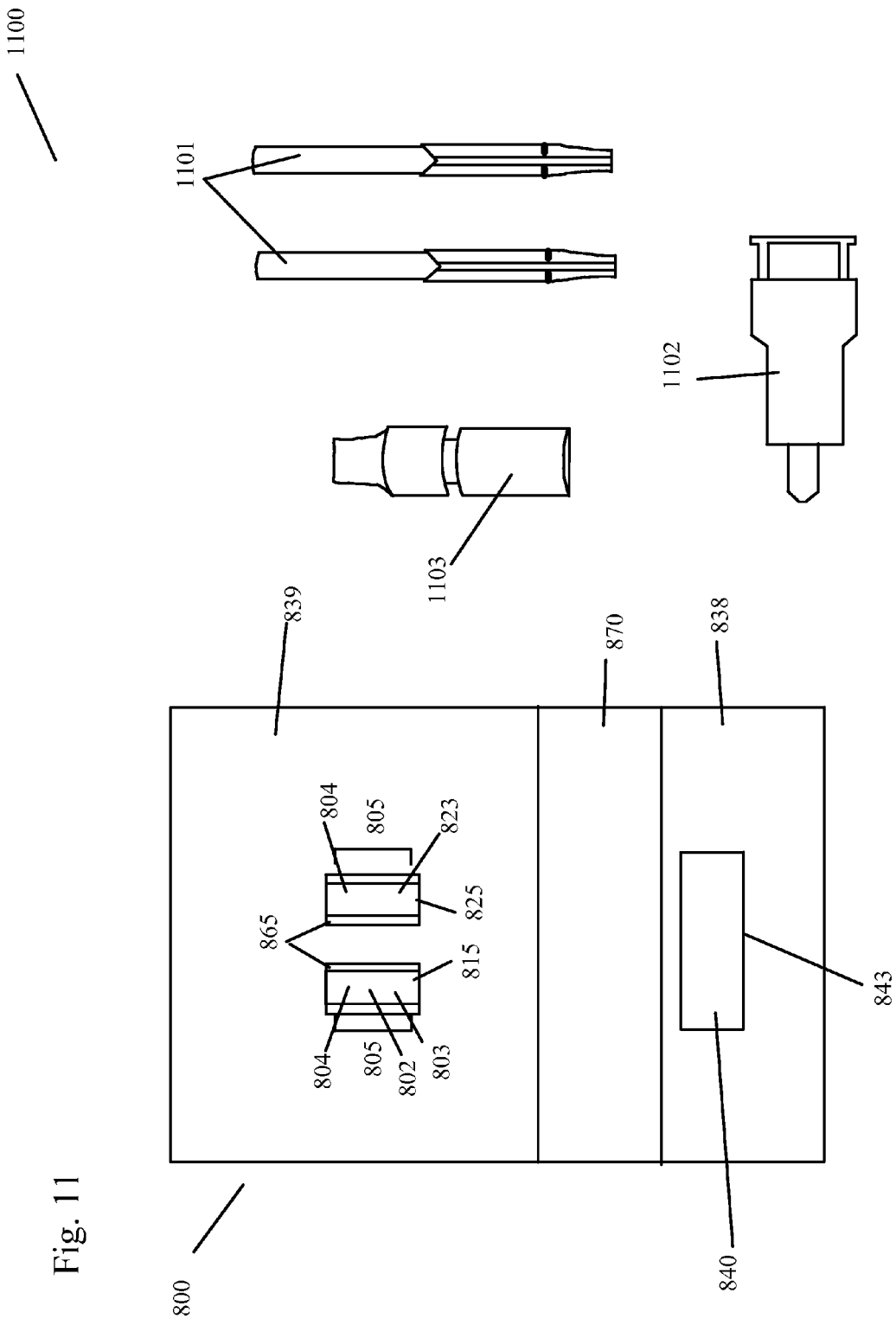
FIG. 11 shows a kit for sample analysis using a sample analysis device in an embodiment of the present invention.

As shown in FIG. 11, in one preferred embodiment, a kit (1100) includes the sample analysis device (800), (1000), a lancet (1102), one or more pipettes (1101), and a running buffer (1103). The lancet (1102) is used to make a skin puncture and one or more pipettes (1101) are used to collect the blood from the puncture site. In a preferred embodiment, 5 ul of blood is transferred from a first pipette (1101) to the first conjugate zone (872) and another 5 µl of blood is transferred from a second pipette (1101) and added to the second conjugate zone (874). The flap (870) is closed, and the running buffer (1103) is added to the absorbent pad (840), as described in the description of FIGS. 8A through 8C and 10A through 10C.

The diverting zone (850) preferably includes at least one feature that interrupts flow in the plane in which flow is occurring. The diverting zone may include a barrier, a gap, a ditch, or any combination of these features. The barrier is preferably an impermeable membrane (or substantially impermeable membrane) that may be made of any material that prevents the flow of liquid from continuing to flow in the same plane. Some materials for the barrier include, but are not limited to, inert materials, semi-permeable materials, plastics, hydrocarbons, metal, hydrophobic materials, Sephadex, Sepharose, cellulose acetate, a hygroscopic material (for example CaCl$_2$, CaSO$_4$ or silica gel), or hydrogels. The gap or ditch is any break in the plane of the lateral flow test strip that extends to a depth sufficient to stop flow. In one preferred embodiment, the gap is preferably at least approximately 0.1 mm deep.

The diverting zone (850) in FIGS. 8A through 8C and 10A through 10C delays or completely stops flow until the sample compressor/flap (870), (1070) is brought into contact with the rest of the device, and creates a bridge along which the fluid can flow. The sample compressor (870), (1070) acts as a bridge and redirects flow into a different plane. Flow is diverted into the sample compressor (870), (1070). This increases collection of the reagents on the sample compressor (870), (1070). For example, in embodiments where the conjugate is on the sample compressor (870), (1070), collection of the conjugate increases in devices with a diverting zone (850). In embodiments where both the sample application zones (873), (876), (1073), (1076) and the conjugate are on the sample compressor (870), (1070), the sample and conjugate both encounter the running buffer when it is diverted into the sample compressor (870), (1070), and a ½ sandwich or full sandwich (depending upon where the second binding partner for the analyte is located on the sample analysis device) is formed before the running buffer is diverted back to the test strips if the analyte is present in the sample. Embodiments with a diverting zone (850) and a sample compressor (870), (1070) increase speed, allow for better interactions between the conjugate and the sample, and allow for more sensitivity because more conjugate is placed into the fluid. In these embodiments, all of the fluid preferably interacts with the conjugate. This is a significant improvement over compressor embodiments without redirection, where approximately 20-30% of the fluid interacts with the conjugate.

Figure 12:
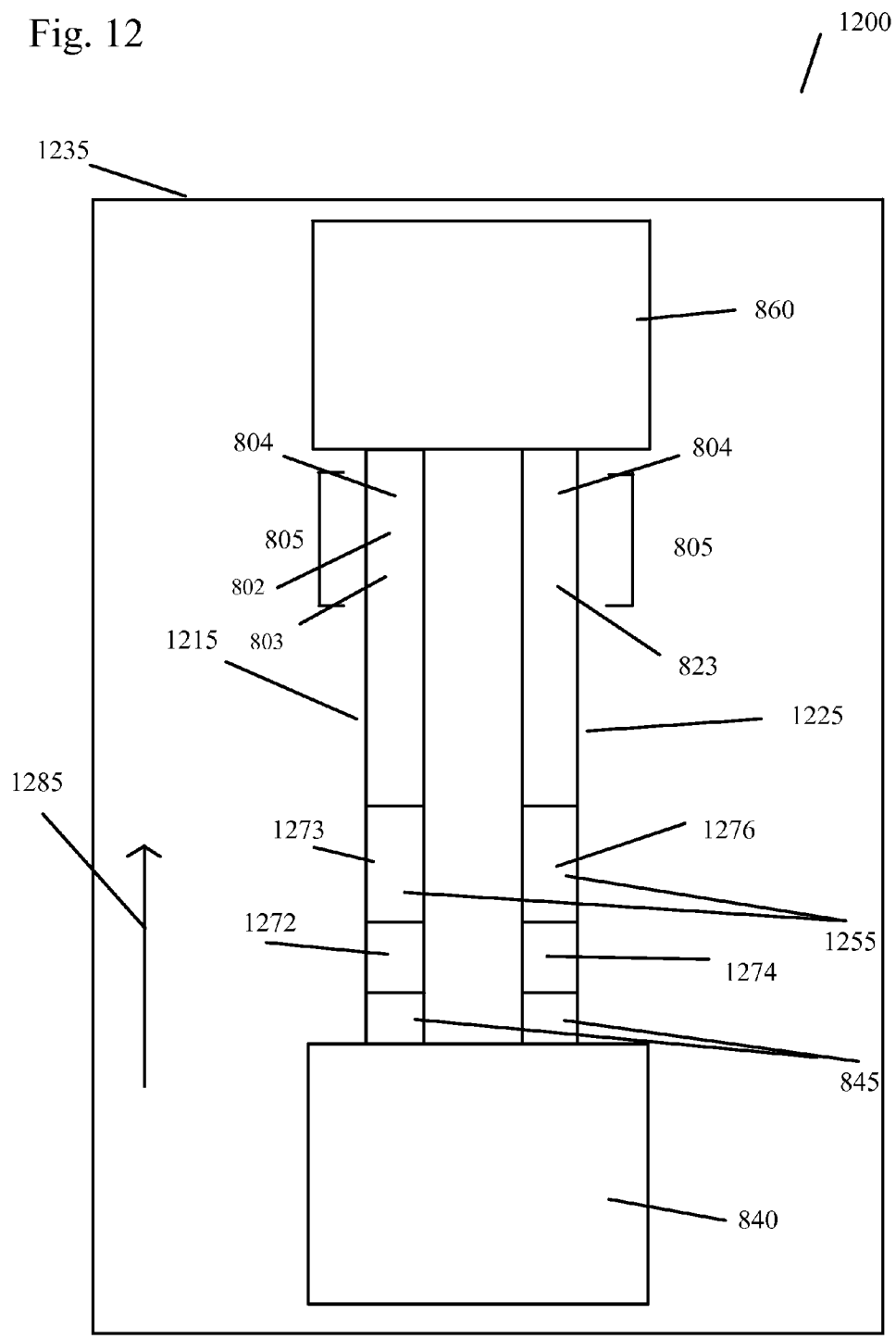
FIG. 12 shows a sample analysis device with dual test strips in another embodiment of the present invention.

Another preferred configuration for a bimodal dual test strip sample analysis device (1200) is shown in FIG. 12. This configuration is similar to the configurations (800), (1000) shown in FIGS. 8A through 8C and FIGS. 10A through 10C, without a second section (837) of the housing (1235) or a diverting zone (850). Instead, all of the components of the test are located in the same plane and flow proceeds laterally from the absorbent pad (840) to the waste pad (860). Note that this embodiment could also include a housing with a window to facilitate application of the buffer to the absorbent pad (840), a window located above each sample application zone (1273), (1276) for applying sample to the device (1200), and viewing windows for the detection zone (805). In one preferred embodiment, the sample analysis device (1200) is approximately 11.5 cm long (L)×7 cm wide (W). However, any size test card (1200) that accommodates all of the components may be used. There are two test strips (1215), (1225), each including a receiving pad (845), a conjugate zone (1272), (1274), a transfer pad (1240) containing a sample application zone (1273), (1276), a detection zone (805) and a waste pad (860). The device (1200) also preferably includes an absorbent pad (840) and a waste pad (860). While the conjugate zones (1272), (1274) are shown upstream of the sample application zones (1273), (1276) in this figure, in other embodiments, one or both of the conjugate zones (1272), (1274) are located downstream of the sample application zones (1273), (1276). The detection zone (805) of the first test strip (1215) preferably includes an MxA test line (802), a low CRP test line (803) and a control line (804). The detection zone (805) on the second test strip (1225) also preferably includes a high CRP test line (823) and a control line (804). The absorbent pad (840) is preferably a single pad that the running buffer is added to to start lateral flow. Similarly, the waste pad (860) is preferably a single pad that collects excess running buffer at the end of the test. However, in other embodiments, each strip could have a separate absorbent pad (840) and/or waste pad (860).

In preferred embodiments, the conjugate zones (1272), (1274) are colored due to the dyes in the sample conjugates and control conjugates. In one preferred embodiment, the conjugate zone (1272) that is used for the first test strip (1215) contains an MxA binding partner that is labeled with a red dye, a low CRP binding partner that is labeled with a black dye, and a control binding partner that is labeled with a blue dye. In this embodiment, the conjugate zone (1272) appears purplish. The other conjugate zone (1274) contains a high CRP binding partner that is labeled with a black dye and a control binding partner that is labeled with a blue dye. In this embodiment, the conjugate zone (1274) appears bluish.

In operation, a blood sample to be tested is taken from the patient. The sample may be taken by any procedure known in the art. In a preferred embodiment, a sample of 5 µl of blood is added to each of the sample application zones (1273), (1276). Each of the 5 µl samples is preferably collected independently of each other. In preferred embodiments, an arrow (1002) or other indication (shown in FIG. 10A), for example the words "add sample here" shows the user where to place the sample on the test strips (1215), (1225).

The blood is preferably added directly to the device (1200), without any pretreatment. Running buffer is added to the absorbent pad (840), which initiates lateral flow (1285). In preferred embodiments, the running buffer includes one or more lysis agents, for example detergents, to lyse the blood sample and expose the intracellular MxA in the sample. It travels through the conjugate zones (1272), (1274), collecting the MxA binding partners, the low CRP binding partners, the high CRP binding partners, as well as the control conjugate.

The running buffer, which now contains conjugate, then travels into the transfer pad (1255), which includes the sample application zones (1273), (1276), and to the detection zones (805) on each of the test strips (1215), (1225). If MxA is present in the sample, the MxA test line (802) on the first test strip (1215) will be red. If a threshold low level of CRP is present in the sample, the low CRP test line (803) on the first test strip (1215) will be black. If a threshold high level of CRP is present in the sample, the high CRP test line (823) on the second test strip (1225) will be black. In preferred embodiments, the levels of detection are 40 ng/ml for MxA, 10 mg/L for low CRP on the first test strip (1215) and 80 mg/L for high CRP on the second test strip (1225). The results of the test should be visible after approximately 5-20 minutes, preferably within about 10 minutes. If the test was run correctly, the control lines (804) on both the first strip (1215) and the second test strip (1225) will be blue.

In an alternative embodiment, the sample application zones (1273), (1276) are located upstream of the conjugate zones (1272), (1274). In this embodiment, the running buffer travels through the sample application zones (1273), (1276), and then to the conjugate zones (1272), (1274). In still other embodiments, the conjugate zones (1272), (1274) overlap the sample application zones (1273), (1276). In still other embodiments, the conjugate zones (1272), (1274), and/or the sample application zones (1273), (1276) may be located in the receiving pad (845).

In preferred embodiments of the configurations shown in FIGS. 4A through 8C, 10A through 10C and 12, the control is rabbit anti-chicken and the control conjugate is blue latex beads coupled to chicken IgY, In other preferred embodiments, there is at least one lysis agent, preferably a detergent, in the running buffer.

Simultaneous Detection of Intracellular and Extracellular Proteins

There are extracellular analytes and there are intracellular analytes. The detection of each is often a separate event. The intracellular analyte has to be extracted by lysing the cells so the internalized analyte is externalized and available for testing.

Methods disclosed herein simultaneously detect at least one extracellular analyte and at least one intracellular analyte. An "intracellular" target or analyte, as described in this embodiment, is an analyte that is inside a cell and does not touch anything within the cell (such as surface proteins, the cellular wall, or internal surfaces). An "extracellular" target or analyte, as described in this embodiment, is a completely extracellular analyte, that does not contact anything outside the cell. For example, the extracellular analyte is in the plasma, which does not contain cells. The cell can be removed completely, and the extracellular analyte can still be collected.

In contrast, viral particles, while being outside the cell, are attached to the cellular wall. It is well known in the art to blend a cocktail of antibodies to detect an intracellular bound fraction and a surface bound fraction. But, the methods described herein are different, and detect a lysed, intracellular portion and a disassociated serum protein.

In one preferred embodiment, the extracellular analyte is C-reactive protein and the intracellular analyte is MxA protein. This is a serological test for the detection of CRP and MxA antigens. MxA is an intracellular protein inside the white blood cells. CRP is an extracellular protein found in whole blood, plasma and serum.

In one preferred method, glass fibers, such as Whatman GD filters, physically trap the erythrocytes. Specific erythrocyte-binding lectins and/or antibodies can be added to physically bind to the erythrocytes in the glass fiber matrix. Leukocyte lysing solutions, which lyse the leukocytes to release the intracellular MxA, may be incorporated into the glass fiber filters.

In some preferred embodiments, the whole blood sample is added to the glass fiber filter. The liquid blood dissolves the embedded lysing agents, which lyses the leukocytes. Lateral flow immunochromatography is initiated by adding the running buffer. The running buffer then carries the suitable antibody conjugates which bind to the extracellular CRP and the newly released intracellular MxA. The entire complex moves into the detection zone where immobilized specific antibodies capture the respective complexes to form the sandwich. Different test lines are formed with MxA and CRP. These test lines can be visual, fluorescent, phosphorescent, chemiluminiscent, paramagnetic, or any combinations of these. Different dyes may be incorporated to distinguish MxA and CRP test lines. Any of the lateral flow assays and configurations described herein could be used to simultaneously detect MxA and CRP or other intracellular and extracellular analytes.

Agglutination of MxA and CRP

Some embodiments include a simple agglutination test for MxA and CRP in blood. As an analogy, the present inventors believe that the cement in a brick wall is holding the bricks apart instead of holding them together. The rationale is that if the cement is removed, the bricks coalesce and fall together into a heap. Therefore, if the cement is "inactivated" or removed, individual bricks coalesce together.

Gold conjugates and latex beads are colloidal particles that repel one another and hence are brought together in suspension. If the repulsive force is removed, or individual colloidal particles are cross-linked together, they coalesce and one can visualize the agglutinated particles. The cross linking to overcome this natural repulsion is accomplished by the presence of the antigen analyte in question.

In one preferred embodiment, MxA monoclonal KM 1124 and/or KM 1135 is conjugated to red colloidal gold particles. Anti-CRP monoclonal antibodies are conjugated to green latex beads of suitable size. In the presence of MxA, the monoclonal antibody KM 1124 and/or KM 1135 binds and, since there is a multiplicity of the epitopes recognized by KM 1124 and/or KM 1135, a natural cross linking of the colloidal gold takes place and one sees the clumping of the red colloidal gold particles. This process is antigen-dependent and fairly rapid, occurring generally within a minute or two. The same phenomenon takes place with the green colloidal latex beads coated with suitable monoclonal antibodies in the presence of a CRP analyte.

Clumping of red gold particles means at least a threshold amount of MxA is in the sample, indicating a viral infection. Clumping of green beads means at least a threshold amount of CRP is in the sample, indicating a bacterial infection. Clumping of both red and green particles mean either a co-infection or is indicative of an indeterminate result. Absence of any clumping indicates that the sample is negative for viral and bacterial infection.

In one preferred embodiment, the threshold concentration of C-reactive protein is equal to or greater than approximately 6-15 mg/L of C-reactive protein and the threshold concentration of MxA protein is equal to or greater than a serum equivalent of approximately 15-250 ng/ml. Since the MxA is an intra-cellular biomarker, the blood sample is preferably lysed during the assay to lyse the white blood cells and externalize the MxA antigen. In other embodiments, the sample is lysed prior to performing the assay. Any immunoassay format known in the art could be used for the agglutination assay. The reagents are added, and then the user waits to see if the reagents agglutinate in the presence of the sample.

Nanoparticles in Diagnosis of Viruses

MxA levels are elevated in quite a few but not all viral infections. Some exceptions to elevated MxA levels during infection are Hepatitis B and such chronic viral infections, including, perhaps HIV and hepatitis C. Sialic acid is on larger number of viruses. But, sialic acid is not on a few viruses, such as the Cox virus.

The combination MxA-CRP detector devices described above are preferably used in people with fever to distinguish between viral and bacterial infections. The sialic acid nanoparticle test is preferably used in all other suspected viral infections (with or without accompanying fever), including chronic viral infections. However, in some preferred embodiments, sialic acid replaces MxA in the methods and devices described herein.

In another preferred embodiment, a test includes MxA, CRP, and a sialic acid homolog nanoparticle.

In one preferred embodiment, the test line is a nanoparticle specific for a particular virus. Some examples include, but are not limited to, bird flu, and viruses that cause chronic infection, such as HIV or hepatitis C. The conjugate is either a) a virus specific nanomicelle with a dye inside or b) a sialic acid homolog nanomicelle with a dye inside.

For example, Nanoviricides, Inc. (West Haven, Conn.) has a Bird Flu specific Nanoparticle. That nanoparticle can be used at the test Line and a sialic acid homolog nanomicelle as the conjugate to detect the Bird Flu.

Another embodiment includes a broad spectrum viral detector. In this embodiment, the test line is a Sialic acid homolog nanoparticle that captures all viruses and the conjugate is a Sialic acid nanomicelle with dye inside.

In preferred embodiments, the test line is made of nanoparticles, not nanomicelles that contains the nanoparticles. The conjugate, on the other hand, is preferably a nanomicelle (analogous to a soap bubble) that takes up dyes inside the micelle. The lipid portion of the micelle is what is responsible for the "sliming" properties of the micelle.

The sialic acid embodiments may use any of the test strip configurations described herein, or known in the art, including those shown in FIGS. 4-8 and 10-12, or other assay configurations known in the art.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. A method for analyzing a sample for a presence of MxA and C-reactive protein, comprising the steps of:
    a) collecting a sample;
    b) transferring the sample to a sample analysis device comprising:
        i) a sample compressor comprising:
            A) a first reagent zone for detecting a low level of C-reactive protein comprising at least one first reagent specific to of C-reactive protein such that, when the sample contacts the first reagent, a first labeled complex forms if the low level of C-reactive protein is present in the sample and at least one second reagent specific to MxA such that, when the sample contacts the second reagent, a second labeled complex forms if MxA is present in the sample; and
            B) a second reagent zone for detecting a high level of C-reactive protein comprising at least one third reagent specific to C-reactive protein, wherein the third reagent only detects a level of C-reactive protein that is higher than the level of C-reactive protein detected by the first reagent, such that, when the sample contacts the third reagent, a third labeled complex forms if the high level of C-reactive protein is present in the sample;
        ii) a first lateral flow chromatographic test strip comprising:
            A) a first detection zone comprising a first binding partner which binds to the first labeled complex; and a second binding partner which binds to the second labeled complex; and
            B) a first diverting zone located upstream of the first detection zone on the lateral flow chromatographic test strip, wherein the first diverting zone interrupts lateral flow on the first lateral flow chromatographic test strip; and
        iii) a second lateral flow chromatographic test strip parallel in a lateral flow direction to the first lateral flow chromatographic test strip, comprising:
            A) a second detection zone comprising a third binding partner which binds to the third labeled complex; and
            B) a second diverting zone located upstream of the second detection zone on the second lateral flow chromatographic test strip, wherein the diverting zone interrupts lateral flow on the second lateral flow chromatographic test strip;
        iv) a first sample application zone where sample is placed on the sample analysis device, wherein the first sample application zone is located in a location selected from the group consisting of: i) on the first lateral flow chromatographic test strip upstream of the detection zone and ii) on the first reagent zone of the sample compressor; and
        v) a second sample application zone where sample is placed on the sample analysis device, wherein the second sample application zone is located in a location selected from the group consisting of: i) on the second lateral flow chromatographic test strip upstream of the detection zone and ii) on the second reagent zone of the sample compressor;
    wherein the sample compressor is in a different plane than the first lateral flow chromatographic test strip and the second lateral flow chromatographic test strip;
    wherein the first reagent zone of the sample compressor creates a bridge over the first diverting zone and the second reagent zone of the sample compressor creates a bridge over the second diverting zone, diverting flow onto the sample compressor and returning flow to the first chromatographic test strip and the second chromatographic test strip at downstream ends of the first diverting zone and the second diverting zone; and
    c) analyzing the sample for the presence of the low level of C-reactive protein, MxA, and the high level of C-reactive protein.

2. The method of claim 1 wherein the sample analysis device further comprises a first control binding partner located on each of the first reagent zone and the second reagent zone of the sample compressor and a second control binding partner immobilized in a control zone of each of the first lateral flow chromatographic test strip and the second lateral flow chromatographic test strip, wherein the first control binding partner is a binding partner for the second control binding partner.

3. The method of claim 1, wherein a threshold concentration to obtain a positive result for the low level of C-reactive protein in the detection zone of the first lateral flow chromatographic test strip is equal to or greater than a serum equivalent of approximately 6-15 mg/L of C-reactive protein.

4. The method of claim 1, wherein the threshold concentration to obtain a positive result for the low level of C-reactive protein in the detection zone of the first lateral flow chromatographic test strip is equal to or greater than a serum equivalent of approximately 10 mg/L of C-reactive protein.

5. The method of claim 1, wherein a threshold concentration to obtain a positive result for the high level of C-reactive protein in the detection zone of the second lateral flow chromatographic test strip is equal to or greater than a serum equivalent of approximately 60-100 mg/L.

6. The method of claim 1, wherein a threshold concentration to obtain a positive result for the high level of C-reactive protein in the detection zone of the second lateral flow chromatographic test strip is equal to or greater than a serum equivalent of approximately 80 mg/L.

7. The method of claim 1, wherein a threshold concentration to obtain a positive result for MxA in the detection zone of the first lateral flow chromatographic test strip is equal to or greater than approximately 40 ng/ml.

8. The method of claim 1, wherein a threshold concentration to obtain a positive result for MxA in the detection zone of the first lateral flow chromatographic test strip is equal to or greater than approximately 15-250 ng/ml.

9. The method of claim 1, wherein a first threshold concentration to obtain a positive result for the low level of C-reactive protein in the detection zone of the first lateral flow chromatographic test strip is equal to or greater than a serum equivalent of approximately 6-15 mg/L of C-reactive protein, a second threshold concentration to obtain a positive result for the high level of C-reactive protein in the detection zone of the second lateral flow chromatographic test strip is equal to or greater than a serum equivalent of approximately 60-100 mg/L, and a third threshold concentration to obtain a positive result for MxA in the detection zone of the first lateral flow chromatographic test strip is equal to or greater than approximately 15-250 ng/ml.

10. The method of claim 1, wherein a first threshold concentration to obtain a positive result for the low level of C-reactive protein in the detection zone of the first lateral flow chromatographic test strip is equal to or greater than a serum equivalent of approximately 10 mg/L of C-reactive protein, a second threshold concentration to obtain a positive result for the high level of C-reactive protein in the detection zone of the second lateral flow chromatographic test strip is equal to or greater than a serum equivalent of approximately 80 mg/L, and a third threshold concentration to obtain a positive result for MxA in the detection zone of the first lateral flow chromatographic test strip is equal to or greater than approximately 40 ng/ml.

11. The method of claim 1, wherein step c) comprises the substeps of:
    i) eluting the sample on the sample analysis device; and
    ii) visually determining a result from the first and/or second detection zones.

12. The method of claim 1, wherein the presence of MxA is indicated by a first test line located in the first detection zone of the first lateral flow chromatographic test strip and the presence of the low level of CRP is indicated by a second test line located in the first detection zone of the first lateral flow chromatographic test strip.

13. The method of claim 12, wherein the first test line displays a first color when positive and the second test line displays a second color different from the first color when positive.

14. The method of claim 13, wherein both the first test line and the second test line are located in the same space on the sample analysis device such that a third color is formed when both the first test line and the second test line are positive.

15. The method of claim 12, wherein the first test line is spatially separate from the second test line on the first lateral flow chromatographic test strip.

16. The method of claim 1, wherein the sample is a blood sample.

17. The method of claim 1, wherein the sample contains leukocytes.

18. A lateral flow device for detecting an analyte in a sample comprising:
    a) a sample compressor comprising:
        i) a first reagent zone comprising at least one first reagent specific to C-reactive protein such that, when the sample contacts the first reagent, a first labeled complex forms if the low level of C-reactive protein is present in the sample and at least one second reagent specific to MxA such that, when the sample contacts the second reagent, a second labeled complex forms if MxA is present in the sample; and
        ii) a second reagent zone for detecting a high level of C-reactive protein comprising at least one third reagent specific to C-reactive protein, wherein the third reagent only detects a level of C-reactive protein that is higher than the level of C-reactive protein detected by the second reagent, such that, when the sample contacts the third reagent, a third labeled complex forms if the high level of C-reactive protein is present in the sample;
    b) a first lateral flow chromatographic test strip comprising:
        i) a first detection zone comprising a first binding partner which binds to the first labeled complex; and a second binding partner which binds to the second labeled complex; and
        ii) a first diverting zone located upstream of the first detection zone on the lateral flow chromatographic test strip, wherein the first diverting zone interrupts lateral flow on the first lateral flow chromatographic test strip; and
    c) a second lateral flow chromatographic test strip parallel in a lateral flow direction to the first lateral flow chromatographic test strip, comprising:
        i) a second detection zone comprising a third binding partner which binds to the third labeled complex; and
        ii) a second diverting zone located upstream of the first detection zone on the lateral flow chromatographic test strip, wherein the second diverting zone interrupts lateral flow on the second lateral flow chromatographic test strip; and
    d) a first sample application zone where sample is placed on the sample analysis device, wherein the first sample application zone is located in a location selected from the group consisting of: i) on the first lateral flow chromatographic test strip upstream of the detection zone and ii) on the first reagent zone of the sample compressor;
    e) a second sample application zone where sample is placed on the sample analysis device, wherein the second sample application zone is located in a location selected from the group consisting of: i) on the second lateral flow chromatographic test strip upstream of the detection zone and ii) on the second reagent zone of the sample compressor;
    wherein the sample compressor is in a different plane than the first lateral flow chromatographic test strip and the second lateral flow chromatographic test strip;
    wherein the first reagent zone of the sample compressor creates a bridge over the first diverting zone and the second reagent zone of the sample compressor creates a bridge over the second diverting zone, diverting flow onto the sample compressor and returning flow to the first chromatographic test strip and the second chromatographic test strip at downstream ends of the first diverting zone and the second diverting zone.

19. The device of claim 18 wherein the device further comprises a first control binding partner located on each of the first reagent zones and the second reagent zones of the sample compressor and a second control binding partner immobilized in a control zone of each of the first lateral flow chromatographic test strip and the second lateral flow chromatographic test strip, wherein the first control binding partner is a binding partner for the second control binding partner.

20. The device of claim 18, wherein a threshold concentration to obtain a positive result for the low level of C-reactive protein in the first detection zone of the first lateral flow chromatographic test strip is equal to or greater than a serum equivalent of approximately 6-15 mg/L of C-reactive protein.

21. The device of claim 18, wherein the threshold concentration to obtain a positive result for the low level of C-reactive protein in the first detection zone of the first lateral flow chromatographic test strip is equal to or greater than a serum equivalent of approximately 10 mg/L of C-reactive protein.

22. The device of claim 18, wherein a threshold concentration to obtain a positive result for the high level of C-reactive protein in the second detection zone of the second lateral flow chromatographic test strip is equal to or greater than a serum equivalent of approximately 60-100 mg/L.

23. The device of claim 18, wherein a threshold concentration to obtain a positive result for the high level of C-reactive protein in the second detection zone of the second lateral flow chromatographic test strip is equal to or greater than a serum equivalent of approximately 80 mg/L.

24. The device of claim 18, wherein a threshold concentration to obtain a positive result for MxA in the first detection zone of the first lateral flow chromatographic test strip is equal to or greater than approximately 40 ng/ml.

25. The device of claim 18, wherein a threshold concentration to obtain a positive result for MxA in the first detection zone of the first lateral flow chromatographic test strip is equal to or greater than approximately 15-250 ng/ml.

26. The device of claim 18, wherein a first threshold concentration to obtain a positive result for the low level of C-reactive protein in the first detection zone of the first lateral flow chromatographic test strip is equal to or greater than a serum equivalent of approximately 6-15 mg/L of C-reactive protein, a second threshold concentration to obtain a positive result for the high level of C-reactive protein in the second detection zone of the second lateral flow chromatographic test strip is equal to or greater than a serum equivalent of approximately 60-100 mg/L, and a third threshold concentration to obtain a positive result for MxA in the first detection zone of the first lateral flow chromatographic test strip is equal to or greater than 15-250 ng/ml.

27. The device of claim 18, wherein a first threshold concentration to obtain a positive result for the low level of C-reactive protein in the first detection zone of the first lateral flow chromatographic test strip is equal to or greater than a serum equivalent of approximately 10 mg/L of C-reactive protein, a second threshold concentration to obtain a positive result for the high level of C-reactive protein in the second detection zone of the second lateral flow chromatographic test strip is equal to or greater than a serum equivalent of approximately 80 mg/L, and a third threshold concentration to obtain a positive result for MxA in the first detection zone of the first lateral flow chromatographic test strip is equal to or greater than approximately 40 ng/ml.

28. The device of claim 18, wherein the first detection zone of the first lateral flow chromatographic test strip comprises a first test line to detect a positive result for MxA in the sample and a second test line to detect a positive result for the low level of CRP in the sample.

29. The device of claim 28, wherein the first test line displays a first color when positive and the second test line displays a second color different from the first color when positive.

30. The device of claim 29, wherein both the first test line and the second test line are located in the same space on the first lateral flow chromatographic test strip such that a third color is formed when both the first test line and the second test line are positive.

31. The device of claim 28, wherein the first test line is spatially separate from the second test line on the first lateral flow chromatographic test strip.

32. The device of claim 18, wherein the first detection zone and the second detection zone each comprise a control line that is visible to the naked eye when the device is working.

33. The device of claim 18, wherein the first lateral flow chromatographic test strip further comprises a first sample application zone upstream of the first reagent zone, the second reagent zone, and the first detection zone, and the first detection zone is downstream of the first reagent zone and the second reagent zone.

34. The device of claim 18, wherein the second lateral flow chromatographic test strip further comprises a second sample application zone upstream of the third reagent zone, and the second detection zone, and the second detection zone is downstream of the third reagent zone.

35. The device of claim 18, wherein the first lateral flow chromatographic test strip further comprises a lysis zone comprising at least one lysis agent, wherein the lysis agent contacts the sample on the first lateral flow chromatographic test strip.

36. The device of claim 18, wherein the second lateral flow chromatographic test strip further comprises a lysis zone comprising at least one lysis agent, wherein the lysis agent contacts the sample on the second lateral flow chromatographic test strip.

37. The device of claim 18, wherein the first lateral flow chromatographic test strip further comprises a first sample application zone downstream of the first reagent zone and the second reagent zone, and upstream the first detection zone.

38. The device of claim 18, wherein the second lateral flow chromatographic test strip further comprises a second sample application zone downstream of the third reagent zone and upstream of the second detection zone.

39. The device of claim 18, wherein the sample is a blood sample.

40. The device of claim 18, wherein the sample contains leukocytes.

41. The method of claim 1, further comprising a step of determining whether an infection is bacterial and/or viral based on the presence of MxA and/or C-reactive protein in the sample.

* * * * *

UNITED STATES PATENT AND TRADEMARK OFFICE
CERTIFICATE OF CORRECTION

PATENT NO. : 8,962,260 B2  
APPLICATION NO. : 13/790160  
DATED : February 24, 2015  
INVENTOR(S) : Sambursky et al.

Page 1 of 1

It is certified that error appears in the above-identified patent and that said Letters Patent is hereby corrected as shown below:

In the Claims

Claim 1 (Column 39, line 26): replace "specific to of C-reactive protein" with "specific to C-reactive protein"

Claim 18 (Column 41, line 51): replace "a first reagent zone comprising" with "a first reagent zone for detecting a low level of C-reactive protein comprising"

Claim 37 (Column 44, line 36): replace "upstream the first detection zone" with "upstream of the first detection zone"

Signed and Sealed this  
Ninth Day of June, 2015

Michelle K. Lee  
*Director of the United States Patent and Trademark Office*